(12) United States Patent
Mahenthiralingam

(10) Patent No.: US 9,138,447 B2
(45) Date of Patent: Sep. 22, 2015

(54) ANTIMICROBIAL AGENT AND METHOD FOR THE PRODUCTION THEREOF

(75) Inventor: Eshwar Mahenthiralingam, Cardiff (GB)

(73) Assignee: UNIVERSITY COLLEGE CARDIFF CONSULTANTS LTD., Cardiff (GB)

( * ) Notice: Subject to any disclaimer, the term of this patent is extended or adjusted under 35 U.S.C. 154(b) by 859 days.

(21) Appl. No.: 13/058,753

(22) PCT Filed: Aug. 12, 2009

(86) PCT No.: PCT/GB2009/001972
§ 371 (c)(1),
(2), (4) Date: Jul. 15, 2011

(87) PCT Pub. No.: WO2010/018371
PCT Pub. Date: Feb. 18, 2010

(65) Prior Publication Data
US 2011/0269177 A1 Nov. 3, 2011

(30) Foreign Application Priority Data
Aug. 13, 2008 (GB) .................................. 0814830.6

(51) Int. Cl.
| A61K 35/74 | (2015.01) |
| A61K 31/232 | (2006.01) |
| C12N 15/52 | (2006.01) |
| C12P 1/04 | (2006.01) |
| C12P 19/44 | (2006.01) |
| C12R 1/01 | (2006.01) |

(52) U.S. Cl.
CPC ............... *A61K 35/74* (2013.01); *A61K 31/232* (2013.01); *C12N 15/52* (2013.01); *C12P 1/04* (2013.01); *C12P 19/44* (2013.01); *C12R 1/01* (2013.01)

(58) Field of Classification Search
None
See application file for complete search history.

(56) References Cited

U.S. PATENT DOCUMENTS

| 4,503,218 | A | | 3/1985 | Sykes et al. |
| 4,601,904 | A | | 7/1986 | Meyers et al. |
| 5,153,127 | A | * | 10/1992 | Andriollo et al. ............. 424/120 |
| 5,223,413 | A | * | 6/1993 | Nagy et al. .................. 435/71.3 |

FOREIGN PATENT DOCUMENTS

| GB | 1225379 | 3/1971 |
| WO | WO-95/11310 | 4/1995 |

OTHER PUBLICATIONS

Kim et al., "Modulation of Actinorhodin Biosynthesis in *Streptomyces lividans* by Glucose Repression of afsR2 Gene Transcription", J. Bacteriology, 2001, 183(7):2198-2203.*
Demain et al., "Phenylalanine Stimulation of Gramicidin S Formation1", Antimicrobial Agents and Chemotherapry, Jun. 1976, p. 1000-1003.*
Acumedia Yeast Extract, May 2011, Retrieved from < http://www.neogen.com/Acumedia/pdf/ProdInfo/7184_PI.pdf >.*
Cain, et al., "Identification and Characteristics of a Novel Burkholdeira Strain with Broad-Spectrum Antimicrobial Activity," Applied and Environmental Microbiology, Sep. 2000, p. 4139-4141.
El-Banna et al., "Pyrrolnitrin from *Burkholderia cepacia*: antibiotic activity against fungi and novel activities against *Streptomycetes*," Journal of Applied Microbiology 1998, 85, 69-78.
Korth, H., et al., "Isolation of an Antibacteral Tropolone from a Strain," vol. 252, 1982, pp. 83-86, published as Zentralblatt fuer Bakteriologie Mikrobiologie and Hygiene 1 Abt Originale A.
Li, et al., "Multiple Effects of a Novel Compound from *Burkholderia cepacia* against *Candida albicans*," FEMS Microbiol Lett 285 (2008) 250-256.
Seed, et al., Isolation and Characterization of Bacteriophages of the *Burkholderia cepacia* Complex, FEMS Microbology Letters 251 (2005) 273-280.
Smirnov, et al., Antibiotics of Aromatic Nature from Pseudomonads Depacia, Mikrobiologicheskii Zhurnal (Kiev) 1991, vol. 53, p. 41-45.
Wakimoto, et al. "Producton of Antibiotices by Plant Pathogenic Pseudomonads," Ann. Phytopath. Soc. Japan 52 : 835-842 (1986).

* cited by examiner

*Primary Examiner* — Suzanne M Noakes
(74) *Attorney, Agent, or Firm* — Foley Hoag LLP

(57) ABSTRACT

Provided are antimicrobial agents produced from *Burkholderia cepacia* complex (Bcc) bacteria, in particular from bacteria which comprise a cluster of polyketide synthesis genes. Also provided is use of the antimicrobial agents in the treatment of disease. Further provided are methods for producing antimicrobials, methods for detecting antimicrobial producing bacterial strains and kits for use in the methods.

19 Claims, 17 Drawing Sheets

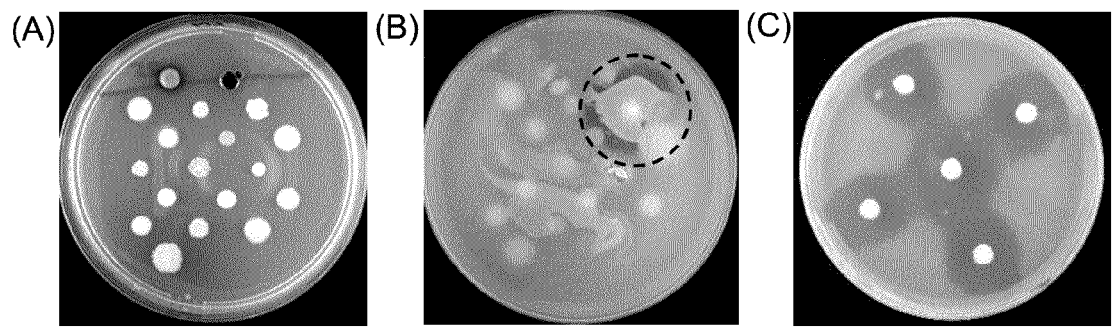
Fig 1
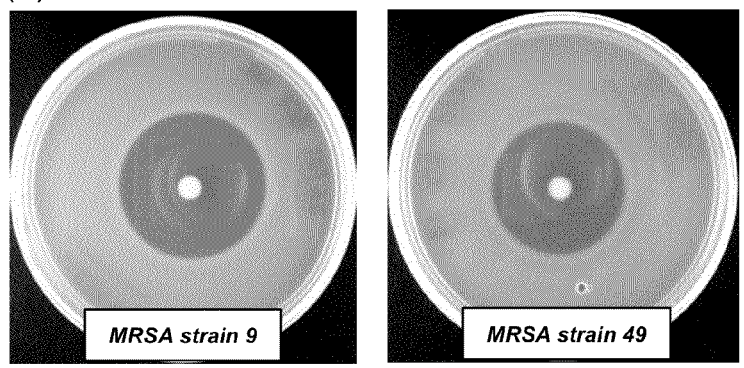
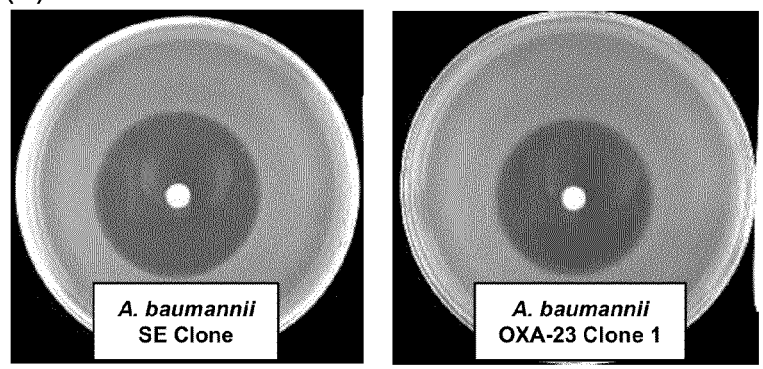
Fig 2

(A) Polyketide chain (B) Shikimate pathway derivative (C) Alkene side chain

```
ATGCAAGACATTCAGCAGCTCCTCGCGAAGAGCCTGACCGAAATCAAGCGCCTGAAGGCGGCCAACCAGGCGCTCGAGCAGGCCCGCCGCGAGCCGATCG
CGATTGTCGGCGCGGCCTGCCGCTACCCGGGCGGGATCGGCTCGCTCGACCAGCTCTGGACCGCGCTCGAGGCGGGCCGCGACGGCATCCGCACGATGGT
CGGCGAGCGCTGGCCGATGCAGCGCTTCCTCACCGACGATCCCCACCGGCCCGGCGCATCTACAGCGATGCGATGGGCCTGCTCGAGGCGATCGACGGT
TTCGATGCCGCGCATTTCGGCCTGCGCCACGACGAGGCGATCCACATCGACCCGCACATCGGCTGCTGATGGAAGTGGCCTGGGAGGCCTTCGAGGATG
CCGGCTACGCGGTGGACGCGTTCTCGGGCAGCCGCACCGGCGTCTACGTCGGGATCATGAACGACGACTACGGCCAGCTGCAGGGGCCGCTGGAGGCGGC
CAGGCCTCTACATCGGCTCGGGCATCGCCAAGAGCTGCCGCGGCGGGCCGGCTGGCCTACACCTTCGGCCTGGAGGGCCCGACGCTGGCCGTCGACACCGCC
TGCTCCTCGTCGCTGGTGGGCGTGCACCTGGCCGTGCAGGCGCTGCGGCGCGGCGAATGCGACGCGGCGCTGGCCGGTGGCGTGAACCTGATCCTTTCGC
CGCAGGGCACGGTGGTGGCCTGCCGCTCGCAGATGCTCTCGCCGAGCGGGCGCTGCCGCACCTTCGACGCCAGCGCAGACGGCTACGTGCGCGCCGAGGG
CTGCGGGCTGGTGCTGCTCAAGCGCTTGTCCGATGCCGAACCGCGACGGCGACCGGATCCTCGCGCTGGTCCGCGGCTCGGCCGTCAACCACGACGGCCGC
ACGCAGGGCCTGACCGCGCCGAGCGGCCAGGCGCAGCGGCGCGTGATCGCGGCGGCGCTGGCCGACCGGGCGTGGCGGCCGCCGAGGTCGGCTTCGTCG
AATGCCACGGCACCGGCACCGCGCTGGGCGATCCGATCGAGCTGCGCGCGCTGGAGGCCAGCTACGTGCTCGAAGCGGGCGAGCGCCGCCGCTGGTGGT
CGGCGCGCTGAAGTCCAATCTCGGCCACATGGAATCGGCGGCCGGTATCGGTGGCCTGCACAAGGCCATCCAGGTGGTGCGCCATCGCAGGGTGCCGAGG
AACCTGCATTTCGAGACCCTCAATCCGCAGATTCGCGTCGACCTCGAGCGGCTGCGCATCGCACCGCGAGGCGGTGGCGATGCCGGAACGGGAACGCGCGC
TGGCGGGCGTCAGCTCGTTCGGCTTCAGCGGCACCAATGCGCACGTGATCGTCGAGGCCTATGCGCCGCGGGACGATCGAGTGGGCGTGGACGGCTCGGC
ACATGAAGACGCCGCCAACGCGGAGGCTGCACCGCTGCAGCTATTCCGGCTTGCCGCGCATCGGGCGCCGCGCTGGCCGACTACGCGCGCCGGTACCTC
GACTGGCTCGACGACGCGCACGCGCAAGCCCGGCTCGATCCGGCCGCGCTTCGCTACACGGCCGCGGTGGGCCGCGAGGCCGGCTGCCGGATCG
CGCTGAGCTTCGAGACGCTCGATGACCTGCGCGCCTGCCTGCGCGGAATACCTCGACGTGGCCGGCGGCGACCCGAGCGAGCCGGTGCCGAAATCCTGCGC
GGCCCGACTGGGTGATCGGCGGCGCGGCCGATGTCGACTGGCGCGTGCCCGGGCGCTGCATGCGCACCCCGGCTTCTATCGCGAGCGGGTCCAGCAGGCC
TGGGCGCGCCTCGCGTCGCGCGGATGGCGCCGCGCGCGTTCGCGGCTCTGCGCGGGCGGCGATGCCGGCTTGCCGGCCGAGCGGACGCTACCGC
ACACGGTGCACCGCTGGGCGCTCGCGCAGCTGCTAGTCCACCTCGGCCTGCAGCCGGCCCGCGTGAGCGGCCATGGCGCCGGCGAGTATGTGGCGGCGGC
CGTCGCGGGCCTGGTCGACTGGGACACGGCGCTCGGCCTCGCGGCCGGCGAGGCACTGCCGGCCGGCTTCAAGGCGGGCCGCGCGCGCTGCGAATTCACC
AGCCGCTTCGGCACGGGCGAGCTGCCCGAGTCGTGGCAGCGCGACGGCGGCCCGGCGGCGGCCGACGCGGCTCCGCTCGGCGACGAGGCTTGGCCCGAGC
ACGCGCAGGGCATCGTGGTCGAGCTGGGCGCGGGCCTCGCGCTGCGCTGCGCTCGGCGATGCGGCCGACGAGCGCCTGTTCCGCTGGACCCACGGCCACCAA
TCGCGACCCGGCCCGGCCGCTCGAGGCCTTCCTCGCGCAGGCCTACATGCGGGCCTGCCGGTGCGCTGGGCGCCGCTGTTCGAGGCGCAGGCGCCGCGC
CGCCAGAGCCAGCCCGGTTATCCGTTCCAGCGCGAGCGCGTGTGGACCGACTGGGGGTATTCGTTCGACGCGACGCTGCCGTCCACCGTCGGCCGCGCCG
GCGGCGGCGTGGCGCCGCGCCTGCCGGCGCTCGCCACCGGGCTGGCCGCGGAGCCGCTCGATCACCCGGTGCTGCGCAGCCTGTTCGCGTGCCCGTCGGG
CGCACGCAATTTCTCGGGCGAGCTTTCGCTCACGGCGCTGCCCTACCTGGCCGACCGCATCCTCGGCGAGATCGTACTGCCGGCCAGCGCGCAGTTC
GACCTGATCGCCACCGCGGGCCGCATGCTGGCCGGGCCAGCCGCTGCTGATCGACGAGCTGCAGCTGCCGAACCGCTGCGTGCTCGGCGACGAGCCGC
TCGAAGTCTACTGCCACCTGCGGCCCGCCGACGGGCGCGTCGAGCTGCATGGGCGGCCGCGCGGCGCGCCGGGCTGGACGCTCCACGCGCGGGCGCGCAT
CGCGCCGACGAGGCCCACGCGGCCAACGCGCCGGCCACCGTCGATCCGCGACCAGGGCGAGCCCGTCGACGCCGAAGCCGGTGCGGTGCCGCGCCACTAT
CACGCGATCGCGCAGGTCGGGCTCGAATACGAGGCCGACTTCCAGGGCATCTTCGAACTGTCGCGCGGCACCGGCTGCGCGCTCGCCAAGATCGCGCTGC
CGCCCGGCGTCGACCAGTCGCTGGACGGCTACAGCACCCACCCGATCCTGCTCGACGCCTGCCTGCAGGCGGATTTCCGCAGCCTCGCCGCCCGATGCCGG
CGGCGAGCTGCTGATCCCGGCCGCGATGCGCGGCATCCACCTGTTCAGGCCGCTGCCCGAACTGATCTGGTGCCGCGTCGAGGTCCTCGCCGACGACGGC
GGGCGCGGCACCCAGCACGCCAAGCTGACGATCGTCGACATGCAGGGCGAGCCGGTGATGCGCATCGACCGCTTCGAGACCACGCGTTACACGGGCGCCG
TCGCCGCCCGCTGCCGAGAACTGGACCCACTGGCTCTACGACCGGCACTGGGTGCCGCCCGCCGTCGCGCGGCTTCCTCGTCGTCGCCGAGCGTGCCCC
GCGCCACTGGCTGCTGCTCAGCGACGGCGGCACGGCCTGCGCGGCGCTCGCGACGGTGCTGGCCGCGCGCGGCGATCGCGTCTCGGTGCTCGGCGCGAG
GCCGCGCCGGCCGACGCGGACGGCTTCGGCGCGTTGATCGATGCGCGGCGGCCGATGGCGGCCTCGACGGCGTGATCCACGGCTGGTCGCTCGACGCT
TCGATCCCGAGGCGCACGGGCCGGGCACGAGGCCGTGTCGGACGAGGCGCTGGCGCGCTGCGCGCAGGGGCCGCTGTGGCCTATGCCAGGCCGCGCTCGC
GCCGGGCCGGCGCGAACTGGCGCTGCATTTCCTCACGCGCGGCAGCCAGCCGGCCGGCGGCTCGCGCGTGCGGGCGCCGCTGGCCGCGCTGGCCTGGGGG
CTGGTGGGCAGCTTCGTCAACGAACACGCCGCCCGGCGCGCCTGGTCGATCTCGACCCCGACAGCCGCGACGGCCCGCGGATGCCGCGCTGCTGGTGC
AGGCGCTTCACGCGGACGGCGGAGGAGACGCAGTACGCGGTGGCGGCGCCGCTGCTGGTGGCGCGGCTGCGGCGCGCCGCCGCGCTCGCGGCGCCAGC
GCCGGTGATCGATCCCGAGGCCAGCTACCTGATCACCGGCGGTTACGGCCAGCTCGGCATCGAGACGGCCACCGCGCTGGCGCGGCAGGGCGCGCCAC
CTGGTGCTGGTGGGCCGCGATCGTCCCGCGCCGAGGGCGACCCGGCGCTGGCCGGCCTGCGCGAGATGGGCGTGCGACTGACCGCCTGGCGGCCGACG
TGGGCGAGCGCGCCAGCTTCCTGCCGCGCGCCTGGCCGAATGCCTGCGCACGCTGCCGCGCTCAAGGGCGTGGTCCATTCGGCGGGCAGCCTGGACGACGG
CGTGCTCGACGACCAGGACTGGGGGCGCTACCTCGCGGTGTTCGCCGCCAAGGTGGCCGGCACGCTCAATCTCCATCACGCGCTGCGCAAGCATGCGCTC
GATTTCTTCGTGCTCTATTCGTCGGCGGCCGCGCTGCTCGGCAACCCGGGGCAGACAACTACGCGGCCGCCAATGCTTTCCTCGACAGCTTCGCCGCCT
ATCGCCGCGGCCTCGGGCTGGCAGGGCTGGCGATCGGCTGGGCCGGCTGGGCGGGCGGGGGATGCCGCCGGCGGGGCGAGGCGCGCGCCGAGGCCAC
GATCGGCCTGATCCCGCCGGAGCAGGGTGCCGAGGTAATCGCCCGCCAGTTCGCGCATCGCGACGGCGATTTCGCCTTGATCCCGATGCGGCTCGCCGCG
CTGGCCGGCCAGGACCGACATGCCCTGGCTGCGGCTGCTGGCGACGGCTGGTCGAGGCCGAGGCAGGCCGGCAGGGGCGGAGCACCGCGCCTCG
AGCGCCGGCCGGCGGCACGGCCGGCCGGCAGCACTGCTGGCCGGGCCTCGCGAGCCTCGATGCGGCGCGCGCGGCGCCTGAAGCGCCATCTCGAGGC
CGCGATCCGCAAGCTGCTCAACCGCGCCGATACGCTCGACGATCGCGCCAGCATGTTCGATCTCGGTCTCGATTCGCTGCTCAGTATCGACCTGCGCATG
CAGCTCCAGAAGGACCTGGCCTGCAGCCTCTCGACCACGGTGCTGCACGACCATCCCACCATCGAGCGCGCTGGCGGGCTTCCTGGCCGAACGCGTGCCGTG
CGCCGCCGGCGGGACGGTTCGCGCAGGGGCCGCGGGCGGTGCGCCCGAGCGTGCGGCAGGGCACCGGCGCGCTGCCGGCGCCACTGGGGCCGCGGCTGCATGCCGT
ATCGTCGGCCTGCCCGTGCCGGCCGGGGCGCGTCGGCGCTGCATCCGCTGCATCCGCTGCAGCGGCAGCCGGCCCGCTGCGCGGCCACGTTCGCG
GCCGAGCGCGTCGTGCCGGCGGCGCGGCGCTGCCGCCCGGCGCCGGCCCCGACGACATCGCCATCATCGGCGTATCGGGCCGCTACCCCGGCGCGGCCG
ACCTCGGCGCGTTCTGGGACAACCTGCGCGACGGCCACGACGGCGATCACCCCGATCCGCGAGCGCTGGAACCACGACGCGCTACTTCGACCGGCAGCG
CAACGTGCCCGGCAAGAGCTACAGCGCGTGGGGCGGCTTCATCGAGGACGTCGACGCCTTCGACCCCGGCCTTCTTCAGCATCTCGCCGCGGATGTCGCC
TACCTCGATCCGAAGGAGCGGCTGTTCCTCGAGACGGTCTGGAACCTGCTGAGGAGGCGGGCGAGACGCGCGAGCGCATGCAGCAGGCCTATGGCGCGC
AGGTGGGCGTGTTCGTCGGCGCGATGTACCAGCTCTATGGCGCCTGCGCGGCCGACGAGGGCGAGCCGTGGCCACCGCGCTGTCCTCCTACAACGCGAT
CGCGCATCGCACCTCGTACTTCTTCAACCTGCGCGGGCCGAGCATCGCGCTCGACACAATGTGCTCGTCGTCGCTGACGGCGGCTCACTACGCCTGCCGC
AGCCTGCTCGACGGCGACTGCGCGCTGGCCATCGCGGGCGGCGTGAACCTGTCGCTGCATCCGCGCAAGTACGCTCGGGCGCTGAGCCAGGCGCAGATCGTCG
GCAGCCATGCCGACAGCCGCAGCTTCAGCGACGGCGACGGCTACCTGCCGGCCGAGGCGTGGGCGCCGTGCTGCTCAAGCCGCTGGCCCGCGCGCTGGC
CGACGACGACCGGATCCTGGCGGTGATCAAAGCCTCCTCGGTCAACCACGGCGGCCGCGCGACCGGCTACTACGCGCCGAACGCGAACGCCCAGGTCGAC
CTGATGCAGGCCAGCTTCCGCAAGGCCGGCGTTCGCGCAGGGCGTGCGCCCAGCTGTCGGCCAGTCGATCGATCTCGAGGCCGCCCCCAACCGCACCAGCCTCGGCGACGCGGTCAGC
TGCGCGCGCTGGCGCGCGTGTTCGACGGCACCGCGCGCGACGGCGGCGCGTGCCGATCGGCACTGTGAAGTCGAACATCGGCCATCCTCGAGGCGGCCTC
GGGCATCGCGCAACTGACCAAGGTGATCCTGCAGATGCAGCACGAGACGCTGGTGCCCTCGATCAAGACCGAGCCCGTCAACCCCAACCTCGACCTGGCC
CACACGCCGTTCCGCCTGCTCTCGCGGCAGGCGGCCTGGCCGTCGATCCGGCGGCCGGCCGCCACCGGTCAGCTCGTTCGGCGCGAGCGGCCGCGA
ACGCGCACCTGATCGTCGAGGCCTTCGAGACGGTCGAGGCGGAGCCCGCGCCAGCCGTCGCGCAAGCGGCCGCCGCGGCCGAGATCGTGGTGCTGTCGGC
GCGCACGCCGGCTCAGTTGCGCGAGGTGGCGCGGCGCCTGCTGGCCTGGCTCGCCACGCGGCAGGCGCGGGCAGGCGGAATCGGCGGTGCCGCTGCCC
GAGCGCGGCCGCGCCTGCTCGCTCGCGAATCTCGCGCACACGCTGCAGATCGGGCGCGAGGCGATGGACTGCCGGCTCGCGCTGCTGGCCGACAGCCTCG
ACACGCTTGGCGATGGCCTGCGGCGTTTCCTCGGCGAATCGGCCGGCGGCGCGACCCGCGATCTACCACGGCAACGTGCAGGACCAGCTCGAGATGCG
CAACCTGCTGGCGGGGCCCGCCGGCGACGGCGATGGCGCAGACCCTGGTGGCCGAACGCAACCTGGAGGGGCTGATGCTGCACTGGGTCCAGGGCGGCAAC
GTGCCCTGGGCCGCCCTGCGCGAGGGCCGGCCGGCGCGCCGCCTGGTGCTGCCGACCTATCCGTTCGAGCGCGAGCGCTACTGGCTGTCCGGCGCGAGCG
ACGCCGCGGGCCGCGGCGGGCGAGCCGCAGGTCCCTGCCGAGCCGGCCGAGGCGGCCAGCGAACCCAGTGTCGTCGATGGCGGGCCTGA
```

Fig 10A

```
TTGAACGACTACAAGGCATTGCTCAAGAGCTCGATCCGCAAGATCCAGGAACAGGATCGGCGCATCCGCGAACTCGAGTCCGGCGTCGACGAGCCGGTGG
CGATCATCGGCATGTCGTGCCGGTTTCCCGGCGCACCCGACGCCGAAGCGTTCTGGCGCGCGATCGAGGCCGGCGCCGACACGGTGACGACCATGACCGG
CCAGCGCTGGGAAATGGAGGCCTGGCATACCGACGCGGCCTCGGCCGAGGCCGCCGAGGCCGCATCTACACGCGCCGCTTCGGCCTGCTGGAGGAC
ATCGACGGCTTCGAGCCGGGCGCCTTCGGCATCTCCGAGGAGGAGGCCCCTACATCGATCCGCAGCACCGGCTGCTGCTCGAACAGGCCTGGTTCTGCC
TGGAGCACGCCGCCTCGACCCGAAGACGGTCAAGGGCAGCGACATCGGCGTGTTCGTCGGCCAGATGAACAACCACTACGCGCGCCTGATCCGCCCCGC
CGAGGACCTCAATCCCTACGTGGGCGCCGGCAGTGCGCCGAGCGCGGCGGCCGCGCCTGTCCTACGTGTTCGCCCTGAAGGGGCCGAGCATCACCATC
GACACGGCCTGCTCGTCCTCGCTGGTGGCCGTGCACTTGGCCAGCCAGAGCCTCGCGCTGGGCGAGTGCGGGATGGCGCTGGCTGGCGGCGTGAACCTGC
TGCTGAGTCCCGAGACGGCGGTGGGCGCCTGCGTCGCGCGCATGCTGTCGGCGCGCGGGCGCTGCAATACCTTCGGCGGCGAGGCCGACGGCTACGTGCG
CGCCGAGGGCTGCGGCCTGGTGCTGCTCAAGACGCTGTCGCGCGCGCGCCGACGGCGACACCGTGCTGGCCGTCATCCGCGGCTCGGCGGTGAACCAG
GACGGCCGCAGCCACGGCCTGAGCGCCCCGAACGGCCCGGCCCAGGTGCAGGTGATGCGCGATGCGCTGGCGGCGCGCGTCGACCCGGCCGAGGTCG
GCTACCTGGAGACGCACGGCACCGGCACCCCGCTCGGCGATCCGGTCGAGGTGCAGGCGATCGACACCGTCTACGGTCGCGCCGAGGGACGCCGCTCGCC
GCTCGCGCTGGGCGCCGTGAAGGCCAACATGGGCCACGGTGAATCGGCCGCCGGCATCGCCGGGCTGATCAAGCTGGTGCAGCTGCTGCGGCACGACAGC
CTGCCGCCGGTCGCGCATCTCGATGCGCTGAATCCGCATTTCGACGGTCTCAGCGACCAGCTGCTGCTATTCCCGAAGGGCGCCGCCGCCGCGTGGCCGCAAG
GGCGCCCGATGCGGTGGCCGCGCTAAGCTCGTTCGGCTATACCGGCACCAATGCGCACCTGCTGCTCTCGCCCGGCGACGCGCTCGACGCCGATGCCGAAGC
GGCCCGTCCCGCGCATCGCTTCGAGCGCGCCGCTACTGGCTGCCCGACCACATGACGGCGCGCGGGCGCGCTGCCGGCGCTGTTCGAGCGGTACGC
CATCCGTTCTTCGCGACCAGCATGAACGAGCCCGACGGCGGCTCCCTGCTGGCCGGCGAACTGTCGCTGGCGCGTCAGCCCTTCCTGCGCGACCACGTGG
TGGCCGGCGAGGTGGTGCTGCCGGCCAGCTGCTTCGTCGATATGGTGGTGCATGCCTGCGCGGCCGCGCTCGGCGCGCCGCGCATCGAACAGATGAC
CCTCTTGCAGCCCTGCGTGCTCGGCGAGACGCCGCTGGGCCTCTATTGCCGCGTCGGCCCGCCGGCGGCGACACGCTGGCCGTCGACATCCTGACGCGC
CGCGCCGGCCGCGAGGACTGCCAGCACCATGTGCGCGCGAGCGTGCGCGCGGTGCCGGCCGCGGCCGCGCGGCAGCACGACCTGGCTGCCGATCGCCG
CCTGCCCCGAGCCGGTTTCGCCCGAGGCGCTGCGGCGCGAGGCGCGCGAGGCCGGGGTGGCCTACGGGCCGGCATTCCGCGCGATCGAGGGCCTGTGGCG
CGGGCCGGCGTCGCGCTGGGCCGCATCGTACGGCCGGCCGCGCTGGGCGCCGGCTGGAACGGCCCGGGCCTGCACCCGGTGATGCTCGACGGCCTGCTTC
CAGGTGATCGGCGCGGCGGCGGCCGGCGAGGGCGGCGCGGACAGGCCCGCGCGGCCTGTTCGTGCCGGCCGCGCTGCACGGCGTGCCGCGACGGCGTGCAGG
ACGGTGGCCCGCGCGCGGCCACGCTCTGGTGTGTCGCGCGCATCGACGGGCCCGGCGCGCCCTGGGCCGACGATGCCTCGCTGCACGACTACCTGCGCGG
TCGCGACAACTTCTCGGTGCAGCTGCGCGTGTGCGACGAGCAGGGCCGCGAACTGCTGTCGATCGAGCGCTTCGAGGCGGCGCGTCATCGCCCGCGGGCA
GCCGCCGAGGCATGGCGCGACTGGCTGCTGGAGCGGCACTGGCTGCCGGCCGGCGCGCCGCGCGACGGGCTTCGCGCTGACGGCGGCGGCGCTGGTCG
CCGACCTCGGCGCCGATGCCAACGCGGCTTCCTACGTGGTGAGCGACGCGCTGCGCCGCGGCTTCGACGAGATCGCCGCGCGGCTACGTCGCGCGCGCGCT
CGACGCGCTCCAGCTGACGCCGGCCCGGCTGCGCGAGGGGTCCCGTCGGCGCAGCAGCTCGAGTCGCAATACCCGATCGCGCCCCAGCATCACCGCCTG
GTGCCCCGGCTCCTCGGCGACGCTGCCCGCGCGTCGCGACGCACCCCGACGTCGAGGCCGAGCTCGCCGCCCCCTCGGCGGCGAGACGC
GCGAGCTGGACCTGCTGGTGCGCTGCGGCGAGGGTGCTCGCCGACGTGCTGCGCGGCGGGTCGGCGCGCTGACGCTGCTGTTCGAGCCGGCCGCGCCGCGTACGGC
CGACGTGGAGCCGGTCTACCAGGACAGCGCTGGCAGCCGCGCGCTCAACGACCGGATCGCGGCGCTGCTGGAGCGGCTCGCGACGTCGCGGCCCGAGGGG
CGGCCGCTGCGCGTGCTGGAAAGTCGGCGCCGGCACCGGCGCCACCACGGCGCCTGCTGCCGGTGCTGCGGCCGCGCGGCCGAGTACGTGTTCACCG
ACATCTCCGCGCACTTCCTGCATCGCGCCCAGGACAAGTTCGCCGGCGATGCCTTCCTCAGCTATCGCACGCTCGACCTGGAGCGCCCGCGGGCGAGCA
GGGCTTCGAGGCCGGCGAATTCGACGTGGTGATCGCCGTCAACGTGGTGCATGCCACGGCGATATCGCGCGTTCGCTCGCGCATCTGTCGAGCTGCCTG
ACCGAGGGCGGGATGCTGGTGCTGCGCGAGGTGACCGAGCCGCAGGCCTGGCTCGACCTGAGCTTCGGGCTCACGCCGGGCTGGTGGGGTTTCGCCGATG
CGCCGCTGCGCGAGCACGGCCCGCTGCTCGACGCGGCGCAATGGGAGCAGGTGTTGCGCGGAACAGGGTTTCGAGCCGGCGCTGGCCACCGCCGAGGCGGG
CCGCACCGAGAGCGTGATCGTGCCGCAGGACTGCCGCGAGCGGCCGGGCACTGCGTGGTGTTCGCCGACCGGGGATGCCTGGTCGGCCGGGCTGGTG
GCGGCGCTGCGCGACAGCGGGCGGCGCGTGTCGGTGGTGGAGGCCGAAGCGGGTGCCGAACGCGCGCCGCTCGAGCGCGACGATTTCGCCGCGCGCCTGG
AAGCGCTGGAGGCCGAGCACGGTGGCGTCGACGAACTGGTCTATGCCTGGTCGGCACGTCCGGCCGCGCTCGATACGGTCGATCCCGAGACCGCCGGGA
GCCCTATCTGCGCGGAGCCGCTCGCGCTGTGCCAGGCGCTCTTGCTGCCGCGGCTGCTGCGCTCGAGGCCAGCTTCCTGACGGCCCGGCGCGCAGGCCGTC
GCGGGTCGCGTGTCCGAGCCGCTGCAGGCCCTGCTGTGGGGCCACCTGCCCGCCTTCGTCAACGAGAACGCGCGCTTCGCGCGGATCATCGACGTGCGATC
GCGACGAGCCGGCCGGCGCGCCCTGCTCGGCGCGCTCGCGCAGCGCGAGGATTGCCAGATCGCGGTGCGCGGCGAGGCCGGCTTCGTGCCGCGGCTGCG
CCGCGCCGCCCTCGTCGAGGCCGGCGCGCGGGTGGTGTCGGCCGAGGCAGCTACCTGGTCACCGGCGGCTTCGGCGCGCTGGGGCATCGAGACCGCCCGC
GCGCTGGCCGCGCAAGGCGCCCGGCATCTGCTGCTGCTCGGCCGCCGCCTGCCGCCGTCGGCCGAAGTCGCGCTCGCCGGCCTGCCGCGAGCAGGGCCTCG
CCGTGCACACGCTGCTGGCCGATGTCGGCGACGAGGCGTCGCTGCGCGCGGCACTGGCCGGCGTGCCGGCCGAGCTGCCGCCGCTCGCGCGGCGTGGTGCA
TTCGGTCGGCGTGCTCGACGACGGCGTGATCGGCCAGCAGAGCTGGGCGCGCTACCAGCGCGTGCTGCATCCGAAGCTGGGCGGCGCGCTGCTGCTGCAT
CGGCTGCTCGCGCGCCGCCGCCTCGATTTCTTCGTGCTGCTCTATTCGTCGGCGGCCGGGCTGATGGGCAATCCCGGCCAGGCCAATCACGCCGCCGCGAGCG
CCTTCCTCGACGCCTTCGCCTGGTATCTGCGCGGCCGGGCGTGCCGGCCGTCGCGCTCGACTGGGGCGCCTGGTCGAGATCGGCGCGGCCGCCGCGCG
CGACCGTGGGCCGCGGCTCGCGCCCGAGGGCTCGATCGCCGGCGTGATCGCGCCCGAGCAGGGCGCGGCCGTGATGGCGCCCAGTTCGGCTCGCGCAAT
ACGCAGCTAGCCGTGCTGCCCCTGAAGCTGAACCAGCCAATCCACGCGAGCCGCCAGCCGCAGGTGCGGCGCCTCTGGCCGAATTGCTGGCCGAGGCCAC
CGGCCGGCGGGGCGACGCAGGCGACCGGCGCGGCGGTGTGACCGGCGCGCGGCCGGCCGATGCCGAGGCCGGGGATGCCTGGCTCGACCGCCTGCTGCG
CGTGAGCACGCCGAGCGCCCGCCGCGAGCTCGGCGAGTATCTCGAACAGACGGCGGGAAGCCTGCTCAGGCGGCCGGCCGGATCGACGGGCAGGCCAGC
CTGTTCGACCAGGGGCTGACTCGCTGCTCGCGATCGACCTGCGCGGCACGCTCGAACGACGCTTCGAGCAGCGCTTCGAATCGACGCTGCTGTTCGATC
ATCCGAGCGTGGCGGCGCTGACGGAATTCCTGCTCGGCGGCGCTGGCGGAGCAGGTGCCGCGCGCGGCGGCACCTGCTTCCTCCACGGCACATGCGGG
GCCGGCGCGCGTTGTCGAGGCCGACGCGGCGGACGCGGCCGAGCCGCATTCGCCGAAGGCGCGATCGCGGTGATCTCGATGGCTGCCGTTTCCCGGGC
GGCGCGAATTCGCCCGAGGCGTTCTGGGAGCTGCTGGCCAACGCGTCGACACGGCCGGCCCGATCCCGCCCGAGCGCTGGGACCACTCGCGCTACTACG
ACAGCGAGAAGGGCAAGCCGGGCAAGGCCTATGTCAAGGAAGGCTGCTTCGTCGACTCGGTGGACCGCTTCTATCCCGAGCGCTTCGGCATCGCCGGCAT
CGAGGCCGAGCTGATGGACCCGCAGCAGCGCATGCTGCTCGACGAGGCCTTCGAGCGCGGCGAGCGCCTGTCCGGCCTCGCTCGGCGACGCTCG
GAGACCGGCGTCTTCATGGGCGTGATGACGCAGGACTACCTGCAGCTGACCCAGCATGTGCGCGACCACGCCTTCTACGTCGGCACCGGCACTGCCAACA
GCATCGTCTCGGCCGTATCGCGCACACCTTCGGCCTGATGGGCCGGCGATGACCATCGACACCGCCTGCTCGTCCTCGCTGGTGACCGTGCAACTGGC
CTGCGAGCAGCTGCGTTCGGGCGCCTGCGATATGGCTGGCCGGCGGCGATGCGTGAGCCTGCACTCAGCCCGAGCCGCTGGTGCTCGAATGCGCGGGCGGG
ATGCTCTCGCCGACCGGGCGCTGCCGCACCTTCGACGCCGATGCCGACGGCTTCGTGCGCGGCGAGGGTTGCGGCGTGGTGGTACTCAAGCGCCTGGCCG
ACGCGGTGGCGGCCGGCGATCCGGTGGTAGCGTGATCCGCGGCGGCGCGTCGCGCACGACGGCCGCGCCGGCGGCCTGACGGTGCCCAACGGCCTGGC
GCAGCAGCGCGTGCTGGAGAAGGCGCTGGCCGACGCGGGCATCGCGCGCGAGCGCGTGTCCTATGTCGAGGCGCACGGGCACCGGCACCCATCTGGGCGAC
CCGATCGAGCTGAACGCGCTGCAGGCCGTGTATGGCCGCACGCCCGGCGAGACCAGCCTGCTGCTCGGTTCAGTCAAGACCAACATCGGCACACGCGAGG
CGGCAGCCGGCATCGCCGGGCTGATCAAGGTGCTGCTGGCGATGCGCACGAGACCCTGCCGCCGCACCTGCATTACCGGCGCGCCAATCCCAATTTCGA
CTGGACCGCCCCGCGCCTCGAGGTGGTGGGCCAGCGCCCGCGGCTGGCATGCCGGCCGCGCCGCTGGTGGCGGGCGTCAGCTCGTTCCGCCTGAGCGGCACG
AATGCGCATCTCCTGGTCGACCAGTATGTCGCGCCGGTGACGCTGCCCGACATCCGGCCGGCTTCGTGCCGCTCGGCGATGCTCTCGCAGGTCGATCGCG
CGCAGCTGGCCGCCGACGCCGAGCGTTACGCGCGGCGCTGGCCAACGGCGCCGAGCTGGCCGATCTCGCCTACACGCTGAGCGTCTCGCCGCCGCCA
CGCGTTGCAGCCGGTGCTGCCGGCCGGCTCGCTCGCGCAGCTCGCGACGCCTGCTGGCGCTGCCGCCGCCAGCACCGTCTCGGGGCTTCGAGCGGCCCGCC
GCGAGCGTGCCCCTCGAATGCCGGCTCGGCGACGGCGCGCGACCCGGTCTGGGCGCGCAGGCGGTGCATTTCTACGATCTCTACCCGGCCTTCCGCCATG
CCGTGGACGCCTGCGTCGAGGGGCTGCGCGGTCGCGGCGCGCCCGTCACGGGGCGCGCGCTGTGCCAGGGTGATGCGCCGCGTTCGAGGCGGCGAT
CCTGGTCTATGCCTTCGGGCGGCTGCTGCAGCGTCTGGGCGTGCAGCCCGAGCGGATCCGCGCGCGGCCGCTCTGCTTTGTGGCCGCCGCGCTCGGC
GGCGCGCTCGATCTCGACACCATGCTCGACGGCCTCGTGCCGAGGATGCGCGTGCCGTGCGCGCCGCGCTGGCGCAGCTGGGCCAGCGCGAGAGCGAGG
```

Fig 10B

```
TCTCGCTCGCCCTTCGAGCCGCAGCCGTCCTGGCAGGTCCAGCTGAACGAGGCGGCCGCGCTGGCCTGCCGCACGCATGCGCCCGCGCGCAAGACGACGCG
CATGCCGGCCGTGATCGACCTGCCGGCCGCTTCGCTCGACGCGCGCCCGCTGGGCGGCCTGGCCGCGCTGGTCGCCGCGCTGCCGGCGCGCGGCCAGCGC
ATCGACTGGCATGCCTATTTCGAGCCCTCGCGGGCACGCCGCATCGCGCTGCCGGCCAGCCACTTCCCGGCGCGCCGCTACTGGGTGCCGCAGACGGCGC
CCTCGACGACCCCGGCGGGCGGCCTGGTCGTCGCCGACCTGACCTCCGCGCGCGACGGCAGCCGCTATGTCGAGTTCGCACTCGATCGCGAGCGTCATCC
CTTCCTCGACGAACATCGCCTCGGCCGCGACAACGTGCTGCCCGCGGCCGGCTCGCTCGCCTTCGTGCTGCATGCGCTGGGCCGCGAGGCGCTGGCGGGC
GGCGTCACGCTCGACGAGGTGCGCTTCCTGCGGCCGCTGCGCTTCGGCGCGCGGCTCGACGTGCAGCTGGAGATCGGCGCCGACGGCCAGGCCTCGCTGC
ATGAGCGGGCCGCCTCGCTTGCCGATCGGGCGGCGCGGGCTTTCGCGACCGTCGCGAAGCTGAGCCTGGGCGGCGGCCCGACGCCGGCGCAGGCCGAACC
CTGGCTCGCCGCGCTGCGTGCCCTGCGCGAGCAGGCGCCGGCGCGTCAGGACGGCGAGGCCTTCTATCGCGATCGCCTGCCGCCGCAGCTGTGGCTCGGC
GCGGGCTACCGGCGCATCGAGGCGCTGGTCTGCGACGGCGGCCTCGCGCTGGCCGAGATCGCCACCGTCCATTCGGACTTCCTGGTCGATCCGCGCGTGC
TCGACGCCTGCCTGCAGGCCGTCAACGCGATCGACACCGGCTCGGACGAGCCGGCGGGCGCGAGCTACCTGCCTTATGCGCTGCGGCGCGTCTGGCTGGC
CGGCTGGCCCGCTGGCCGGCGCATGCGCTGCCTGGTGCGCCATCTGCCCGAGGCGGGCGCGGCCGGCGAACTGGTCTACGACCTCGCGCTGATCGACGAG
CAGGAGCGGGTGTTCGCGCTGATCGAGCACGCGCGTTTCCGCCGCGCCGCGCTGCTGGCAGTCGAGGACGAGGCCGTGCCCGCGGCGGGGCAGGACGAGG
CCGCCCGGGCTGCGCCGGCGGCGGCCGAGCCGGCGATCGCCTTGCCCGACGAGTTCGCCCAGCTGATGCCCGACGCGAAGCAGGACCTGGTCGCGCGGCT
GGTGCGCGAGCTGCTGGTGCGCTTCCTGAAGATCGACGCGGGCGCCGTGTCCGACGAGCGGCCGTTCTTCGAGCTCGGCATGGATTCGGTGTCGGCCCTC
GAATTCAGCGACGAGCTCGGCGCCTGCTTCGCGCTCGACCTGCATGTCGACACGATCTTCGACTACCCGAGCGTCGCGAGCCTGAGCGCCTACCTGCTCG
AACGGCTGGCGGCGGCACAGGCGCGGCAGGCGCCGCCGGGCCCGGCCGGGCAGGCCGCGCCGGCCGATGCCGCCTTGCCGATCGACGAACTGTCCGCGCT
GCTCAGGCAAGAGATGGGCGACGACTAA
```

Fig 10B (cont)

```
ATGGACTCGAAAGACCGCGAGCTGCTGGCCAGGCAGCCTGATCGCCATCCGCCAGGGCATCCAGAAGATCCAGGCGTTGTCGGCGCGGCTGGACCAGCCCG
TGGCGATCGTCGGGATCGGCTGCCGCGTGCCCGGTGCCGATTCCCCGAGGCGCTCTGGGAGCTGCTGCGCGATGGGCGCGAGGCGCTCGCCGAGGTGCC
GCCCGGGCGCTGGGATCTCGACGCGTATTACGACGCGACGCCGGGCACGCCCTACAAGACCTATGCGCGCCGCGCAGGCTACCTCGACGAGGTCGACCAC
TTCGACGCGCGCTTCTTCGGCATCTCGCCGCGCGAGGCGCAGCGCATGGATCCGCAGCAGCGGCTGCTGCTCGAGGTCAGCCATCGCGCGCTGGAGGATG
CCGAGCTGCCGGTCACGGCGCTGCGCGAGCAGCCGGTGGGCGTGTTCGTCGGCATCAGCTCGGGCGAATACGCGGTGATGACCCTCGACAAGGCGCGCAG
CGACAGCCAGGATGCCTGGTCGATCACAGGCACCTCGATGAATTCGGCCGCCGGCCGGCTGGCCTATCACTACGGCTTCAACGGGCCGGCACTGCCGATC
GACACGGCCTGCTCGTCCTCGCTCGTGGCGATCCACCAGGCCCTGCCGCAGCCTGCTCAACGAGGAATGCCACACCCGCTGGCCGGCGGCGTGAACTGCC
TGCTGACGCCCGAGCCCTCGATCGCGCTGGCGCAGAACAAGGTGCTCAGCGCCAGCGGGCGCTGCAGCCCGTTCAGCGCCGAGGCGACGGGCTGGTGCG
CGGCGAGGGCTGCGGAATGCTGGTGCTCAAGCGGCTCGACGACGCGCTCGCGCAGGGCTGCCGGATCCTCGCCGTGATCCGCGGCAGCCACGTGAACCAG
GATGGCGCGAGCAGCGGGCTAACGGTGCCGAACGGCTATGCGCAGCAGGCACTGATCGCCACCGCGCTCAAGCGCGCCAGGCTCGCGCCCGGCGCGATCG
GCTATGTCGAGGCGCACGGCACCGGCACCGCGCTCGGCGACCCGATCGAGATCAAGGCGCTGCAGCAGGCGCTCGGCGCCGGCCGCGAGGCCGGGCGGCC
GGTGCTGATCGGCGCGCTGAAGGCCCATATCGGCCATCTCGAGGCCGCCAGCGGCGTGGCCGGCGTGATCAAGACCGTGCTCGCGCTGCGCCATCGGCTG
CTGCCCGCGCAGATCAACCTGGGCACGCCGACCCCGCATGTCGACTGGTCCTCGGGTGGCGTCGCCGTGGTGAGCCAGTCCACGCCGATCGCCTACGGCC
CCGACGCGCCGTTCTACGCCGGTGTCAGCAGCTTCGGCTTCAGCGGCACCAATGCGCACCTGATCCTGCAGGACCCGGTCAGCGCGGTGCCGGCCCGGGC
CGAAGCCGCGGGCGCCGCGGCAACGCAGGCGGTGGCGCGTTTCGTCGGCGAAGGATCCGGCGGCGCTGCGGAGTTGCTGGCGCGCTGCCAC
GCCTATTTCCGCGAGGTGCCCGACTGGGCCGCCGCTGCGAGGCGCTCAATGCCGGGCGCGCATTACGCGCATCGCGCGGCTTCGTCGCGCGCGATC
GCGAGACGCTGCTCGAGCAGCTCGCGGCGGCGGCCGCCGAGGCGGCGCTCGAGGCCGATGCGCCGGCCGCCGACGCGGCCGCGATGGCCTGGCTGTTCAC
GGGGCAGGGCTCGCAATATGCCGGCATGGGCATCCTGTTGTACGACACGCTGCCGGCCTTCCGCGCCTGCCTCGACGCGGCCGATCGCGCGCTCGCGCCG
CATCTCGGCGAATCGGTGCTGCCCGTGATCCGCGGCGAGGCCCGCGCGCTCAACAGCACGCCCTACACGCAGCCGCGCGATCTTCGCGCCTGCAGTACGCCG
TCTCGCACACGCTGCTGGGGTTTCGGCCTGACGCCGCGCTACGTGCTCGGCCACAGCATCGGCGAGTACGCGGCGGCGGTGCTGGCCGGTGTGTTCAAACT
CGACGACGCCGCGCGCATGATCGTCCAGCGCGGCCGACTGATGGAGCAGCGCTGCGCACCGGGCGGCATGCTGGTGCTGCTGGCCGATCCGGCGCGCGCC
GCCACGCTGGCGCGTGCCCGCTGGCGGAGGCGCCACGCTGGCGGTGGCGAACGGCCCGGCCAGCCTGGTCTACGCGGGGCCGGCCGAGGCCATCGAGCGCC
TCGCGAACGCCCGCGCGAGGCGGAGGTGCGCTGCGTGCCCGCTGGCGGTCTCGACATGCCTTCCATTCGCCGATGATGGAGCCGATGCTCGCCGAGTTCGC
CGAGCTGGTGCGGCAGACGCGTTTCTCGCCGCCGCGTATCGCCTTCGTCTCGACGGCGCTGGGCCGGCTCGCCGCCGGCGAGCTGACCGATCCCGACTAC
TGGGTCGCCCATGTGCGCGAGGCGGTGCGCTTCGACGCCGCGGTGGCCGCGCTGGGCGCCGACCCGGGCTGGCGTGAGGCGCCGGCGCGGCTGGCGATCG
AGATCGGCCCCAACGAGCAACTGATCGGCATGGCGCGGCAGATGGCCGGCGCCGATGGCGCGCAGTGGCGCGGCCTGCTGCGCCGCGCGGCGACGACCAGGG
TTCGTTCGCCGAGACCCTGCGCGCCGTCTACCTGGCCGGCCTGCCGCTGCGCTGGCCGCGCGGCATGGCGCGCGACGATGCGCCCGGCCCTGCCGGGT
TACCCGTTCAGAGGCAGCGTTACTGGCTGCCCGATGCCGCGCCGCGTGCCGCGCGCGCTGCCGGCATGGTTGGCAGCCCTGAGGATCGGGAACCGGCGC
TCGATTACGCGCTCGACTGGATCGACGCGCCGGTGGCGCGCCGGCCGGGCCGCCGACCGGCCGCTGGCTTTTGTTCGCCGGCGAGGTAGCGCAAGCCGA
TGCGCTCAATGCCTCGCTCACTCCCGGCCGCGCGGCCGTGACCGTCGGCCGGTCGACGCCCGGTCGGCATCGCCGCGCTGGGCGGCGATCTGTCGAGT
TTCGACGCGGTGCTGGTATGGCCTGGCGAGCCGGCATCGACGCAGGCGCCGAGCCCGCGCGCTGGTCGCGCTGCTGGCGCTGGTCGCGGCCATCGAGG
CGATGCCCGCCGCGGCGCCCGGCGCTGCATTGCGTCGGCGAGATGGAGGCCGGCGCTTATCGGCCGCTGGCCGCAGCGCTGGCGGCGCTGTGCCGCTC
GCTGCACGAGGAGGCGCCCGAGCTGCGCCTGGGCATGATCGGCGTCGATGCCGCGCTCGATGCCCGAGGCCCGTGCCGCCGCGCTGGCCGGCGAACTGGCC
GCCGCGCGCGGCGTCGAGTCCGAGCGCTGGGTCAGCGCCGCGGGCACGCGGCTGCCGCGGCTCGTCGCCGCCACGCACTGGCGAATGTGGCCGCGCCGA
GCCTGCGCGCCGATCGCAGCTATCTGGTCACGGGCGGCACCGGCGCGCTCGGTGCGCTGTTCTCGCTGCGCTGATCGAGGCGGGCGCGCGACGTCGT
GCTCAGTTCGGCGCCGCGGCCCCGATGCCCAGCCGCCGGGCCTCCGTGCGCTGGCCGAGGCGCATGGCGCGCGCCTCAGCGTGATCGCCGCCGACCTGGCC
GATGCCGCCTCGGTCGAACGGTTGTTCGCGCAACTGGCGCCGCGAGCATGCACCGCTGGTCATGCGGCCCTGGTTCCATGCGGCCAGGTGGCCGACGCGGCC
ATGCGCGGCTCGATGCCGATGCGTTCCGCCGCGTGTTCGAGGCCAAGGTCGAGGGCGCGTGGCGGCTCGACGCGGCCGTCGCGAGCTCGAACTCGATTT
CTTCCTGATGCTGTCCTCGATCCGGGGCGTGCTCGGCGCGCCGGGGCAGGCCAACTACGCGGCCGCCAACGCCGCGCTCGACGCGCTCGCGCGCCGGCGC
CACGCCGAGGGGCGGCCCGCGCTGAGCCTGTGCCTGGGCGCGGTGGCCGGCGAGGGCATGGCGGCCGACCCACGCGCGGCGGCCACCTGCAGCGTGCCG
GCGTCGGCGCGATCGAGCCGGCGGCTACTCCCGAGCGCCGCGCGCTGGTTCGCGCAGCCGGGACCGCAAGCGATCGTGGCGGCCTTCGACTGCGCGCG
CGTGCCTGCCAATCCGCGATCCGCCGCGCGGCCCTTGCTGCAGGCCTTCGTGGCGACGTTCCCGCGCGGCGCTGCCGTTACTGCGGCCAAGCCGCCGCC
GCGCCGGCACGCGTCGTCGCCGAGGCCTCGCGCGCCAACGCCGGCCGAGACCGGCGCCTTGCTTCGCGAATCGATCGCCGAGGTGCTCGACCTGCCCGACC
CGGGCGCGATCGGCGCCCACGACACCCTGCACTCGCTCGGCATGGACTCGATCACGCTGGTCGAGTTGCGCGACCAGCTGGTGCGGCGGCTCGGCCGCGA
GCTGCCCTCGCGGCTGCTGTTCGATTTCCCGCAGGGTCGGCCAGTTGGGCCGCTACCTGGCGCTCGGCCAGCCGGAGGCGCCGCGCGCAGCGGCTCCG
GCCGCGCATGGCGCCGCCGCGCGGCCGGCCGCGAGGACATCGCCGTGATCGGCATCGGCTGCCGCTTCCCCGGCGGCATCGATTCGCGGAGACGTTCT
GGGCCGCGCTCAGGGAGAGCCGCCACCTCATCCGCGACATCGACGCCCTGCCGCGCTGCAAGTCGGCGGCGGCTGACCACCAGCG
CGCCGGCGTGCTCGACGGCTGCGAGCGCTTCGATTGCGAGCTGTTCGGCATCACGCCGCGCGAGGCGCAGTGCATGGACCCGCAGCAGCGCCTGCTGCTG
GAGACCAGCTGGGAGGCGCTCGAGCGCGCCGGCTACGATTTCGGCGCGGGCGGCACCGCCGGCGGCGTTGTTCATCGGCCCCGGCCCGAACGACTATGCGC
GCCGTTTCGCGACCGACGCCAAGGCGCTTTCGCATCACCACAGTACCGGCAACGCACTCAGCGTGACGGCCGGCCGGCTCGCCTTCGTGCTCGACTGGCA
GGGGCCGGCGCTGGCGGTCGACACCGCCTGTTCCTCGTCGATGCCCTGCACCTGGCGGTACAGGCGCTGCGCCGCGGAGTGCTCGATCGCGCTG
GCGGGCGGCGTGAACCTGCTGCTCTCGGCCGGAAACCTCGGTGCTGCTGTGAAGGGCGGGATGCTCGCGCCGACGGCCGCTGCAAGACCTCGACGCGG
CCGCCGACGGCTATGTGCGCAGCCAGGGCTGTCCGATCGTGGTGCTCAAGCGCCTGCCGACGCGCTGGCTGCCGCCGACGAGGTGCTGGCCGTCGTGCG
CGGCTCGGCCGCCAACCAGGACGGCCTACAGCCAGGGGGCTGACCGCGCGGAACGGGCAGGCGCAGCAGCGCGTGCTGCGCAACGCGCTGGCCGATGCGGCG
CTCGATCCCGCGCGGGTCGGGCTGCTGGAGGCGCACGGCACCGGCACGCCGTAGGCGACCCGATCGAGTTCGCCGCGGCGCGTGCCGTGTACGGCGAGG
CGCCCGGGCGCGAGGCGCCGCTCTGGATCGGCTCGGTCAAGACCAATCTCGGCCATGCCGAGGCGGCCGCCGGCATCGCCGGCTTCATCAAGGCGGTGCT
GTGCCTGCGCCACGAGATGATCGTCCCGCACCTGCATTTCACGCGGCTCAATCCCGAGATCGAACTCGATGAAGCCGCAATGCGGATCCCGGGCGCGACG
GCCGCCTGGCGCGTGCCGGGCGTTACGCGGCGTCAGCTCGTTCGGGTTCAGCGGCACCAACGTGCATGTGGTGCATGGAGGCGGCGCCCGCTGCGGCCG
GCGTCGAGGCACGGGAGCAGCAGCGGCACGAACAGGTACCGGTACCGGGCCGGAGCTGCCGCATCTCGCCGCCCAGCCCGGCGCGCTGCGCGCTTATCT
GCTGGCCTATCGCCACCGTCTTGCCACGCTGCCGCCGCAGCGCTACGGCGCGCTGCTCGCGGGTGCCGCGCGCCGGGCGCGGCTCGCCTGCACGCGCAGC
TTCGCCGCCGCGAACGCGGCCGAGGCGCTGGCCGCGATCGAGGCCCGCGCTCGCCGAGATGAGCCCCGAAGCCGGCGCCGGGGCGTGCGGCGAAACCGGCC
CGCGCGTCGGCGCCGATCTGCCGCGCGATGTGCCCGAGGTGCCGGTCTATCCGTTCGACCGGCAGCGCTTCTGGCTCGCGCCGCGCGGCCGAGGC
GCAGGTGGAGGCGCAGGTGGAGGCGCCCGGGCCCGCAGCGCAGCTTGGCCTGCGCCTGACGGCCAGGGACGCGCGCAGGTGATCTACGGCTCGACTAC
GCGAGCCGGCCGCCGTTCCGGCTCGACGAGCACCCTCGTGCATGGCGAGCGCGTGGTCCCGGCCGCCCGCATCTGCCGCTGATCGTCGGGATGTTGGGCG
AGCTGCGGCGGCGAGCGCGGTCGGACGCTCGCCGACGTGGTCTGCGAGACGGCGCTGGTCGTCGGCGCCGACAGCAGGCGCTGCTACGTGTCGATGC
CGAGCCCGATGCCGGCGACGGCGGCCGGCGGCCATCGCGCTCGCGGTGCTGTCGACGGCGAGGGCCGCACGCGCTGCCACCTGCGCGCGAGGCCGCGCG
CTGCCGCGCGAGGCGCAAGCGCTTGAGCCGAGCGCCGCGTGGTCGCGGTTGCGCCGGCCGGCGCGGCGCTGGCCCGCTTGACGGCGCGACCTTCTACG
ACCGCCTCTATGGGACCGAGATCGGCCTGGCCGGCGCGTTCCGCGGCGTGCTTCGATGAGCAGCACGTCGGCCAGGCGCGCGCGGAACTGGCCTGGCC
GGCTGCGGGGCAGCCGCTGGTGCCGGGCGTGCTCGACTCGCTGTTCCAGACCATCGCGCTGGCCCACGCTGGCCGACCAGCCGGGCCACAGCCACATGAAC
GGCGCGGACCATTCCGTTCGCGATCGATCCACTCGTCGTGCTGCCGCGCGCGGCATCCACGCCGGCCCGTGATCCCAATACGCGGCTCGTCAGCGAGA
GCGCCGACGGCGCGAGCTTCGTGCACGACCTGGAGGTGCCGAGGCGGGCCGGCCGCCGTTCCTGCCGTGTCGAGGGCCTGCTGACGCGACGCGCCGCCGC
```

Fig 10C

```
GGCGCAATTGCGCCGCGCGGCCGAGCCCTTGCCGCAACTGGTCGAGCACTGGGTCGAACGCCGGGTCGAGCATGAAACGGCGCCGTCCATCGCGCCGCGC
CTGGTGCTGCTCGACGAGGCGGCGCGCACGACCGCGCGATCCTGGCTGGCCGCCTCGGGCGAGGTCATCGATGCGAGCGGGCTTGACGACGCCGCCGTGC
TCGCGGCCCTGGGCAGCGAGCCGGCGGTGCTGCTGGCTGGCCTGCCGGCGGCTCCGGCGGCGGACCAGGACCTCGCGGCTGAATCCTGGCGCATGCCGCT
CCTGGGCCTGGTGGGCGCCGTGCGCGCGCCGACAGGCTCGGCGACGCGCTCGAGGCGGCGGGTGCCACGGTGCGCTTCGGCCTGCTGTCGGAGGCCCAG
GCCGATCTCGACGGGCAGGGCGGCTCGCCGCTCCATGGCTTCGCGCTCGGCCTCGCCAAGTCGCTGAGCCTCGAATGGCCGGGACGCGCCGTCACGCTGC
TCGACGTGGATGGGGAGGGCTCGCCGGCGGATGCCGCCGCGCTCGCGGCCGAATGGCGCTCGCCGCGCGGCGAGTGCATCGCCTGGCGCGGCGGCCGCCG
CCATGTGCGCCGCGTTACCGAACTCGCCGCGCCGCCGCTCGCGTCGTGGCAGCCCGCGCCGACGGCCCCTACTTGCTGACGGGCGGCCTCGGCGACCTG
GCGGCCGAGACCTGCCACTGGCTCGCCGACGAGGCGTGCGTCATGTCTGGCTGACCGGCCGTCGCGAAGCCGACGCGGCGATCGAGCGCCAGCTCGACG
CGCTGCGCGAGGCGACCGGCCTGCGCGTCGACTACCGCGCCTGCGACATCGCCGATCGCGACGCGCTCGCGGCCCTGTTCGGGATGCCGCGCGGGACGG
TCCGCTGCGCGGCATCTTCCACTGCGCGGGCGTGCTCGCCGACGGCGCCTTCGCCACGCTCGACGACGGCGCCTTCGAGCGCGTGGCGCGCGCCAAGGTG
CTCGGCAGCTGGAACCTGCACCAGCTCTCGCGCGGGCTCGATCTCGACGCCTTCGTGCTGTATTCGTCGCTGGCCTCCTTGCTGGGCTCGGCCGGGCAGG
CCAACTACGCGGCCGCCAACGGCTTCATGGATCAACTGGCGCGCTCGCGCCGCGCGCTCGGCCTGCCTGCGCTGTCGCTGAACTGGCCGGGCTGGGGCGG
CGTGGGAATGGCCGCGCGTAACGCCCGCGGCGAGCCCGGCAGCGGCCTGCGCCGGCTGGCGCCGGAGCGGGCCTCGGCGAACTGGGCCGGGCGCTGGCG
GGCGGCCAGGCCCAGGTGGGGATCGCCGATGTCGACTGGTCGGTGTTCGGCCGCGACTGGCGCGCGTCGCCGCGGCCGTGCCGGCCCTGGTGGAGGACT
GGTTCGCCGCGCATCCGCAGGCGGCGCCGCGGCAGGCGCTTGCCGCCGCCGGCGCAGTGCCCGCCGAGGCCGCCGCGAGCTTGCCGCGGCGGTGGACGT
GGACGCCCGACTCGAGATCGCGCGGCGTCACCTGGTGGGCATCGTGCGCCGGATCATGGCGCTCGACGCGGCCCGGCCGCTCGCTCAGAACAAGTCCTTC
CACGAGCTGGGTCTCGATTCGCTGATGGCCGATCGAGCTCAAGCCCGCGCTGCAGGAGGGTTTCGCCGGCCCGCGTGCCTGCCACCGTGATGTTCGACTACC
CCGATATCGACAGCCTCGCGCACTGGCTGGCGGGGCCCGCGCAGGCGGCTCGGGCCCCGGCCTCGGCTTCAGCGCCGACGCCGCGTGCCGCGCCTGCCGA
CGCGCTCGATCAACTGGACGAAGGCGAACTGGCCGACGTTCTCGACAAATTGCTGTGA
```

Fig 10C (cont)

```
ATGACGGACATGGACAAGGACCTGCTGCTGCAATCGATCCAGACGATCCGCGAACTGAAGACGCGGCTCGCGCAGGCCGAGCAAGGCCATCACGAGGCGG
TGGCGGTGGCGGTGGTCGGCGTGTCGCTGCGCTTTCCCGGAGGCGTGACCGATCTCGACAGCTACTGGGCGCTGCTGCCAGAAGGCCGCAGCGGGGTGAT
CGAGGTCGAGCCCGAACGCTGGAGCAACCGCCAGTTCGTCGATCCCGACTATGCCGCCGCCGGCAAGCTGGTGACGCCGTATGCGGGACTGCTGGAGCAC
ATCTACGATTTCGACGCCGAATTCTTCGGCCTGTCCGCGCTCGAGGCCGAGAACCTCGATCCGCAGCAGCGGCTGCTGCTGAACAGAGCTGGCTCGCGC
TCGAGGATGCCGGCTACGACATCGGCCCGGCTGCGCGGCAGCGATACCCGCGTGGTGGTGGGGATCGGCAGCCAGGATTACGGCATGGCGCTGCTGGCCGA
TCCCGCCCACGCGAATCCCTACGTCGCCTCCGGCAACTCGTTGAGCATGCCGGCCGGGCGGCTGTCCTACTTCTTCGACTTCAGCGGCCCCTCGCTGTCG
ATCGACACCGCCTGCTCGTCCTCGCTGGTGGCCGTGCACGAGGCCTGCCGGCGCCTGCAGCTGGGCGAATGCGGCCTGCCGCTGGCGGCCGGCGTCAACG
CGATGCTGACGCCGCACGCGGGCATCAACTTCTCGCGCGCACGGATGCTGAGCACCGAGCGCGACTGCCATACCTTCGACGCGCGCGCCAAGGGGTACGT
GCGCGGCGAGGGCTGCGCGGTGCTGGTGCTCAAGCGCCTGGCCGACGCGCAGGCTGACGGCGACCGCATCCACGCCGTGATCCGCGGCGTGGCGATCAAC
CACGACGGCCACAGCAGCGGCCTGACCGTGCCCAACGGTTCGGCCCAGCCGCGCGGTGATCCGCGCGGCGCTGCGGCGCGCCGGCGTGGCGCCCGCCGAGG
TCGACTACGCCGAGGCCCATGGCACCGGCACGCGGCTTGGCGATCCGATCGAGGCGCATGCGATCGCGACGTCTACGCCGAGGCGCGCGAGGCGGGCCG
CCCGCTCGTGATCGGCGCGGTGAAGGCGAACCTCGGCCATCTCGAGGCCGCGGCGGGTCTGGCCGGGTTGATCAAGGCGATGCTGGTGGTGCGCCACGGC
GAGGCGCCGCCGCAGCCCGGCTTCGAGACGCTGAATCCCGCGATCGGCTGGGATACCGCGAAGTTCAAGGTGGTGCGGCAGCCCACGCCGCTGCGGCCCG
CCGACGGGCGGCCCTGGCTGCCCGGCGTCAGCAGCTTCGGCTTCAGCGGCACCAACGCGCACGCGATCGTCGCGGCGGCGCCCTTGGCGGCCGAGGAGGG
CGAGCCGGCGGCCGAGCCGCCGGGCGGCCTGCACGTGCTCGCGCTGAGCGCGAAGACGCCCGAGGCGCTGGGTCGTCATGTCGAGGAAGTGGCCGCCTAC
CTGGCCGGCAAGCCCGCAGCCGAGCTGGCCGCGATCGCGCAAACCTCGACCTGCCGGCGCGTCGCGCTCGGCGAGCGGATCGCCGTGACCGGGCGCGACG
GCGCCGAGCTGGCCGCGCGGCTAAGGCGCGCGCTGCCGAGCGCGCGCCGCGGCGCGCCGGGCCGCATCGTGCTCTACCTGTCGAGCGCCGACCTGCC
GGCCGGCACGGCCGACCCGGCCGCCGCTGGCCGCCTTGCATCGCGGCTGGCTGGCGCGCTGCGCCGGCTTCGGCCTGTTCCCCGATCGGGTGGTGCTGCGC
GGCATCGCGCCCGCCTTCGTGCCGCGCCTGGCTCTGGCAGCATGCCGAGCCCACCGGGCTCGCCTACCTGGACGAGACGGCCGGCGACGCGTGCGGCT
TTTCCACCAGCGAGACGGCCGCCGGCGAGGTCATTGCCGCAGAGGCGGCAGCGGCCGAGCTGTTCGAGGACGCGGAGGTGCTCGCGCTCGGCGGCGCCGCC
GTTTGCCTTGCCGGCCTCGTCGTCGACCCGCTGGTTGCGCCTCGACGACGAGGCCGCACTGCGCACGACGCTTGCCGCGCTCTTCACGGCCGGCATCGAG
ATCGACTGGACGCCGCTCGATGCGCGACGCCATCGCGTGGTCCCGACTTTCCGCGCCGGCCCTTCGCACGCCCGAAGCTTCCGCTCGCCTCGCATCGACG
CGGCACTGGCCGGCGCCGACGCGCCGCGCGAGAGCGAAAGCGCGATCCATCCGCTGGTGCGCGATCGCCTGGCGCAGCCCGACGGCCGCGTGAGCTGCCG
CCTGCGCACGGCCACGGCCTGGCTCGATTTCATCGACGGCCACCGTGTGCAGGGGCATCGTCTGCTGCCGGCCTCGCTGCTGCTGAACTGATGCGCACG
GCGGCGGCCGATGCGCGCGGCGCGGCGGTGACGCTCAGCGACGCGCGCTTCCGGCGCCCCTTCGATCTCGACGCGGCCGCCTGCGATTACCTGGTCCAGG
TCGATGCCGCCGGCGAGGGCCCCCCGCTCGCTCTGTGGGGGCCGCCGCCGACGATGCGGCGAGCGCCCCTGCGTCCAACATGCGAGCGCCGCCTGCCGCT
CGCCGAGACGACGGATGCGCAGGACGCGCCGCCGGCCGAGGTCGAGGCCGAAGGCCGCGACTGGCCCGCCGAGGGCTGGCACGAACTCGATGTCGGTGCA
CTCTATGCGCGCCACCAGGCCGGCGACATCGTGCTCGGCGAGGATTTCCGCTGCCTCGCCGCCTTGCGCGTGCGGGGCGCGCGCAGCGAGGCCGAGGTCG
GCCCGCCGGGGGCGCCAGCCACGACGCGACGCAGCGTGCCGCCCTGCTGTGATCGATGCCTGCCTGCAGGCCAGCGCCGCACGCGCGAGGTCGACGACGG
CCTGTTCCTGCTCGGCCGGGGTGGGCGAGGTGGTGCTGCCGCCCCCGTGCCCTTGCCCGAGCGCCTGCGCCTGCGGCTGGTGCGCGAGGCTTGCGACCAC
GGCTATCGCTTCACGATCATGCTGGCCGATGCCGAAGGTGCGCCGGTCGGCCGGTTGCGCGAGGTGCTGTTCCGGCGCGTGCAGGGGGCACAGCGCGCCG
CGCCGTTCCACGAGACCGGCTGGGAAGCCGTCGAGTGGCCGGCGCGCGCCGCCGGCCCATGCATGCGGCGCTGCCGGCCCGGACGCGCTGGATGGGCT
CGAGGCTTCGGCCACCTGGGCCGCGCGCTTCGGGCTCGACAGCTACGACGCCTATCGCGGCAGGCCTGCGCCGGCATCGTGGCCGACACG
CTAGCCGATCTCGGGCACGACGCGCCCGACATGGAAGCCGCCGACGTCGCGCCGGCCCAGCAGCGGCTGTTCGCGCACCTGCTCGCGGTGCGCGCGCCGG
GCGACGCCGTTGCACTCGCGGCGGGCGCCGCGCGGCTCGACGGCGTCGCCGCGGCGGTTCCCACAGTTCCACGGCGAGACCGAATTCCTGCGCGCTGCGC
CGCCGCCTTGCCCGAGGTGCTGCGCGGCCGCGCAATCCGCTCGAGGTGCTGTTCGGCGGTTCCGCGTTCGACGGCAGCGAGGCCGTCTACGTCGATTCG
CCGATCGCGCGCGTGCTGAACGGCCAGCTCGCGCAATGGGCCGCGGCTCGCCGCGCAACGGCCGCTGCCATCGTCGAGATCGGCGCCGGCACGGGCCG
GCACCTCGCGCACCGTGCTCCACGCGCTGCGCGGGCCTTGCCGGTGCGCGCTACTGCTACACCGACGTCTCCCCGCTCTTCCTCGAACGCGCCGGCCGCG
CTTCGGCGAGGAGGGCTTCATCGACTACCGCCTGCTCGACATCGAGCAGCCGATCGCCGACCAGGGTTTCACGGCCGGCGAGTTCGACCTGGTGATCGCC
GCCAACGTGCTGCATGCGACGCGCTCGATCGCCGACACGCTGCCGCCAGGTGCGCGAGCTGCTGGCGCCGGGCGGCTACCTGCTGCTGCGCGAGTGCACGG
CGCAGCGCCTCAGCGCCGACCTAAGCTTCGGGATGACCGAGGGCTGGTGGCGCTTCGAGGACCACGCGCTGCGCGCCGACTACCCGGTGCTGTCGGTCGC
GCAATGGGAGCGGCAACTGGCCCTCGGCCGGCTTCGAGCATACGCTCGCCTGCCGCCGAGCGAGGCCAGCCCCGAGGCGCTGATCGTCGCGCAGGCCTCC
GCCGTCGATCGCCGCGGAGCACTGCTGGTGGTCGCACGAGGCAGGGCGTGCGTCGCCAGCTCGCGCACGAGGGGGGCTGTGCGCTGCT
CCTGGCCGGAGGCGCTGGAGGCCGATCGGCGCGCGAAAGCTACCAGCACATCGTCTGCTTCGCCGATGCCGGCGAGCCGGACAACGCCGATCCCGTCGC
GGCGGCCACCGCGCAGTACGAGGCCATGATCGCGCTGTGCCGGCGCTGGCTCGGCCCCGAGGCCGCGCCCGGCGCGCGCCTCTGGTGCGTGACGCGCAG
GCCGAGCGCGCCGTCGATGCCGACCGCGTCGACGGGCTCGGCCAGCTCGTGCCGGCCGCCGCTGCTCAAGTCCGCCGCGCGCTGGAATTCCCGCGCGTCC
CCGGCCTGGTCGATCTGGAGGCCGAGCCGGCCGATTTCGCCTCGCTCATCGCGCATTGGCGCGAGCGGGCGAGCTGCCGTCGCTGCGCGGCCGG
CCGGCCCATGGCCGCGCCTGCGGCCGCTCGATGCCGGCGCGCTCGGTGCTTCGTCGTTGGCCGGCGGCCCTGCCTTCGACGGCACGGTGCTGATCACG
GGCGGTTTCGGCGGCATCGGCCTGGCGCTGGCGGACACGCTGGCCGCGCGCGTCGAGACGCTGGTGCTGGTGGGCGCCAGGTCGGCGGTCCCGAGCGCG
AGGCGCAGCTCGCCGCGCTGCGCGAACGCGGCGCGCGCGTGATCGCGCTGGCCGCCGATCTCGCTGACGAGGCGCAGGTCGCGGGCTGTTCGCGCGGCT
GGTCGCCGAGGGCGTGGCCGGTCTCGCCACCTGATCCACGCGGCCGGGGTGGGCGGCAGCCTGGCGCTGCCGCGAGCGGGCGCGGGGAACTGCGCGAGGTG
GTCGACGCGAAGCTGGCCGGCACCTGGCATCTGCACCGGCATGCCGGCCCGTCGCTGAAGTCCTTCACCGTGCTCTCGACCATGCTCGCACTGTGGGGCG
CGCGCGAGAAGGCCCACTACACGCTGGCCAATCACTTCGCCGAGCGCGTCGTCGAATGGCGCGCGCGCGGGCTGCCGGCCTCGATCGTGCACCTGGG
CCCGATCGACGGCGGCATGCTCGACGCGGCCGGCAAGGCCGCCGCGGCGCGCGTCGGGGTGCGCAGCTTCACGCTGCGCGAGCTGGCCGGCTGGCTCGCC
GCGCCGCTGCCGCGCGCCGGCATCCGCGCTACTCGACATCGACTGGGCCCGCTTCGGCCGATCTACCGCCACGGCTGGCTCGACGCGCTGTTCGCCGAAC
TCGGCACGCCCGGCCGACGGCGGTGCGGCGCCGGTGCCAAGGCCGCGATGGCGCGGCCGCGTTCCGGCGTGCCTACGCGGCGGCTACCGCGAGTCGAT
GCTCGACGAACTGCTGCACGCGCTGCTGCGCGAGGTGCTGGGCGTGTCGGGCAACTTCGCGGCCTACGCCGGCACGGGCTTCCACGATCTCGGCATGGAT
TCGCTGCTGACCCTGTCGTTCGCCGAGAAGCTCGGCGCGCGCGTCGGCTTGCCGGTGTCCTCGGTCGACGTGTTTGACAACGCGAATCCGGCGCGCTTGC
GCGGCTGGCTCGCGGCGCGCCTGAAGGCGCTCTACGCGGCCGCGCCGGCCGCTGCCGGCAGCACCGGTAACGCTGGGGCTACTGGTGCCACCAGCGCCTT
CAGTGCCGCCGATGCCACGCATCCGGACGCGACCGACGCGCCGCCGCCCGCCGGCCCGCTGGCGCACTGTCTCCCCCACCGCGAGCGACGCCGCCGGC
GATGCCGTGACCGATGAAATCGAACGCGAGCTGCAGACGATGCAGGCGCTGCTGGAGGACCGTTGA
```

Fig 10D

```
ATGGGGAGGACCGTGGCACATTTTCTCGATCGGATCGAACAACTGTCGAAGCCGCAGTTGCAGGCGCTCGCGCGTGCGATGCGCGACGAGATCCTGCAAC
TGCGGCCCGACGAGCGGGCGGATGCCGCGCCGGCAGACATTTCAGGGCTGGCCTACGAGACGCGCTGGCAGATCGCGCCGCCGGCCCTCGCCGCGATGAA
CCCGGGCCGAGCCGGCGCGCCGCGCGTGCTGCTGCTGAATTGGCGCGACGCCGCCTGGCCGCCGGCCGGCTGCGCCGCGATCGCCTCCTGCGTGACGGCG
AGGGCGACGCTCGATCCCGACACCGGTTGGGCGCCCGAGGCACTCGCCGCGCAACTGATGCGGCTCGCGCAGGCCTCGGGGCCGTTCGACGCGATCGTGC
TTGCCGTCGGCGGCGATGCCCATGGCGCGGCGGCCCGCGGCGGAGCCGGATGCAGTGACGCTGGCCGCGCACTGGGGCACCGCGTTGGCGCTGCCCGCCGC
GGTGGCCGGCCAAGTGGCGCCGGCGCGCCTGTGGTCGTCACGCGCGGCGCCCAGTGCCTGCCCGACGATCGCCTGCCGGCCGACCCGGCGCTGGCGCCG
CTGGCCGCGCTCGGCCGCACGCTCTCGCTCGAACTCCCGGCCGCCTCGGGCGGCTGCCTCGATCTCGACGAGGCGCCCTCCTCGCTCGAACGTGCCTTCG
ACGAGATCGCCCGCGACCCGGGCGGCAGCGACGACGAAGTCGCCTATCGCGCCGGCCAGCGCTACCTGCCCGTGCTCGAACGCGTGTCCGAGGCGCCGCG
CGCGCCCTTCGTGCCCTCGTCCGAGGCCAGCTACCTGGTTACCGGCGGCACGGGCGGCATCGGCACCGTGCTGGTCGACGACCTGCTCGCGCCGGCGGCG
GGGCGCGTGGTGGTGCTCGGGCGGCGCGCCCCGCCGCGCGCCGAGGCGGCGGCATGGCTGGCCGCGCGACGGCGCGCCGGCCGGGACGAACGCGTCA
TTCTGGTCGCGGCCGATCCCGCCGACCGGGCGCGCTCGGCGCGGCGCTCGACGATATCGCCGCAGCGGCCCGCCGCTGCGCGGCATCTTCCACGCGGC
CGGCAGCAACGAACGGATCGCGCTGGCGCGCCTCACGCGCGACGACATCGCGCGCATCGTCGGCGCCAAGGCCTTCGGCGCGCTGCATCTCGATCAGCTG
ACGCGCGAGGACGCGCTCGATTTCCAGGTCTACTTTTCGTCGGTCGCCGGCCGCTGGGGCACCGCGCAGATGGCACCCTACGCGATGGCGAACCGCTTTC
TCGACGCGCTGGCCGAGCGCCGCGAGGCCGAGGGACGCCGCACGCGCAGCCTGGCCTGGGGGCCGTGGGCCGAGGTCGGCATGATGGTCCGGCAGCGGCA
GCAAGGCTTCGGCGCGCTCGGGCTGCGCGCGCTCGCGCCGGGGCTCGGGCTCGCCGCGCTGGCGCAGGCGCTCGGCCAGCCCGGCATCGCCGGCGCCACG
CGGCAGATCGTGGATGTCGATTGGCCGTGTTATGCCGAGCAGGTCGCGGTGGCCAAGCATCTGCGTCCGTTCGCTGCCCTGAGCGCCGCTGCGTCGGCGG
CTTGCGCGACGGCATCCGGTGCCGCGCCGCTCGACGCCGTGCCTTCCGCCGCCGAGGATTTCGGTCAGGCCGGGGCAACGCTGGCCCTGCTGCGCGA
ACTGGTGGCCGAGCTGACCGGCCGGCGCTGCCCGAGCGCGGCGAGCCGCGGCCGATCCAGGAACTCGGACTGACCTCGCTGCTGAGCATCGAGCTGAGC
CAGAAGCTGCGCCAGCGCCTAGGCGTGCCTTGCCGCCCGACCGTGGTGTTCGATCATGCCAACCTGCGCGCGCTGGCCGAGTCGCTGGCGCAGGCCTGGG
CGCACGCCAATCCGCGCCCGGCGGTGGCGCTCGCGCGGGTGGGCGCCGCCAGCGCCCGTGCCGCCGATGCCGACGAGGGTGCGATCGCGATCGTCGGCAT
GGCCTGCCGGCTGCCCGGCCGCCGATTCCCCTGACGCGCTGTGGGGCCAACTGATGCAGGCCGAGGCCGTCGCGCTCGACCCGGTCGAGTCGAGGCCCGCC
GCGCGCTTTGACCTCGCGCGCTACCTGTCCGACGAGGATGCGCCGGGCAAGGCCTACAGCCTCGCGGGCGGCTTCCTCGACGACTTGGAGCAGTTCGACC
ACGCGCGCTTTCGTCTTTCGCATCGCGAGGCCTGCTTCATGGACCCGCAGCAGCGGCTCGCGCTGGAGACCACCTGGCGCGCCTTCGAGGACGTCGGCAT
CGATCCCGCTGCGCGGCTCGACGGCAGCGCCGCCGACGCGCTCGACGCGGCCGTGTTCTTCGGCATCGGCCAGAACGAATACGGCCCGCTGTGCCGCTCG
GTGGCCGACGGCGAGGATGCCGGGCTGATGTCGACCGGCCAGTCGATGAACATCATCGCCGGGCGCGTCGCCCACCTGTTCGGTCTGGACGGCCCGGCGA
TCTGCCACGACACCGCCTGCTCGTCCTCGCTGGTCGCGCTCGACGCAGCGGTGCAGCACCTGCGGGGCGGCCGCAACCGGCTGCCGTGGTCGGCGGCGT
CAACGCGCTGGTCTCGCCCGACACCTTCGTGCTGCTCGGTAAGGCGCGCGCGCTGTCGCGGCAGGGCCGCTGCGCCGCGTTCGACGCACGCGCCGACGGC
TACGTGCGCGCCGAGGGCTGCGTGGTGATGGTGCTCAAGCGGCTGGCCGACGCGCCGACGGCGACGGATCCATGCCGTGATCCGCGGCAGCGCGG
TCAACCACGACGGCCGCAGCAGCGGACTGACCGCGCCGAGCGGCGCGGCCCAGGAGCGCGTGATGCGCGCCGCTGCGCGACGCCGGCGTGGCCGCGCA
CGAGGTGGCGCTGGTCGAGGCGCACGGCACCGGCACCGCGCTCGGCCACCCGATCGAATACCACGCGCTGCGCGCCGTCTACGCCGACGATGCGCCGCGC
GCCACACCGCTGGTGCTCGGCGCGCTGAAGTCTTTCATCGGCCATACCGAGGCCGCCTCGGGGCTGGCCGGCCTGCTCAAGCTGGTGCTGAGCCTGCGTG
CGGCGCATCGCGCCGCGCAGCGGCACTACGTCACGCCGAACCCGTTCATCGAGACCAGCGAGCGGATCGAGATCCCGCGTGGCGCGCGCGTCGGCGG
TGACGGGCGCGTGCTGGGCGCCGTCAGCGCTTTCGGCTTCAACGGCACCAATGCGCACGTGATCGTCGAGCGCGGCGAGGAGCGGCCCTCGCGGCGCCTG
CCCGGCGCGCCGTTCGCGCGGGTGCGCTGCTGGTACTCGGCGCGCCGCTGTCGGCCAGCAGCGGGCTCGCGCAGGCCTTCGGTGCCGCGCCGGCGAGCC
TCGCGCCGGCCAGCTACGTGACGCGCTGGGCGCCGTTCGCGGCCCCGGCCGCCGTCGCGATGCGGCAGGTGCTGGTGCTGCGCATGCCGGTCGCGGCCGG
TGATCCCCTGTACGACGCGCTGGATCGCGGCCTGATCGAGGACGATGCGCGCGCGGCGATCCGCGTGATCGAGGCCGACGGCGAGCCGGCCCCGGGCCTC
GGCCTGGCCGGCGGTGCTGGCCGCGCAGACAGCCGCGCACGGTCGCTTCGAGCGCATCGTTGCGTCTCGGCGACGGCGCCTGGCCCGACGCGGCGC
TCGACACGGCCTGGCTGGAGCGCCTCGGCCACGGCTGGTCGCGCTCGCGAGCCTGCCGGCCGAGGCCCCGCCGGTGCTCGTGAGCGGCGCCGCGCAACC
GCGCTGGCCGGCGGTGCTGGCCTGCGTCGACAAGGAGCGCGCGGGGCCGGCCCTCACCTGGCTCGACTGCGAACCGGGCCTTGGCGAGGCCGGGCTCGAC
AGCCTGCTCGACGCCCATCTCGATGCGCTGCTCGCGATCCGCGAACCGGCTTGCCGGCTCACGCGCGCGGGCCTCGTGGTGCCGCGCCTGGCCGCCGCCG
CGCCGCTGCCTCCCGCCGCGTTCCGCGCGCCGACCGCATGCCTATCTCGTCAGCGCCGGGCTCGGCGGGTCGGCCGCCGCGTGCTCGGCTGGCTGCT
CGAACAAGGCGCGTCATGTCGTCAGCCTGAACCCCGCGCGCCCATGCCGCCGAAGCAGCCGCGCTCGAGCGCCTGGCTCGACGCCACGCCGCGCGC
ATCGACACGCTGGACCTCGGCCTCGACGATCCCGAGGCCTTGCGCGAGGCGCTGCGGGCCACGCTCGGCGGCACGCCGTTGGCCGGCGTGTTCCATTGCG
CCGCCGTGCTCGACGACCAGCCGTTCGCGGCGCAGGCCTGGGACGCGGCGCGGGAGGTGCTGCGCCCAAGGGCGCCGGCGCCTGGCATCTGCACCGCGC
CACGCTGGGCCAGCCGCTCGATCACTTCGTGGTGTTCTCCTCGCTGTCGGCGCTGCTCGGCCAGCCGGGGCAAGCCGCCTACGCGCTGGCCAATGCGCTG
GCCGAGGCCGTGGTCGAACGGCGCCGCGCACTCGGCCTGCCCGCGCTGGCGATCAATGGGGGCCGTGGGCCGGCGTCGGCATGCGGCGCGCGGCGGCG
AGGCGCTGGCCGCCCAGTACCGCGCGATCGGCCTGGCCGCGCGCGGCGCCGACGACTATCTGCGCGTGCTGTCGGCGCGGCTCGCGTCCGGCGCGGGCCA
GGAAGCCTGCGTCGGCGTGTTCGATCTCGACTGGCCGCGCCATGCGGCCACCTACGCGCCGGCGCCGCTGTGGGCCGGGCTGCTGGGCGATGGCGGCGCG
CCGGCCGAGCCGCCCTCGTTCGCCGAGCGGCTCGCCGAGGTGCCGCCCGAGCGGCGCCGGCGTGCCCTGCGCGCGGGCTGCGCGAGATCGTCGCCGCCT
GCATCGGGCGCACGCCGCCGCGATCACCGATACCGACGGCTTTGCCGAGATCGGCATCGATTCGCTGCACGCCACGGTGCTGCACCGGCAGCTCGAACG
CGAATTCGGCGCCGCGCTGCCGGCCACCATCGCCTTCGATCACCCCACGGTGGCCGCCGTCGCCGACTGCCTCGCGCGGGTGCGCTGGCCGAGCTGTTC
GCGCCGGCCATCGTGGCCGCGCCGGCGCAGCTGGCGAACGCCGCGGCCGACGCATCGCTGGGGGACCACAGTGCCGCCGAACTCGCCCGGATCCTCGCGC
ACGAGCTCGGCCGTCTCGAATCACGCGGAGCACTTTGA
```

Fig 10E

```
GTGAATAAGCCCACCTCGTCCGACGGCTGGAAGGACGACTACCTGAGCCGGCTGTCGCGGCTGTCGAAGAACCAGCTGATGGCGCTCGCGCTCAAGCTCA
AGCAGCAGCAACTCGAGCAGGGGCCCGCGGCCGAGCCGATCGCGATCGTCGGCGTCGGCTGCCGGCTGCCCGGCGGCGTGGCCGGCCCGGACGACTACTG
GGCGCTGCTGCGCTCGGCCGGCAGTGGCATCGTCGAGATGCAGGACCAGCGCTGGAACATGGCCGCCTACTTCGATGCCGATCCCGAGGCGGGCGGGCGC
ATTCATACGCGTTCGCTGGGCCTGGTCGACGAGGTCGACCGCTTCGACGCCGACTTCTTCTCGATCTCGCCGCGCGAGGCCGAGTCGATGGACCCGCAGC
AGCGCCTGCTGCTGGAGGTGGCCTGGGAGGCGATCGAGCGCGCAGTGGCCACGCCTGCGCCTCGCTCGACGGGCGCCAGGTGGGCGTGTTCGTCGGCATGAT
GAACAAGGACTACCTGCACCTGAACGCGCCGGACATCACCGGCGAGGCGGCACGGCATTCGCCCTATTACGCCTCCGGCGAGGCCTTCAGCATCGCGGCC
GGACGCCTGGCCTACATCCTCGGCGTGCACGGGCCCTGCATGACGATCGACACCGCCTGCTCGTCCTCGCTGGTGGCCGTGCATCTCGCCTGCCGCAGCC
TGCTCGAGGACGAATGCGAGCTGGCGCTGGCCGGCGGCACCTCGCTGATCCTCTCGCCGGAAGCCTCGATCGTCAGCTCGAACGCGCGGATGCTGTCGCC
CACCGGGCAGTGCTGGAGCTTCGATCATCGCGCGCGACGGGTACGTGCGGCGAGGGCTGCGCCGTGGTGGTGCTCAAGCGCCTGTCGCGCGCGCTCGCC
CACGCCGACCCGGTGCTGGCCGTGATCGCCGCTCGGCCGTCAACCACGACGGCCGCAGCCAGGGGCTGACCGCGCCGAACACGGCCGCGCAGATGGCGC
TGATGCGCGAGGCCCTCCGCGGCGCGAAACTCGATGCCGCGCATCCGCTACGTGGAGGCGCACGGCACCGGCACGCCGCTGGGCGACCCGATCGAGAT
GAACTCGATCCAGGCCGTCTACGGCGAGGCGCGCGACGAGGCGTCACCGCTCGTGATCGGCTCGGTCAAGACCCAGATCGGTCACACCGAGGCCTGCGCG
CGCGTGGCCGGCCTGATCAAGCTCGCGCTGTGCGTCGCGCACGATCGCGTGGTGCCGCAGCGCAATTTCCAGCGGCGCTCAACCGCATATCACGCTGCGCG
ATGGCGTGCGGCTCGCGCTGCGCGACGAGCCGTTCGGCGGCGAGGCCGGCGCGCGCTACGGCGCCGTCAATTCCTTCGGGTTCAGCGGCACCAACGCGCA
CCTGATCGTGCGCGACCTGCCGCCCGCCGCCGGTGGCGCCCTCGCTGCGCGGGCCGGGCGTGCTGGCCGTGTCGGCCACCAACGCCGCCGCGCTCGAC
CCGCTGCTGCTGCGCTACCGCGATTACCTGGCCGCCGGGCCGGCCCCGAGCCGGACTGGGATCCGCTGGCCTATACCAGCCAGGTGGGTCGCAACCATTTCC
GCGAACGCGTGGCGCTGACGGCCGACGACATCGCCGGGCTGCCGCGCGGGCCATCGCGGCCGTGCCGCGGCCGCGACGGCGCATGA
CGAGTGGCCGCCGACCGCCCGGCGGGCTGGGTATTCGGCGTCTTCGACATGACGCCCTCGGAGTTGGTCGCGCAACTGCGGCGGAGCAGCGGCGCCTTT
CCACCGCGGTTCGACGCGCTGGTGGCGCGCCGGCGCCGGAGCTGGCGGCTCGCACGATCTGCTCGCCTACCTGACCGGCTGCGCGATCGTCGAGACCC
TGCACGACGCGGGCCTGCATGCCGACGCGCTGGCCGGTGCCGATCCGCTCGGCAGGCTGGTGGCGGCAACTGCTGCCGGCCTGGTGAGCGTCGATACCGT
GCTCGCCTGGTTGCCACTCGATGCCGCGCGCGCGACGTCGCACTGGCGATTGGCCGGCGCTGCCGCCGGAAATCGCGCTGGTCGATGCCGGCAGCGGC
CAGACCCGTCTCGATACCTGGCGCGATGCCGCGCCGCCGCGCCTGGCTCGCGCAGCCGTCGAGCCCGTGCCGGCGGCGCACCAAGGCGGGACGAGG
CGATCCGCTGGCTGGCGATCGGCGACCTGAATGCGGCGGCGGGCAAGAGCCCGGCCGCCGCGCCGTTCCTGTTCCCGCGCGAGTTCGCCTCGCGCTCCTG
GGACCCCGCCTGGGCCATGCTCTATCGCTCGGGCCTGTCGCTCGACTGGCTGCGGCGCTGTACGGCACGACGCGCTCCGCCGCGGCTGGTGTTGCCGACCTAC
GCGTTCCAGCGGCGGCGCTACTGGCCGCGCAACGCCAAGGTCGAGCAGCTCGCGGGCGCCTGCGCGCCAGCGAGCGCCGAATTCCGGCTGGTCTGGCAGC
CCGCCGCCGCGCCGGTCGACATATCGGCTTCTGGCGCGGCTCCCGCGCGGCGTCGCATCGTGCTGGCTGAACCCGGCGCCTGTCGGATGCGGCCGAGCT
GCCAGCGGGTCTGCAGTGGCTGCCGCTGCCCGAGGGCTGGCGCGACGCGCAGGTGCTGGCCGGCCTGCTCGCCTCGCTCGAACCTGGCGCCGCAGGCGCT
GCGCTCGACCTGCTGTTCTGGCTGTCGCCGTCGCGCGTCGAACGCGACGATGCCGCGCGCCGCGCGCCGACACCACGCGCGGCCTGTGCGTGATCGGCC
AGGCGCTGCTCGCGCTCGGCGAGTCGGCGGGAATGCGGATCGGTTTCGCCACCGAGGGCGTCGAGCAGGTAGTCGAGGCCGATGCGCGGCAGGCCCCGAA
CGTCGGCGATGGCGTGGTTGCCGGCTTCGTCAAGACGCTCGGCTTCGAGCAGCCGCAATGGCGTCCCTGGGTCGTCGATCTCGATGCGCGCGCTGACGGC
GCCGCGCAGATCGTGCTGGCGCTCGATGCGGCCGACGACGAGAACGATGTCGCGATTCGTGACCGGCAACGCCATGTCCGAAGGCTGGCTGCCGCGACGG
CCGATGCCGCTGACGACACCCACCACCGTCGACGCTATCGACGCAGCCAACGCCGCCGAGGCATCCAACAACGCCACCGAGGCCGCCCGCGGAGGCACCCGC
GCGCGGCGACCGCGCCTACCTGATCACCGGTGGCCTGGGCGGCATCGGGCTGGCCCTCGCCGCGCCGCCCTGGCCCGCGACGGCGCCGGCGAGCTGGTGCTG
GTATCGCGGCGCGGCCCCGAGGATGCCGAGCCCGCGCCGCGCACGACATGCTGGCCGCGGCCGGCGTGCCGCTGACCTGGGTGCGCGCCGACGTCGGCG
ACTCCGAGGCGCTGCGCGCCGGTCTCGCCGCCGTGCGCCTGCCGCTCGGCGGGATCTACCATGCGGCCGGCGTGCTCGACGACGGCCACTGCAGAACCT
GACCGACGCGCATTTCGCGCGCGTCGATGCATGCCAAGGTGGCCGGCGATGCCTGAACCTTGACCGCATCGCCCGGGAGGCCGGCGTCGAGCGCTTCGTGCTG
TTCTCCTCGGTGGCCGCGGTCGTCGGCTCGGCGGGGGCAGGCCAACTACGCGAGCGCGAACGGCTTCCTGGCCGCGCTTGGCGCGCGCGTCGCGCCGAAG
GCCTCGGCGCGACGGTGATCCACTGGGGCCCCTGGGCCGAGGCAGGCATGGCCGGCCCGGAGCGGGTGCGGCAGAAGATCGAGCGCGCCGGCTTCGTGCT
GATCGAGCCCGAGGCCGCGCTCGATGCGCTGCAGGCCGTGCTCGCGCGCGACGAGGCGCGAGGCCGTGATCGCGCGCGTTCGACTGGGCGCGATCGCCGAT
TACCTGGCCGATCGCGGCGCGCCCGCTGTTCGATCAGGTCTCGACCGCGCCGGCGCGGCCCCGGGGCGAGCGTCGAGATGCGCGGCGAGGCGCTGG
CCGATGCAGTGCGCGAGCTGCTGCAGCAGGGCGAGGCGGCCGCGGCGCGGCAGATGCAGGCCCACGCGAGGCATCGTGCGCAAGGTGCTGGCGATCGA
CGCTGGCGATGCGATCGACCCGGCGCGCTCGCTGCTCGAACTCGGCATGGATTCGCTGCTGTCGGTTGAGCTGCGCAATCGCTTCGCCGCGCAATGGGGC
CTGTCGCTGCCGGTCTCGCTGATGTTCGACTGCCCGAGCGTGGCCGCCGTGTCGGGCGCCTGCTCGACGAGCTGCGCTCGAAAGAGGGCACGGCCGCCCT
CGCGCGCCGCCGCAATCGAAATGGCAGCGGGCGCGCCGCGACGCGACGAGGCGCGCTGCGATATCGCCGTGATCGGCATGGCCTGCCGGATGCCGGCCGG
CGCGAACGATGTCGGCGCGTTCTGGGATCAACTGATCTCGGGTACCGACATGGTCCGACCGTTCGACGGCACGCGCTGGGATGTACCGCGCTTCTACACG
CCTGGCTCGACCGAGGACGGCAAGATGGTCGCCAACGACGGCGGTCAGATCGCCGACGTGCACGGCTTCGACAACCGCTTCTTCGGCATCGGCGATCGCG
AAGCCGAGTACATGGACCCGCAGCAGCGCATCGCGCTCGAGGTGGCCTCGAGGAGACCCTCGAATCGGCCGCCTACACGCCCGAGCAACTGGGCGACGGGGC
CGGCGTGTTCATCGGCCCGGGCCCGTCCGATTTCGCCGACCTGTCGCAGCGCCATGCCGGCGCTGGTCGGGCTGATGGGCCCGGCCACCACGTCAGC
GCGATACCGGGACGCATCGCGCACCTGTTCGACTGGCAGGGGCCCTGCATGGCGATCGACACCGCCTGCTCGTCCTCGCTGGTGGCAGTGCACGTGGCTG
CCCAGCACCTGCGCGAGCGCGAGTGCCGCGTCGCGCTGGCCGGCGGCGTCAACGTGATCCTCTCGCCGGCCAACAACATCGTGCTGTCGAAGGCCGGCAT
GCTGTCGCCGGCCGGCCGCTGCCGCACCTTCGATGTCGGGGCCGACGGCTACGTGCGCTCCGACGGCGTCGGGGATGGTGCTGCTCAAGCGCCTCGACGAC
GCGCTCGCCGACGGCGACGCGGATCCTCGGCGTGATCCGGCAGCGCCGTCAACCACAACGGCCGGGGCAGGGGCTCACCGCGCCGAGCAGCCGCCAGC
AGGGCGCGCCTGATCGAGGCGGCGCTGGCGCGCGCCGGACGCTGCCGTCCGAGATCCGCTACGTCGAGGCGCACGGCACCGGCACGCCGCTCGGGGATCC
GATCGAGATGGCGCATTGAAAGCCACCTACGGCGCGCATCGCGACGCGGCCGATCCGCTCTACGTGGGCGCCCTCAAGTCGGCGATCGGGCATACCGAG
AGCGCAGCCGGCGTGGCCGGGTTGATCAAGGTGCTGCTGATGATGGCGGCACCGGATGATCCCGCCCACGCTGCACCTGAACACGCTCAATCCCCACCTCG
AGATCGACCCGCGCACGATCCGCATCCCGACCGCCCCGCAGCCGTTGCTCGCGCGCGAGGACGGCACGCTGAGCTGCGCGGTCAGTCGTTCGGCTTCAG
CGGCACCAATGCGCACCTGATCGTCGCCGCGCCCGCCGGGCAAGCCGGCGCGGCCGCTCGCCGGAGTGGGCGCGGCCTGTTCGCGGTGTCGGCGCAGT
CTGCCCGCGCTGGCGCGCCTCTGCGAGCGCCATGCCGTGCATCGCATCTGGCGCGCGCCGGCACGGCCGGAGCCGCTCGCCGATCTCTGTGCGAGCACGCTGCTGG
GCCGGCGCCGCTTCGAGCACGTCCTCTGCCCTCTATCCGGACAGCCATGCCGAGCTGATCGCGCAACTGCGCGCGAGCGCGGCCGGCTGCGGCAGGCACC
GGCACCGGCGCGCCCGCCGCGATCGACACACTGGCGCTGCGCCTGGTCGCCGGTGCCGCGCTGCCCGCCGCGACGCTGGCCGGCTGGCACGACGAGCCG
CGTTTCGCCGCCGCACTCGCGGCGGCGCGCGACGCGCTGTCGGCGGCACAGGCGGGCGAGCCGGCAGGCGAGGGCGCTCCGGCCTCGCTCGACGCCGCCT
GGTTCTGCGTGCTGCATGCGCTGAGCCACTGCATGGCGCCGGTTCGGTGTCGAGCCGGACCGGATCGACTATCGCGGCCGGCTCTGGCTGGCGGCGCGCC
GATCCATCAGGCCGGTTCGCTCGACGAGGCGCGCGACCGCTTCCTGGCCGCCGATCCCGCCGCCGCCGCCCAAGCGGCTCGGCGGCATCGCGCTGCGGCCG
GCCGACCAGTGCGAAGGCGACGAAGGCGAGGGCGGCTTCCTCATGCTGCGCGACGCGAGCGGCCGCGCGACGCGCCATCTCGATGCGCGCCGGCCTCG
ACGACGAGGCCTGGCGACGCGCCTTCGGCGCGCTCTGGGAAGGAGGGCGCCGGGTGGACTGGCTGGCCGGCTTCGCCGGCTCCGCCTACCGGCGCGTGGC
CCTGCCGGCCTATCCGTTCGAGCACCGCGACTGTTCGCGGCCCCGCGGCTGCCGGCCGGCGAGCGCTCCTCGAGCTGCTGCTGGAGGATTTGCAGGCC
GAATAA
```

Fig 10F

```
GTGCCGTTGCTGTCGGCCTGCCGCGAGCTCGGAATTCTCGCCGCGCTGCAAGCGGGCCCGGTCGGCCTGACGCGGCTCGGCGCGGACCTGCGCGCGAACC
CCGGCTATCTGCGCCTGGCATTTCGCGCGCTGCACGCGCTCGACTGCGTGGCCTCGGACGATCACGAGACCTATGGGGCGACCGCGCGCTTTCGTGCCTG
CGCCGCTCTGCCCGAAGGCATCGACACGCTGTACCGGATCGACTTCGACGCCTGCCTGGGCGAAGGCACGCAGGCGACGCGGCTGGAACCCTGGTTCGCG
CTGTCGGCGCGCGGCTGGGATAGCGAGGATACCGAATGGGCGCAACTGCTCGACGGCGCATTGACGGTTCCGCTGCTGCTTGCGCTGGCCAGGCGCGGAG
TGGGGCCCGGCCAACGGAGATGACGACGCGCCGACTGGACACGCGTGTGCATCCGGCGCTGCACGCGATGCTGCCGCGACTGGCTCGCGGCGCGCCAATCGCT
CGCGCCGGCGGACGGGCTCAGGCTCAACGAGCGCGGCCGGCACCTGTGCGAGCGCGCGTTGACGATGGGCGTGACCGCCTCGTACCGGCCGATGCTGATG
GCGCTGCCCGAGCTGATCGGCGGCGATCCGCGCCGGGTGCTGACGCGCGACGCCGACGGCCACGAGACCTATGTGGACCGCACCCTCAACGTGATCGGCA
GCGGCTTCCAGCACGGCAAGTATTTCAACGACATGGCCGACCTGGTGGTCGAGCTGTTCGACCGCGAGCCGCTCGACGCGCAGCCGCGCTACATCGTCGA
CATGGGTTGCGGCGACGGCGCCCTGCTGCGCCATCTGTACAAGGCGATCGCGACGCGCTCGGCGCGCGGCCGCTGCCTCGATGGGTACCCGCTGCTGTTG
ATCGGCGCCGACTACAACCAGCGCTCGCTCGACGCCGCCGGCCGCACGCTCGAGGGCCTGCCGCACCCTTCTGGTGCATGCCGACATCGGCAAGCCGCAGG
CGCTGCTCGACGCGCTGCGCGAGCACGGCATCGACGATCCCGACGCGATCCTGCACGTGCGCTCGTTCCTCGACCACGACCGGCCGCTGGACCTGACGGC
CGAGCCGGCCGATGCGGCGCAGCCTGCCGCCGACGATCACGTCTACGTGGACGCGCGCGGCAACTGGCTGTCGCTCCGGCGCGCGTCGCGCGCGACCTGCGC
GAGCATCTTTCGCGCTGGGCCGGCATCATAGGCCGCCATGGCCTGATCGTGCTCGAGGTGTTCGCGCTGCCGGTGCGGCTCACGCGCGAGTATTTCAGCC
AGACCGAAAGCTTCAGCTTCGATTTCTATCACGCGCTGTCGCGCCAGGCGCTGGTCGACGCCGGCACCTTCCACCAGGCGCTGGCCAGCGCCGGGCTCTA
TCCGGATCGCGAATCGCTGCGCCGCTACCCGAGCGTCACGCCGTTCTCGCGGATCGTGCTGCAGCGCGTGCATCCCAAGCCGTTCACGATCCGTACCTTG
CAGTCGGACGACATCCCGGCCCTGCTCGAGATCGACGCGCGCTGCTGGCCGCAGCCGCTGCGGTTGTCGCGCGAGGCGATCGAGCAGCCGCATCGCCGTT
TCCCCGAGGGGCAGTTCGTCGTCGAATACCAAGGGCGCGGTGGTCGGCGTTCTCTACACGCAGCGCATCGACGATCTCGATGCCGTGCTGGGGCGCCGTCA
TGCCGACTACGCCGAAGCGCACGTCGCCAACGGCCGCTACTGGCAACTGATCTCGATCAGCGCGCATCCCGATTTCCCGTCGCTGGCGCTCGGCGACCAG
CTGCTCGAACACGCGCTCGACCTGGCCGCGCTGACGGCCGGCGTCGAAACGGTCTACGGCATCACGCGTTGTCTCTCTTTTATTTCGCAATCCGAAACGA
TGGAGGCCTATATCGGCCTGCGCGACGCGCACGGTCACCCCGTCGATCGCTGCTGCTTCCATCACCTGCATGGCGCCAGCATCGAGCGCGTGGTACC
GGGCGCGCGCCCCGAGGACCTCGACAACGGCGGCGACGGCGTGCTGATCCGCTACGAGCTTTCGGCGCGCTTCCGCGCGGCGGGTGCGGCGCCCTGCCG
GCGGCCGGCGATGAGTGTCGCGAGCGCGACACGCTCGAAGTCGTGTCCGAATCGGTCCGGCGCATCATGCGCGTGCCCGACAGCTTCGCGGCCGATTGCC
CGCTGCGCGAGCTGGGCCTCGATTCGATGGGGCTGATGGAGCTGCGCCTGCTGCTCGGCGCCGCGTTCTCGATCGAGTTCGATCCGGCCGCGTTCTTCAG
CTATCCACCGCGCGCGATCTATATCGACGCGCAGCGCCGGCCGGCCGATGCCGCCGCCTCGGCCTCGGTGGGCCGTGCCTCGTTCCCGGCC
CGGCCGGACGCGTCGCGGCGGGCGGATGCCTCGGCCGATTCGACGAACCCGGCGCTGCCGCCGGCACGCGCGAGACCGAGGTGGCGATCGTCGGCATCG
CGCTGCCTTTCCCGGGCGGCATCGACACGCCGCAAGCCTACTGGCGCATGCTCGACGAGGGCCGCTGCGTGATCGGCGAGCGCCCCGACACGCGCTGGCG
CGAATATCGCGAGGAGCTGGCCGCGCTGGCGCCGGCCTTGCCGCAGATCATCGCGGCGGTTTCCTGGCCGAGGTCGACCGCTTCGACGCGCGTTCTTC
CGCATCACGCGCGCGCGAGGCGCAGGCGCTCGATCCGCAGCAGCGGCTGCTGCTCGAACTGGTCTCACGAGGCCTTCGAGCAGGCCGGCATCGACGCCGACA
CGCAGGCCGGGCGCGAGGTGGGCGTGTTCCTCGGCGCCTATACGCACGACTACGAGGCGCTCGACGCTGCGCGAGCGCGCGCTCGGCGAGATCGACGCCTG
GTTCGGCTCGGGCACCGCGCTGTCCACGGCGGCCGGGCGGCTTGCCTATTGCTTCGATTTCCGCGGCCCCACGATGACGATCGACACGCCTGCTCATCC
TCCAGCAGCGCGATCTTCTCGGCTTGCCGCAGCCTGCTCGATGGCAGCGCCTCGCTGGCGGTGGCTGCCTCGGTGAACCTGATGATCGGGCCGTCGCTGA
GCGTGGCCTACGGCCGCGCGAGCATGCTCTCGCCCGACGGCCTCTGCAAGACCTTCGATGCCGGCGCGGACGGCTACGTGCCGCGGCGAGGGTGGCGTGGT
GCTGCTGCTCAAGCGCTCGACGACGCGCTGGCCGACGGCGACGCGCGTCCACGCCGTGATCAAGTCGGCCGCGCTGATGCAGGACGGCCGCACCAACGGC
CTGACCGCGCCGAACGGGCAGGCCCAGGTGGACGTGATCCGCCGCGCGCTGGCCCAGGCCGGCTGCGACCCGGCCGACATCGACTATGTCGAGGCGCACG
GCACCGGCACGCGCCTGGCGATCCGGTCGAGATCCAGGCGCTGCAGGCTTATTGCGCCGGCGCTCGAGCGTGCCGCGCCTGTCGGTCGGCTCGGT
CAAGACCAATCTCGGTCATACCGAGGCGGTCTCGGGGATGGCCGGACTGGTCAAGGTGGTGCTCTCGATGCAGCACCGCAGGGTGCCCGGCATCTGCAC
CTGAACCAGCCCAGCCGCTGCTCCGGCTCGACGAACGCAACATCGAGATCGCGCGGCAGGCTCGCGACTGGCAGGCCACGCGGGCCGCCCGCCGCCGCG
CCGGCATCAGCTCGTTCGGCTTCAGCGGCAGCAACACCCACCTGATCGTCGAGGAATTCGTGGCGCCCGAAGCCATGCCCGCGGCGCCTGTCGCGGCGCC
GCTGCCTGCGGTGGTTTCGGCCGCGACGCCGGCCGCGCTGCGCGCCAATCTCGCGGCGCTGGCCGAGTATCTCGAAGCGAGCCCGGCGCCGCTCGACCTG
GCGGCGCTCTCTCGCGCGCTGACGGCCGGGCGCGCCAGCACGCGCGTCGCGTGGCCTTCAGCTTCGATTCGAAGGAGGCGCTGCGCGAGCGTCTCGCGC
AGGCCCAGGCCGCCGTCGATCACGACGCGGCACCGCGCGCCGGCCTGCGCATCGCCTTCATGTACACCGGGCAGGGTGCTCAGTATCACGGCATGGCGCA
GCGGCTGGCCGGCACCAGCCCGGTGTTTCGTGCGCACCTGGAGCGCTGCGCGGCGCTGGTGCGTGAGCATGCCGGTTTCGACCTGTTCGACCTGATCGTGG
GGCGAGCCGCGCGCGCCATCGACGAGACGCCTACACGCAGGTCGCGCTGTTCTGCGTCGACAGCACGCTCCGCGTGCTGCTGCGGCCGGCCCAAGCGGCATCG
AGGCGAGCGTGGTGCTGGGCCACAGCGTCGGCGAATACGGCGCGGCCTGCTACGCCGGCTGTGATGGAAGAAGCCGCCACGATCCGCCTGCTGAGCCGTCG
CGGCGAGCTGATGCACGAGGGCACCGCGCGCGGCGCGATGGTCGCGCTGCTCGCCGCTCGCCGAGGTCGAGGCGCTGCTGCGCGGCTTCGACCGGCTG
GCCGTGGCCGCGCTCAACGGCCCGCGCAACCAGGTGGTGGCCGGCGATTCGCAGCAGCTCGAGGCGCTGGTGCGGCTGGCCGGCGAACGGCAGATCCCGG
CCTTCCCGCTGCCGGTCGAGCGCGCCTTCCACTCGCCGCTGATGGCGCCGATCCTGCCGGGCTTCCGCGAGCTGGCCGAGCGGCTTCGCCTATGCCGCGCC
GCGCGCGACGCTGATCTCGAACCTGACGGGCGAGGTCTGCCGGGCGCGCCCGACGCCGGCTACTGGACCGATCACATTCGCCAGCCGGTCGCGCTTCGAG
CACTCGGTGCGCACGCTGCTCGCGCAGGAGGTCGACCTGGTGATCGAGATCGGCCCGAAGCCGGTCCTCACCCGCATGGCGCAGGCCGTCGCGCCCGCGC
CGACACTGCAGTGGCTGCCGGCGCTGGTCGATGCCGAGCGCATGGCCTCGCCGCGATCTTCGCGAAGGCCAGCGAGGCGGGGCTGGCGGTGAACTGGCG
CGTCTATCCGCACGAGAGTACCGCGGCCTCGACGATTTGCCGCTGTATCGCTTCCAGCGCGAGTCGTACTGGCTGCCGGCTCTCGGCGCGCGCGGCGCG
GCACCGGCGCGGGCGCGCGAAGCCGGCGCTGCCTGCCGGATTCGCCGTCGCAGCCCGGCTCGCGCGTCGAGCCGAATGTCGATGCGGCCGCGCGTACCG
AGGTGCCCATCGATCCGGCCTGCACCCGCGCCGTGGCGCACGTGATCGGCCCGCACAGCGTGTTCCCCGCTGCCGGCTACCTCGGCTTGGCGATCGA
GGCCGCGCTGCGCTGGCTCGACCGCCCGGCCGGCGTGGTGCTGCGCGGGCTGCGTGTCGAGCAGATGCTGCGGCTGGCCGAGGACGGCGCCTACCGGCTC
GAAGCGACGGCCCGGCCGGGCGATCCGGGCGAGGGCGGCGATCCGCCGCGCCGGCGATCCTGGTGCGCAGCGCGGGCGGCACCGGCGCGCCTGGACCA
CGCATGCGCCGCACCCGAGCCGCTGGCGCGGCGGCACCGCCGCGTCGTGCTCGCGGGCCCGCCGATACGCAGGCGGTCGCGATGGACGGCGCCCTC
GTTCTACCGGCGCGTGGCCGCGCTCGGCTACGACTATGCCGCGCCGTTCCGGGCATTACCTGGCTGCCGCCGCCGGCGACAGCATCGGCGCCGACCTA
TCGGCCGCCGGCACGCCCGAGCCGGACGGCTACGGGCCGCGCCTGGCGCCTCGACCATTGCCTGCAGACCGTGCTGGCCGCGAGGCTCGAGGCGCTGG
AAGCCGATGCGCGCACCTACTGCTGCCGACCGGCGCTCGAGCGCCTGGTCTGGCACGGCGCGCTGCCGGCCGCGCCGCGCGGTGTCGCCGTGCGCGG
GCATCACGATGGCCGTCGAGGCCGAACTGCGCATCACCGACGCCAGGGCAAGCCGTGTTGCGAGATGGAGGGCCTGCCGTTTGCGCGCGGTCGATCGTCGC
GGGCTGGCCGGCGGGCGGCGCTGCCTCGGTGGTGTCGCCCGCGTCCCACCGTCGCGATCCGCCTCGCCGCTGCACGCGTGCGCTGGCGGCGCGTCG
ACCCGCCTTCGTCGCCGCCGACCAGGCCCGGCCGCTGGCTGGTCGTTACCGCCCGGCGCGTCGCCGGTGCCTTCGCCGCCGCGCTCGGCCGCGG
CGGTGCCCGCGTCGAGCGGCTCGATCCGCGACGCGCATGACGGCGGCCGGCTGGCCGCCTTCGCGCGCAGCCTGGCCGACTACGCCGGCGCGGGCC
GAGCCGTTCGGCCTGATCCATCTGCACGCGGACGCCGCCGTCGATCTCGCCGTGGTCCGTTTCCTCGCCGGCTGCCCGCCGGCTGCCTGCATCGCGCGC
TGCTGGTCACGCAGGCGCGCAGGCCGTGGCGGGCGAGTTGCCCGATCGTCGGCGACCGTGCTCTGGGGGCTCGGCGCCACGCTGCAGGCCGAGGCGCC
GCAGCAGGCGGTCACGCTGGTCGATCTGGAGGCGGGCCTCGAGCGCTGGCTCGGGATCGAGACGTGCTCAACGCCCGCGATGCCATCGACGCCGGCGC
GCGCGCGCCCCGCGTGGCCCGATCATCTCGCGCTGCGCGCGGGCCGCTGGCACCAGCGCGTGCTCGCGCCGGCCACCGCGCGGTCCGCTGACGATTT
CCGGCGACGGCAGCTACCTGGTGACGGGCGGCTGGGCGGCCTCGGCCGTCGCGTCGTCGAATTCCTGCATGCACGCGGCGCGGGCCGCATCGTCGTGCT
CGGGCGCACGCTGCCGGCCGAGCCGCCGGCCTGGCTCGCGGCGTTGCAGGCGGAACGTGCCGTTGTCGAACTGGTGGCCTGCGATCTAAGCGATGCCGCG
CGGGTCGCGAGCGTGCCGGGCACGCTGGGGCGCGAGCTGCCGCTGCGCGGCATCGTGCATGCGGCCGGGGTGCTCGACGATGCGCGCCTGATCGACCAGG
```

Fig 10G

```
ATGCGGCGCGCCTGCGGCGCGTGGCGGCGCCCAAGCTCGACGGCGCGCGCCATCTGCTGGACGCGCTGGCTGGCGCATCGCTGGCCGCGTCGCTCGATTT
CGTCTGGCTGTTCTCGTCGATCACCGCGCTGCACGGCGGCGCGGGCCAGGCCAACTACGCGGCCGCCAATGCCGCGCTCGACGGCTACGCCCACACGCTG
CGCGCACGCGGCGTGCCGGCCACCGCGATCAACTGGGGCCGTGGCGCGATACCGGGATGCTGGCGCGCGTGGCGCGGCCCGAGGCCACCTATGCGCGGC
TGCATGCCGATCCGCTCGAGCCCGCCGAGGCGGCGCGCTGGTTCGATGCGCTGCTCGCCACCGACGGCGCGCAGCTCTGCCGTGGTGCACTGGCGCCTCGA
TGCGCTGGCGCGCGTGCCGGGCCTGCCCGCGCCTGCTGCGCGACCTGGTGACGGCGCGCGACATCGGTGGCGACACCGGCCACGGCCGGGCAGGCCGGTCCC
GCGTCCTACCGGCAGCGGCTCGCCGATGCGCTGCCAGCCGAACGCGCCGCGCTGGCGCGGCGCCTGGTGGCCGAGCAGATCGCGCTGGTCACCGGCATCG
CCGCCGCGACGATCGAGCCGGCCGCGCCGCTCAGCATACTCGGCATGGATTCGCTGATGAGCGTCGCGCTCAGCGACGCGCTGGCCCACTGCCTTGGCAT
CGCCGCCTCGGCCACGCTGCTGTTCGACCACCCGACGCTCGACGCGCTGGCCCTGCACGTGCTGGCGGCCAATGCGCCCGCCGGGTCCGCCGTGGCGGAG
GCCGCGTCCGTTGCGCCGGCGGTCGAAGCCACGGAACCCGCCGCGGCCCCGCTCGATACCGAGCTCAGCGAAATCGAGGGATTGCAGGACGACGATCTGG
CCGCGCTGCTCGGCAAGGAGTTCATCCGTGAATAA
```

ANTIMICROBIAL AGENT AND METHOD FOR THE PRODUCTION THEREOF

This application is a U.S. National Stage Application of International Application No. PCT/GB2009/001972, filed Aug. 12, 2009, which claims the benefit of International Application No. 0814830.6 filed on Aug. 13, 2008; the entire contents of each application is incorporated herein by reference.

The present application relates to novel antimicrobial agents and to methods for their production, in particular to antimicrobial agents derived from *Burkholderia cepacia* complex (Bcc) bacteria.

Bacterial pathogens are prominent in many diseases and the treatment of bacterial infections has become increasingly difficult over recent years with the emergence of a number of antibiotic resistant bacterial strains. Examples include methicillin resistant *Staphylococcus aureus* (MRSA), vancomycin resistant *Enterococci* (VRE), and multidrug resistant gram negative bacteria such as *Stenotrophomonas maltophilia* and *Acinetobacter baumannii*.

In addition to the emergence of antibiotic resistant strains there are many bacterial infections that remain difficult to treat, for example, the chronic respiratory infections associated with cystic fibrosis (CF). One of the problematic pathogens associated with CF is Bcc bacteria.

Bcc bacteria are gram negative micro-organisms that normally live in the natural environment. Bcc bacteria comprise a group of closely related species which are difficult to identify to the species level without genetic tests. Currently there are 17 formally named species in the complex and various molecular methods have been developed for their identification. The epidemiology and pathogenesis of these bacteria, together with the genetic basis for their biotechnological interactions, has also been investigated in CF infection.

Patients with CF are susceptible to chronic respiratory infection with a number of bacterial pathogens. The Bcc bacteria are problematic CF pathogens because (i) they are very resistant to antibiotics, making respiratory infection difficult to treat and eradicate; (ii) infection with these bacteria is associated with high mortality in CF; (iii) they may spread from one CF patient to another, leading to considerable problems for both patients and carriers; and (iv) Bcc bacteria are difficult to identify.

There is, therefore, a need to identify new antimicrobial agents that can be used to treat bacterial infections, for example, the bacterial infections associated with CF. A need also exists for methods of identifying new antimicrobial agents that could be useful in the increasingly problematic field of treatment of bacterial infections.

SUMMARY OF THE INVENTION

According to a first aspect, there is provided an antimicrobial agent produced from a bacterium, preferably a *Burkholderia cepacia* complex (Bcc) bacterium, or a pharmaceutically acceptable salt, derivative, analogue, metabolite or prodrug thereof.

Preferably, the Bcc bacterium is selected from the group consisting of *B. cepacia, B. multivorans, B. cenocepacia, B. stabilis, B. vietnamiensis, B. dolosa, B. ambifaria, B. pyrrocinia, B. anthina, B. ubonensis, B. latens, B. diffusa, B. arboris, B. seminalis, B. metallica, B. contaminans,* and *B. lata.* (Mahenthiralingam, E., A. Baldwin, and C. G. Dowson. 2008. *Burkholderia cepacia* complex bacteria: opportunistic pathogens with important natural biology. J Appl Microbiol 104:1539-51; Vanlaere, E., J. J. Lipuma, A. Baldwin, D. Henry, E. De Brandt, E. Mahenthiralingam, D. Speert, C. Dowson, and P. Vandamme. 2008. *Burkholderia latens* sp. nov., *Burkholderia diffusa* sp. nov., *Burkholderia arboris* sp. nov., *Burkholderia seminalis* sp. nov. and *Burkholderia metallica* sp. nov., novel species within the *Burkholderia cepacia* complex. Int J Syst Evol Microbiol 58:1580-90 and Vanlaere, E., A. Baldwin, D. Gevers, D. Henry, E. De Brandt, J. J. LiPuma, E. Mahenthiralingam, D. P. Speert, C. Dowson, and P. Vandamme. 2009. Taxon K, a complex within the *Burkholderia cepacia* complex, comprises at least two novel species, *Burkholderia contaminans* sp. nov. and *Burkholderia lata* sp. nov. Int J Syst Evol Microbiol 59:102-11).

Reference strains for all these named species are freely available at the Belgium Coordinated Collection of Microorganisms (BCCM) which serves as International Depositary Authority (IDA).

Preferably, the Bcc bacterium is *B. ambifaria* strain AMMD (IDA reference number LMG 19182$^T$; see Table 1).

In another embodiment, the Bcc bacterium is *B. vietnamiensis* strain JW13.1A (IDA reference number LMG P-24642; Cardiff strain number BCC1408; Table 2).

According to further embodiments, the Bcc bacterium is selected from the group consisting of *B. vietnamiensis* LMG 18835 (strain PC259; already deposited in IDA; Table 1) *B. ambifaria* BCC0203 (LMG P-24640); *B. ambifaria* BCC0118 (LMG P-24636); *B. ambifaria* BCC1248 (LMG P-24641); *B. ambifaria* BCC0250 (LMG P-24637); *B. ambifaria* BCC1241 (LMG P-24639) and *B. vietnamiensis* BCC0268 (LMG P-24638) (Table 2).

Further provided is a Bcc bacterium selected from the group consisting of *B. vietnamiensis* strain JW13.1A (LMG-P24642), *B. ambifaria* strain BCC0203 (LMG P-24640); *B. ambifaria* strain BCC0118 (LMG P-24636); *B. ambifaria* strain BCC1248 (LMG P-24641); *B. ambifaria* strain BCC0250 (LMG P-24637); *B. ambifaria* strain BCC1241 (LMG P-24639) and *B. vietnamiensis* strain BCC0268 (LMG P-24638) or a variant or mutant thereof.

Precise identification of the antibiotic producing Bcc strains described above can be achieved using the DNA sequence-based strain and species identification approach known as Multilocus Sequence Typing (MLST; see reference Baldwin et al 2005). MLST determines the partial DNA sequence of seven genes from each Bcc strain and then assigns a Sequence Type (ST) to that strain if the combination of the seven sequences is unique. The ST of each antibiotic producing Bcc strain is given in Table 1 and Table 2. The ST of a given Bcc isolate can be determined using the methods described in two publications (see Baldwin et al, 2005; also an updated version of the MLST method by Spilker, T., A. Baldwin, A. Bumford, C. G. Dowson, E. Mahenthiralingam, and J. J. LiPuma. 2009. Expanded multilocus sequence typing for *Burkholderia* species. J Clin Microbiol 47:2607-10.). The DNA sequences of the seven MLST genes and ST of Bcc isolates can also be compared to a public database to determine if other strains match an antibiotic producing strain and are identical genetic isolates or "clones."

Preferably, the antimicrobial agent is able to inhibit the growth of gram negative bacteria, gram positive bacteria and/or fungi. In preferred embodiments, the antimicrobial agent is a broad spectrum antibiotic.

Preferably, the antimicrobial agent is able to inhibit one or more gram negative bacteria selected from the group consisting of *Burkholderia* species, *Pseudomonas* species, *Ralstonia* species, *Acinetobacter* species, *Stenotrophomonas* species, multiresistant *Escherchia coli* strains.

Preferably, the *Burkholderia* species whose growth is inhibited by the antimicrobial agents of the present invention include *B. dolosa, B. multivorans, B. anthina* and *B. pyrrocinia*. Examples of those *Pseudomonas* species whose growth is inhibited by the antimicrobial agents of the present invention include *P. putida, P. fluorescens, P. stutzeri* and *P. aeruginosa*. Preferably, the *Ralstonia* species comprise *R. mannitolytica* and *R. pickettii*. Preferably, the *Acinetobacter* species comprise multiresistant strains of *A. baumannii*. Preferably, the *Stenotrophomonas* species comprise *S. maltophilia*.

Examples of gram positive bacteria whose growth has been found to be inhibited by the antimicrobial agents of the present invention include *Staphylococcus* species, *Enterococcus* species, *Mycobacterium* species, *Bacillus* species, *Corynebacterium* species, *Micrococcus* species.

Preferably, the *Staphylococcus* species comprise *S. aureus* and methicillin resistant *S. aureus*. Preferably, the *Enterococcus* species comprise vancomycin resistant isolates. Preferably, the *Mycobacterium* species comprise *M. smegmatis. M. chelonae* and *M. abcessus*.

In preferred embodiments, the antimicrobial agent is able to inhibit the growth of one or more fungi selected from the group consisting of *Saccharomyces cerevisiae, Candida albicans* and *Basidiomycete* fungi.

According to another aspect, there is provided a compound which exhibits a carbon ($^{13}C$) NMR spectrum substantially in accordance with FIGS. 11A and 11B.

According to another aspect, there is provided a compound which exhibits a carbon ($^{13}C$) and hydrogen ($^{1}H$) NMR spectrum substantially in accordance with FIGS. 11A and 11B.

Preferably, the compound is an antimicrobial agent.

In one aspect, there is provided an antimicrobial agent comprising a compound according to the present invention.

One group of the novel Bcc antibiotics have been identified as polyketides, a class of microbial secondary metabolites from which many clinically useful antibiotics have been derived. Preferably, the antimicrobial agent is produced from a bacterium comprising a cluster of polyketide biosynthesis genes. Preferably, the antimicrobial is produced from a bacterium containing a cluster of polyketide biosynthesis genes (see FIG. 5 and the description thereof).

The genome sequence of *B. ambifaria* strain AMMD is available at the Joint Genome Institute in the USA (http://genome.jgi-psf.org/finished_microbes/buram/buram.home.html). In preferred embodiments, the cluster of polyketide biosynthesis genes is located on chromosome three of the *B. ambifaria* strain AMMD genome sequence, more preferably at nucleotides 391185 to 477601, further preferably spanning the annotated genes Bamb_5909 to Bamb_5944 (the genes, their putative functions and genomic organisation is available at the website *Burkholderia*.

Preferably, the antimicrobial agent is produced from a bacterium comprising one or more, preferably two or more, preferably three or more, preferably four or more, preferably five or more, preferable six or more genes selected from Bamb 5919 (SEQ ID NO:1), Bamb 5920 (SEQ ID NO:2), Bamb 5921 (SEQ ID NO:3), Bamb 5922 (SEQ ID NO:4), Bamb 5923 (SEQ ID NO:5), Bamb 5924 (SEQ ID NO:6) and Bamb 5925 (SEQ ID NO:7), or a fragment or nucleic acid variant thereof.

Preferably, the antimicrobial agent is produced from a bacterium comprising Bamb 5919 (SEQ ID NO:1), Bamb 5920 (SEQ ID NO:2), Bamb 5921 (SEQ ID NO:3), Bamb 5922 (SEQ ID NO:4), Bamb 5923 (SEQ ID NO:5), Bamb 5924 (SEQ ID NO:6) and Bamb 5925 (SEQ ID NO:7), or a fragment or nucleic acid variant thereof.

Preferably, the fragments or nucleic acid variants thereof comprise a nucleic acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1, 2, 3, 4, 5, 6 or 7, a nucleic acid sequence that is hybridizable thereto under stringent conditions, and/or a nucleic acid sequence that is complementary thereto.

Preferably, the fragments thereof comprise at least about 50, 75, 100, 150, 200, 225, 250, 300, 500, 750, 1000, 2000, 3000, 4000 5000 and up to at least about 7000 nucleic acids of SEQ ID NO:1, 2, 3, 4, 5, 6 or 7. Fragments may also include truncated nucleic acid molecules that have x nucleotides deleted from the 3'-terminus and/or 5'-terminus. In such truncations, x may be 1 or more (i.e. 1, 2, 3, 4, 5, 6, 7, 8, 9, 10, 15, 20, 30, 40, 50, 60, 70, 80, 90, 100, 250, 500 or more), but preferably less than 1000 nucleotides of SEQ ID NO:1, 2, 3, 4, 5, 6 or 7.

Preferably, the fragments or nucleic acid variants thereof are functional fragments or variants.

In another aspect, there is provided an antimicrobial agent produced from a bacterium comprising one or more, preferably two or more, preferably three or more, preferably four or more, preferably five or more, preferable six or more genes selected from Bamb 5919 (SEQ ID NO:1), Bamb 5920 (SEQ ID NO:2), Bamb 5921 (SEQ ID NO:3), Bamb 5922 (SEQ ID NO:4), Bamb 5923 (SEQ ID NO:5), Bamb 5924 (SEQ ID NO:6) and Bamb 5925 (SEQ ID NO:7), or a fragment or nucleic acid variant thereof.

The antibiotic biosynthesis genes in *B. ambifaria* strain AMMD produce a novel polyketide antibiotic that is highly active on multidrug resistant gram negative bacteria such as *B. multivorans, B. dolosa, B. anthina* and *B. pyrrocinia, P. putida, P. fluorescens, P. stutzeri, R. mannitolytica* and *R. pickettii, A. baumannii* and *S. maltophilia*. The antimicrobial produced by strain AMMD was originally designated "*B. ambifaria* Antimicrobial on *B. multivorans*" (BAMM). With further analysis on the type and nature of BAMM production by strains of *B. ambifaria*, the name of the antimicrobial has been changed to Ambifarin, to reflect that they are a novel class of polyketide antimicrobial produced by strains of *B. ambifaria*. Strain AMMD produces Ambifarin A, while *B. ambifaria* strain BCC0203 (LMG P-24640; Table 2) produces an even more potent polyketide of the same family that is designated Ambifarin B. Three components of the chemical structure of Ambifarin A have been determined by Nuclear Magnetic Resonance spectroscopy (NMR): a polyketide chain, a shikimate pathway derivative and an alkene side chain (see FIG. 7). This combination of chemical groups within a polyketide is novel, corroborating the unique activity of this antibiotic on other *Burkholderia* and multidrug resistant gram negative bacteria.

According to a further aspect, there is provided a compound comprising a polyketide component having the formula shown in part A of FIG. 7, wherein X is unknown, optionally a further component having the formula shown in part B of FIG. 7, wherein R is unknown, and optionally a further component having the formula shown in part C of FIG. 7, wherein X is unknown. NMR data (Nuclear Overhauser Effect or nOe) show that the two ends of the polyketide chain may circularise so that the polyketide is a cyclic component.

Using the genome sequence of *B. ambifaria* strain AMMD and specifically the sequence of the polyketide synthase (PKS) genes within antibiotic biosynthesis cluster, polymerase chain reaction (PCR) tests have been developed to identify the other *Burkholderia* strains which possess the same or closely related genes and produce a polyketide with novel antimicrobial activity (see FIG. 8).

Methods for the purification of polyketide antibiotics such as erythromycin have been developed using Amberlite anionic resins (see reference Ribeiro and Ribeiro, 2003). A method for the extraction of the Ambifarins from both agar culture and liquid culture of *B. ambifaria* has been developed using the resin Amberlite XAD-16, and represents the first time this specific Amberlite resin has been used to extract a polyketide antibiotic from a *Burkholderia* species bacterium. Crude preparations of Ambifarin made by using methanol to extract all antimicrobial substances secreted into the growth medium by *B. ambifaria* strains demonstrate both anti-gram positive, anti-gram negative (Table 1) and antifungal activity. However, when the Amberlite XAD-16 resin is used to purify Ambifarin A from a 48 hour old culture of *B. ambifaria*, the resulting preparation loses a considerable amount of its anti-gram positive and antifungal activity, but retains a potent anti-gram negative effect (see FIG. 6). This demonstrates that the Ambifarin polyketide targets multidrug resistant gram negative bacteria such as *B. multivorans* and *A. baumannii*, and is not as broad spectrum as other Bcc antibiotics described herein.

A second group of the Bcc antimicrobials are produced by strains of *B. vietnamiensis* such as strain JW13.1A (LMG-P24642; Table 2). These antibiotics have very potent activity on multidrug resistant gram positive bacteria such as MRSA and were originally designated as the *B. vietnamiensis* anti-Staphylococcal antibiotic (BVAS; see FIG. 9); to reflect their production by isolates of *B. vietnamiensis* these novel antibiotics have now been named the Vietnamycins. Unlike, the Ambifarins, the chemical composition of Vietnamycins has not yet been determined and they cannot be purified from growth media using the Amberlite XAD-16 resin (Table 2); however, extraction using methanol can be used to prepare a crude active extract of Vietnamycin. The activity of the Vietnamycin on MRSA is novel for an antibiotic compound secreted by a *Burkholderia* species bacterium.

In preferred embodiments, the antimicrobial agents of the present invention are produced from variants or mutants of the bacteria identified herein.

Preferably, the antimicrobial agent is produced via a method which comprises (i) incubating the bacterium on minimal media containing glycerol as the sole carbon source; and (ii) allowing an antimicrobial agent to accrue.

Preferably, the method further comprises (iii) isolating the antimicrobial agent.

According to another aspect, there is, therefore, provided a method for producing an antimicrobial agent, the method comprising:—

(i) culturing a bacterium on minimal media comprising glycerol as the sole carbon source; and (ii) allowing an antimicrobial agent to accrue.

Preferably, the method further comprises (iii) isolating the antimicrobial agent.

The antimicrobial agent may accrue, for example, following secretion thereof by the bacterium. As such, there is also provided a method for producing an antimicrobial agent, the method comprising:—

(i) culturing a bacterium on minimal media comprising glycerol as the sole carbon source; and (ii) allowing the bacterium to secrete an antimicrobial agent.

Preferably, the method further comprises (iii) isolating the antimicrobial agent.

In preferred embodiments, the methods further comprise converting the antimicrobial agent into a pharmaceutically acceptable salt.

Preferably, glycerol is present in an amount of between about 2 g/L and about 12 g/L, preferably between about 4 g/L and about 10 g/L, most preferably about 4 g/L.

It is preferred that the minimal media comprises yeast extract. Preferably, the yeast extract is present in an amount of between about 0.01% w/v and about 0.1% w/v, preferably between about 0.025% w/v and about 0.075% w/v, most preferably about 0.05% w/v.

Preferably, the bacterium is incubated at a temperature of between about 20° C. and about 37° C., preferably between about 28° C. and about 32° C., most preferably about 30° C. In some embodiments, the bacterium is incubated at a temperature of less than about 30° C.

Preferably, the method comprises incubating the bacterium on minimal media up to and including at least part of the stationary phase. Preferably, the method comprises incubating the bacterium on minimal media for between about 16 hours and about 120 hours, more preferably for between about 48 hours and about 96 hours, further preferably for between about 48 hours and about 72 hours. In preferred embodiments, the method comprises incubating the bacterium on minimal media for at least about 16 hours or at least about 48 hours, preferably about 48 hours.

Preferably, the minimal media is a basal salts medium (BSM). Preferably, the basal salts medium comprises the formulation originally described by Hareland et al. (1975; see reference 7). The antimicrobials are not produced when Bcc bacteria are grown on standard nutrient rich media such as Tryptic Soya Agar or Nutrient Agar. Standard minimal media such as Bushnell-Haas agar also do not support production of the antimicrobials.

Preferably, both detection of Bcc antibiotics and their extraction are carried out using a solid surface growth medium such as BSM agar. Growth in liquid media can also be used to isolate the Bcc antibiotics with cultures shaken or stirred to produce aeration during growth of the bacteria.

In preferred embodiments, step (iii) comprises extraction of the antimicrobial from the minimal media with a solvent, preferably an alcohol, more preferably methanol, an extraction method that works on all novel antibiotics described in the invention.

Preferably, the alcohol comprises between about 70% and about 90% methanol vol/vol., more preferably about 80% methanol vol/vol.

In other embodiments, the alcohol comprises about 100% methanol vol/vol.

Preferably, step (iii) comprises drying the minimal media after removal of bacteria, preferably freeze drying the minimal media.

Preferably, step (iii) comprises breaking up the minimal media, preferably by grinding, prior to extraction of the antimicrobial agent using methanol.

Preferably, an anionic resin is used to isolate the antimicrobial agent. Preferably, the anionic resin is Amberlite XAD-16.

In this respect, an anionic resin, preferably Amberlite XAD-16, can be used to isolate *Burkholderia* polyketides such as the Ambifarins. Extraction with the anionic resin may be performed directly on the supernatant of liquid cultures where the bacteria have been removed by centrifugation. From agar surface cultures of the bacteria, an aqueous extraction of the antimicrobial agent is first performed to remove the antimicrobial agent from the agar. The bacteria are grown on filters laid on the agar surface, these are then removed after growth, and the agar cut into blocks and mixed with water. The agar blocks are then removed by filtration and the anionic resin, such as Amberlite XAD-16, added to the aqueous extract to bind the antimicrobial agents. The extracted antimicrobial agent can then be eluted from the resin using a solvent, such as methanol.

According to a further aspect, there is provided an antimicrobial agent produced by a method as described above, or a pharmaceutically acceptable salt, derivative, analogue, metabolite or prodrug thereof, preferably a therapeutically acceptable amount thereof.

The antimicrobial agents of the present invention may be used in therapy. As such, there is provided a method for the treatment of a disease comprising administering to an individual suffering from a disease an antimicrobial agent as described above, or a pharmaceutically acceptable salt, derivative, analogue, metabolite or prodrug thereof, preferably a therapeutic amount thereof.

According to another aspect, there is provided a method for the treatment of a microbial infection, the method comprising administering to an individual suffering from a microbial infection a composition comprising an antimicrobial agent as defined above, or a pharmaceutically acceptable salt, derivative, analogue, metabolite or prodrug thereof, preferably a therapeutically acceptable amount thereof.

Another aspect relates to use of an antimicrobial agent as defined above, or a pharmaceutically acceptable salt, derivative, analogue, metabolite or prodrug thereof, preferably a therapeutically acceptable amount thereof, in the manufacture of a medicament for the treatment of a microbial infection.

Further provided is a compound comprising an antimicrobial agent of the invention or a pharmaceutically acceptable salt, derivative, analogue, metabolite or prodrug thereof, preferably a therapeutically acceptable amount thereof.

According to a further aspect, there is provided an antimicrobial agent as defined above, or a pharmaceutically acceptable salt, derivative, analogue, metabolite or prodrug thereof, preferably a therapeutically acceptable amount thereof, for use in therapy, preferably the treatment of a microbial infection.

Preferably, the microbial infection is selected from the group consisting of a respiratory tract infection, a digestive tract infection, a urinary tract infection, an infection of the nervous system, a blood infection, a soft tissue infection. In preferred embodiments, the microbial infection is associated with cystic fibrosis.

Also provided is a method for inhibiting the growth of a microbe, the method comprising administering to the microbe an antimicrobial agent as defined above, or a pharmaceutically acceptable salt, derivative, analogue, metabolite or prodrug thereof, or administering a bacterium capable of producing the antimicrobial agent. The method may be performed in vitro or in vivo. In the case of administering a bacterium capable of producing the antimicrobial agent, suitable conditions, such as those identified above, may be provided in order that the antimicrobial is produced.

As noted above, it is preferred that a therapeutically effective amount of the antimicrobial agent, or a pharmaceutically acceptable salt, derivative, analogue, metabolite or prodrug thereof, is present or is used in the above aspects of the invention.

A further aspect relates to a method for screening a sample for the presence of an antimicrobial producing bacterium, the method comprising:—

(i) obtaining a sample containing one or more bacteria;
(ii) culturing the sample on minimal media comprising glycerol as the sole carbon source; and
(iii) detecting the presence or absence of an antimicrobial agent produced by the bacteria.

Preferably, step (iii) comprises contacting the cultured sample with a bacterial test composition. Preferably, the bacterial test composition comprises a potentially susceptible bacterium. In preferred embodiments, the bacterial test composition comprises a soft agar. Preferably, the soft agar comprises a broth formulation and purified bacteriological agar. Preferably, the purified bacteriological agar is present in an amount of between about 0.5% w/v and about 1.0% w/v, more preferably between about 0.25% w/v and about 1% w/v, most preferably about 0.75% w/v. For example, the soft agar could be a commercially prepared soft agar such as Iso-Sensitest Broth formulation (Oxoid Ltd. Basingstoke, Hampshire, UK) with purified bacteriological agar added to 0.5% w/v.

Preferably, prior to step (iii), antimicrobial producing strains in the cultured sample are inactivated, preferably by the addition of chloroform vapour.

It will be appreciated that the preferred features of the methods described above are also applicable to the method for screening a sample for the presence of an antimicrobial producing bacteria.

According to a further aspect there is provided a kit for screening a sample for the presence of an antimicrobial producing bacterium, the kit comprising:—

(i) minimal media comprising glycerol as the sole carbon source; and
(ii) a bacterial test composition.

Example embodiments of the present invention will now be described with reference to the accompanying figures.

BRIEF DESCRIPTION OF THE DRAWINGS

FIG. 1 shows the results from screening *B. cepacia* complex bacteria for the production of antimicrobials. The first trial experiment is shown in Panel A with 18 Bcc isolates replica plated onto minimal media and allowed to grow for 5 days. This plate was overlaid with a lawn of *B. multivorans* ATCC 17616 contained in soft Isosensitest agar (the bacterial test composition; FIG. 1, Panel B). *B. multivorans* strain ATCC 17616 was selected as a test strain representative of the multidrug resistant gram negative *Burkholderia* species bacteria. Although each Bcc growth spot screened was not killed in this initial experiment (producing re-growth smears from a few isolates), a clear zone of clearing around *B. ambifaria* strain AMMD can be observed (FIG. 1, Panel B). The refined screening assay where *B. ambifaria* AMMD was killed after growth by exposure to chloroform vapour before being overlaid with *B. multivorans* ATCC 17616 is shown in FIG. 1, Panel C; the zones of *B. multivorans* growth inhibition remained clear for weeks with no detectable sign of resistant re-growth;

FIG. 2 shows the novel broad spectrum activity of Bcc antimicrobials on multiresistance pathogens. Inhibition of two different strains of methicillin resistant *Staphylococcus aureus* by the *B. vietnamiensis* strain JW13.1A antimicrobial, Vietnamycin, is shown in Panel A. Inhibition of two strains of the multiresistant gram negative pathogen, *Acinetobacter baumanni*, by *B. ambifaria* the strain AMMD antimicrobial, Ambifarin, is shown in Panel B;

FIG. 3 shows extraction and retained activity of the *B. ambifaria* Ambifarin antimicrobial using methanol to isolate all metabolites secreted by the bacterium after growth on BSM agar. *B. ambifaria* was grown as a long growth streak across the centre of the growth plate for 7 days (Panel A). The bacterial growth was then removed and the surrounding agar dried in an oven at 50° C. for 24 h (Panel B). After extraction of this dried agar with methanol and concentration of this extract by rotary evaporation, an active extract is obtained that can inhibit the growth of *B. mutlivorans* (Panel C). Performing the same extraction procedure and inhibition test on a *B. ambifaria* strain which lacked Ambifarin activity produces no antimicrobial activity against *B. multivorans* (Panel D);

FIG. 4 shows the isolation of *B. ambifaria* transposon mutants lacking Ambifarin activity. Individual transposon mutants were patched (8 per plate) on minimal media and left to grow to stationary phase to allow production of Ambifarin After chloroform killing, the mutant growth was overlaid with *B. multivorans* to reveal transposon mutants which lacked a zone of clearing and hence were not producing the Ambifarin antimicrobial. A mutant lacking Ambifarin activity is shown on the right hand panel with the remaining 15 mutants (left and right panels) all possessing wildtype levels of antimicrobial production;

FIG. 5 shows the Ambifarin polyketide biosynthesis cluster of *B. ambifaria* AMMD and associated transposon mutant insertion points. The graphic shows an Artenis screen shot of the polyketide biosynthesis gene cluster to which 8 transposon mutants lacking Ambifarin activity mapped (mutant names and locations are shown by the box arrows). Seven mutants mapped to the polyketide synthase (PKS) modular genes (mutants 9-11-5 to 20-4-6 from left to right). These PKS genes are annotated as or 0366 to or 1008 in the genome sequence of *B. ambifaria* AMMD held at the Joint Genome Institute; the annotation published on the *burkholderia* database has the same genes designated as Bamb_5919 to Bamb_5925. One mutant (20-11-1) mapped to a LuxR-type quorum sensing regulator gene shown on the left. The putative functions of pertinent genes in the polyketide biosynthesis cluster are indicated in the boxes below the screen shot. The upper panel of the graphic shows the GC content of the DNA in this region of the AMMD genome which is an average of 73% across the 66 kb PKS region; these features suggest that the antibiotic biosynthesis cluster has been recently acquired as a genomic island by *B. ambifaria;*

FIG. 6 demonstrates the activity of Ambifarin A purified from a 48 hour old liquid culture of *B. ambifaria* strain AMMD using Amberlite XAD-16 resin. After cultivation, the AMMD culture was subjected to centrifugation to remove the bacteria. The cleared supernatant containing the Ambifarin A was filtered through a glass microfiber filter and 5 g of Amberlite XAD-16 anionic resin added per 100 ml of culture fluid. The Ambifarin A was allowed to bind the Amberlite particles for 2 hours with constant stirring used to keep the resin in suspension. After binding, the resin was separated from the culture supernatant by filtration onto a glass microfiber filter, and then washed with 2 Liters of deionised water. The resin was resuspended in a small volume of water to form a slurry and poured into a chromatography column (25 mm diameter; 50 cm long) with a glass wool plug at the bottom. The resin was allowed to settle under gravity and then the water drawn off by opening the valve at the base of the column; the remaining water within the resin column was then blown out using air. The Ambifarin A was eluted from the Amerlite XAD-16 resin using methanol which was poured onto the column and allowed to drip slowly through the particles (2×50 ml methanol extractions). The methanol eluent was then concentrated using a rotary vacuum evaporator (45° C.) and finally dried down into 14 ml samples tubes. The dry weight was determined and the Ambifarin A dissolved in methanol to a concentration 5 mg/ml. 10 μg of Ambifarin A extract was then spotted onto blank antibiotic susceptibility testing disks and the methanol allowed to evaporate at 37° C. Isosensitest Agar plates were then spread with a standard inoculum (a 0.5 MacFarland standard) of fresh *B. multivorans* ATCC 17616 or *Candida albicans* SC5314, and allowed to dry. A susceptibility testing disk containing 10 μg of Ambifarin A was then placed on the agar and the plates incubated at 37° C. The zone of clearing around the disk placed on the *B. multivorans* plate (FIG. 6, panel A) demonstrates the potent activity of the Amberlite extracted Ambifarin A on gram negative bacteria. Less evidence of growth inhibition was seen with *C. albicans* (FIG. 6, panel B), indicating that the purified Ambifarin A has less activity on and toxicity towards eukarytic cells;

FIG. 7 illustrates the three components of the chemical structure of Ambifarin A which have been determined by NMR: (i) a polyketide chain (FIG. 7, panel A), (ii) a shikimate pathway derivative (FIG. 7, panel B), and (iii) an alkene side chain (FIG. 7, panel C). These three elements of the partial structure of Ambifarin A demonstrate that it is a novel polyketide antibiotic, and also does not match any known antimicrobial compound known to be secreted by a *B. cepacia* complex bacterium. NMR spectroscopy measurements were applied to Ambifarin A that had been extracted using the Amberlite XAD-16 resin as described above and then subjected to further purification by passage through Matrex 60 (35-70 micron) silica column, eluting with 0-20% methanol in ethyl acetate;

FIG. 8 demonstrates that DNA testing by polymerase chain reaction (PCR) can be used to detect polyketide synthase genes in Bcc isolates which match or are very similar to those in *B. ambifaria* AMMD which are responsible for Ambifarin A production. Three primer pairs were designed to amplify the following PKS genes from *B. ambifaria* AMMD:

(i) PKS gene Bamb_5925 (or 1008), forward primer (F5925) 5'-GCTGGGATAGCGAGGATACC-3') (SEQ ID NO:8) and reverse primer (R5925) 5'-CAGAAGATCCAGGCGTTGTC-3') (SEQ ID NO:9) amplifying a 415 bp product;
(ii) PKS gene Bamb_5921 (or 0568), forward primer (F5921) 5'-AACGTGCCTTCGACGAGAT-3' (SEQ ID NO:10) and reverse primer (R5921) 5'-CCGTTGAAGCCGTAGTGATA-3' (SEQ ID NO:11) amplifying a 524 bp product;
(iii) PKS gene Bamb_5919 (or 0366) forward primer (F5919) 5'-GGCGTGAACCTGATCCTTT-3' (SEQ ID NO:12) and reverse primer (R5919) 5'-AATCTGCGGATTGAGGGTCT-3' (SEQ ID NO:13) amplifying a 555 bp product.

Standard PCR at an annealing temperature of 55° C. was performed using QIAGEN reagents (QIAGEN, UK Ltd.) in a 25 μl volume with 10 pmol of each oligonucleotide primer and approximately 100 ng of template DNA from *B. ambifaria* strains. PCR products were then separated by agarose gel electrophoresis, detected by staining (SafeView) and photographed to produce image shown in FIG. 8. All the *B. ambifaria* strains tested in FIG. 8 possess anti-gram negative antibiotic activity (see Table 4) and all test positive for the PCR detecting Bamb_5921 gene. Slight variation in the size of the PCR product around the expected 524 bp product produced by amplification of the *B. ambifaria* AMMD positive control (see arrow and dashed line in FIG. 8) indicate that the corresponding PKS gene in each *B. ambifaria* strain may have minor variations in its gene sequence compared to strain AMMD. For example strain BCC0203 (LMG P-24640) has a slightly larger PCR product, while strain BCC0250 (LMG P-24637) has a slightly smaller PCR product. This variation in the DNA sequence of the PKS gene may produce variations in the protein sequence of each PKS enzyme, and hence ultimately produce a polyketide antibiotic with a slightly different structure and activity to the Ambifarin A produced by *B. ambifaria* strain AMMD. However, these PCR tests provide a useful means to identify *B. ambifaria* strains with polyketide-based antimicrobial activity as described in the invention;

FIG. 9 shows growth inhibition of methicillin resistant *Staphylococcus aureus* (MRSA) by the *B. vietnamiensis* strain JW13.1A antibiotic, Vietnamycin, in comparison to the mupirocin producing bacterium *Pseudomonas fluorescens* strain NCIMB 10856. Mupirocin (Pseudomonic acid A, or Bactroban) is the frontline topical antibiotic used to combat skin infections with gram positive bacteria and is also used in the eradication of MRSA from infected people. It was originally produced as Bactroban by GlaxoSmithKline, but now it is available generically within a number of different commercial formulations. MRSA strain 52 is susceptible to both the *P. fluorescens* mupirocin (Panel A) and Vietnamycin (BVAS; Panel B). However, MRSA strain 49 is representative of a number of emerging *S. aureus* strains that are resistant to mupirocin (Panel C). However, the *B. vietnamiensis* JW13.1A antibiotic retains it antimicrobial activity against this mupirocin resistant *S. aureus* strain (Panel D). These data demonstrate that the Vietnamycin antimicrobial described herein is a novel antibiotic that differs from mupirocin in that it can overcome emerging resistance and prevent growth of MRSA strains that have become mupirocin resistant;

FIGS. 10A to 10G show the nucleotide sequences of Bamb 5919 (SEQ ID NO:1) (FIG. 10A), Bamb 5920 (SEQ ID NO:2) (FIG. 10B), Bamb 5921 (SEQ ID NO:3) (FIG. 10C), Bamb 5922 (SEQ ID NO:4) (FIG. 10D), Bamb 5923 (SEQ ID NO:5) (FIG. 10E), Bamb 5924 (SEQ ID NO:6) (FIG. 10F) and Bamb 5925 (SEQ ID NO:7) (FIG. 10G); and FIGS. 11A and 11B show $^{13}C$ (100 MHz) and $^{1}H$ (500 MHz) NMR spectrum for Ambifarin A in MeOD-$d_4$.

DETAILED DESCRIPTION OF THE INVENTION

The invention relates to novel antimicrobials and methods for their production. The invention also relates to uses of the antimicrobials for the treatment of microbial infections. Further disclosed are methods and kits for screening bacterial samples for antimicrobial producing bacteria.

Within this specification, the terms "comprises" and "comprising" are interpreted to mean "includes, among other things". These terms are not intended to be construed as "consists of only".

Within this specification, the term "antimicrobial" includes antibiotics and chemicals capable of inhibiting the growth of bacteria or capable of killing bacteria. An example of an antimicrobial chemical is a disinfectant.

Within this specification, the term "antibiotic" means an agent produced by a living organism, such as a bacterium, that is capable of inhibiting the growth of another living organism, for example another bacterium, or is capable of killing another living organism, for example another bacterium.

Within this specification, the term "therapeutically effective amount" means an amount of an agent or compound which provides a therapeutic benefit in the treatment of a microbial infection.

Within this specification, the term "pharmaceutically acceptable salt" means a salt of an antimicrobial agent or compound, for example that is safe and effective for use in the treatment of a disease.

Suitable pharmaceutically acceptable salts may include acid addition salts which may, for example, be formed by mixing a solution of the antimicrobial agent with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the antimicrobial agents of the invention carry an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), pahnitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylat, triethiodide, undecanoate, valerate, and the like.

Within this specification, the term "derivative" means a compound derived from or obtained from an antimicrobial agent of the present invention.

Within this specification, the term "analogue" means a compound that is structurally similar to an antimicrobial agent of the present invention.

Within this specification, the term "metabolite" means any intermediate or product resulting from metabolism of an antimicrobial agent of the present invention.

Within this specification, the term "prodrug" means a functional derivative of an antimicrobial agent of the present invention that is readily convertible in vivo into the required antimicrobial agent.

Within this specification, the term "variant" includes, but is not limited to, a bacterial strain that differs from the specified bacterial strain but which is able to produce the same antimicrobial agent according to the methods described herein. This term can also mean a bacterial strain that differs from the specified bacterial strain but which retains sufficient genotypic or phenotypic characteristics to maintain a taxonomic similarity.

Within this specification, the term "mutant" includes, but is not limited to, a bacterial strain that has arisen as a result of a mutation of the specified bacterial strain but which is able to produce the same antimicrobial agent according to the methods described herein. This term can also mean a bacterial strain that differs from the specified bacterial strain as a result of a mutation, for example an altered gene, DNA sequence, enzyme, cell structure, etc.

Such mutants can be produced in a manner known in the art, for example by physical means such as irradiation (for example UV), by exposure to chemical mutagens or by genetic manipulation of DNA of the bacterium. Methods for screening for mutants and isolating mutants will be known to a person skilled in the art.

Figure 3:
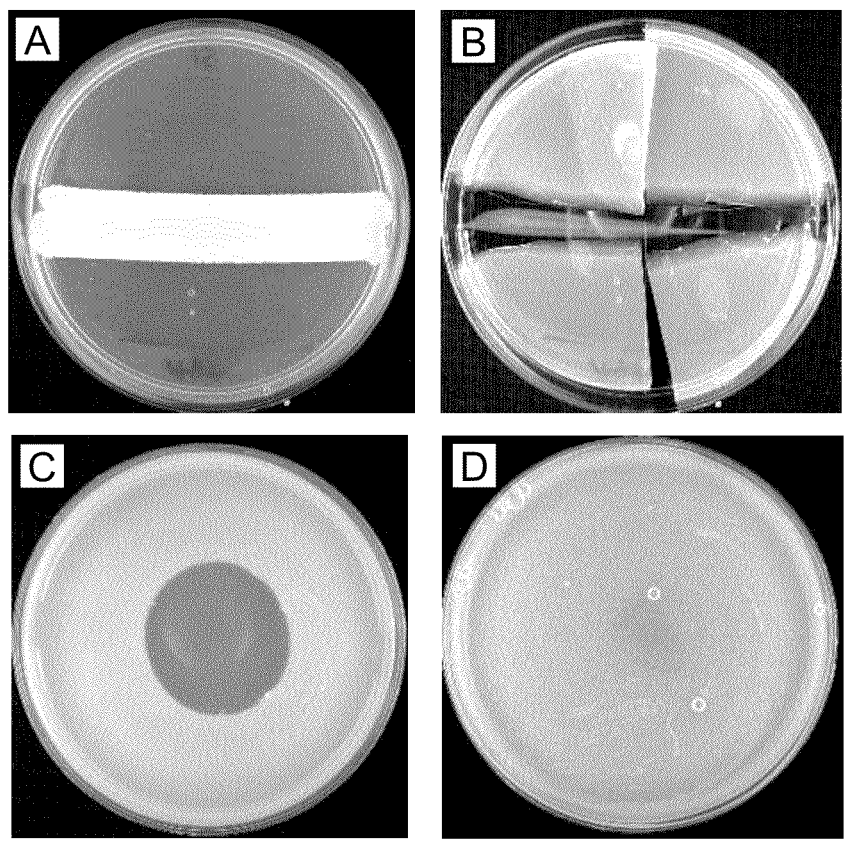

Within this specification, the term "about" means plus or minus 20%, more preferably plus or minus 10%, even more preferably plus or minus 5%, most preferably plus or minus 2%.

Within this specification, the term "broad spectrum antibiotic" means an antimicrobial that is effective against both gram-positive and gram-negative bacteria.

Within this specification, the term "minimal media" means media containing the minimum nutrients possible for colony growth.

Antimicrobial agents of the invention can be incorporated into pharmaceutical compositions suitable for administration. Such compositions typically comprise at least one antimicrobial of the invention and at least one pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., an antimicrobial according to an embodiment of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds can be formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

An example of a suitable dosage could be up to about 500 mg per day of the active ingredient for tablets.

Within this specification, the abbreviation "LMG" refers to Laboratorium voor Microbiologic, Universiteit Gent and is used in relation to accession numbers for microorganisms deposited at the Belgian Coordinated Collection of Microorganisms (BCCM) held at the LMG.

Within this specification, the abbreviation "ATCC" refers to the American Type Culture Collection biological resource centre and is used in relation to accession numbers for microorganisms deposited at this depository.

Within this specification, the term "potentially susceptible bacteria" means bacteria which have the potential for their growth to be inhibited by an antimicrobial agent produced by an antimicrobial producing bacterium. Examples include those listed herein whose growth may be inhibited by the antimicrobial agents of the present invention.

Within this specification, the term "invention" should be construed with reference to the claimed subject matter.

Within this specification, "identity," as it is known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. Percentage identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988), all of which are incorporated herein by reference in their entirety. Preferred methods to determine identity are designed to give the largest match between the sequences tested. Methods to determine identity are codified in publicly available computer programs. Preferred computer program methods to determine percentage identity between two sequences include, but are not limited to, the GCG program package (Devereux, J., et al., Nucleic Acids Research 12(1): 387 (1984), which is incorporated herein by reference in its entirety), BLASTP, BLASTN, and FASTA (Atschul, S. F. et al., J. Molec. Biol. 215: 403-410 (1990), which is incorporated herein by reference in its entirety). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990), which is incorporated herein by reference in its entirety). As an illustration, by a polynucleotide having a nucleotide sequence having at least, for example, 95% "identity" to a reference nucleotide sequence of "SEQ ID NO: A" it is intended that the nucleotide sequence of the polynucleotide is identical to the reference sequence except that the polynucleotide sequence may include up to five point mutations per each 100 nucleotides of the reference nucleotide sequence of "SEQ ID NO: A." In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of "SEQ ID NO:B" is intended that the amino acid sequence of the polypeptide is identical to the reference sequence except that the polypeptide sequence may include up to five amino acid alterations per each 100 amino acids of the reference amino acid of "SEQ ID NO: B." In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As used herein, the term "hybridizes under stringent conditions" is intended to describe conditions for hybridization and washing under which nucleotide sequences encoding a receptor at least 50% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in Current Protocols in Molecular Biology, John Wiley & Sons, N.Y. (1989), 6. 3.1-6.3.6, which is incorporated herein by reference in its entirety. One example of stringent hybridization conditions are hybridization in 6× sodium chloride/sodium citrate (SSC) at about 45° C., followed by one or more washes in 0.2×SSC, 0.1% SDS at 50-65° C. In one embodiment, an isolated receptor nucleic acid molecule that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

BSM minimal media can be made using the following stock solutions: Phosphate Salts (20× stock comprising di-potassium Hydrogen Orthophosphate Trihydrate [$K_2HPO_4.3H_2O$] 85 g/l and Sodium-di-Hydrogen Orthophosphate Monohydrate [$NaH_2PO_4.H_2O$] 20 g/l); Ammonium Chloride (20× stock comprising $NH_4Cl$ 40 g/l); Nitrilotriacetic Acid (100× stock comprising $C_6H_9NO_6$ at 10 g/l); Metal Salts (100× stock comprising Magnesium Sulphate Heptahydrate [$MgSO_4.7H_2O$] 20 g/l, Ferrous Sulphate Heptahydrate [$FeSO_4.7H_2O$] 1.2 g/l, Manganese Sulphate monohydrate [$MnSO_4.H_2O$] 0.3 g/l, Zinc Sulphate Heptahydrate [$ZnSO_4.7H_2O$] 0.3 g/l, Cobalt Sulphate Heptahydrate [$CoSO_4.7H_2O$] 0.1 g/l). The stocks are combined as follows: 50 ml Phosphate stock, 50 ml Ammonium chloride stock, 10 ml Nitrilotriacetic aci stock, 10 ml Metal Salts, and made up to 900 ml with deionised water. Glycerol (4 g), yeast extract (0.5 g) and purified bacteriological agar (15 g) are then added to this mixture before the medium is made to a final volume of 1 liter and sterilised by autoclaving and poured into culture plates.

Within this specification embodiments have been described in a way which enables a clear and concise specification to be written, but it is intended and will be appreciated that embodiments may be variously combined or separated without parting from the invention.

Example 1

The Cardiff Bcc collection was screened for the production of antimicrobials capable of inhibiting the growth of four bacterial species:
  (i) *B. cenocepacia* as a representative dominant Bcc CF species (11);
  (ii) *B. multivorans* as the most dominant Bcc CF species now seen in the UK CF population (5);
  (iii) *Pseudomonas aeruginosa* as the major CF pathogen (5); and
  (iv) *Staphylococcus aureus*, as a representative gram positive CF infection (5).

A trial experiment was performed, where 18 Bcc isolates representative of the current species as well as genome reference strains were examined for antimicrobial production. This involved inoculating Bcc isolates onto minimal media containing different carbon sources, leaving them to grow at 30° C. until stationary phase, and then overlaying them with soft-agar containing one of the four test susceptibility species listed above. The very first experiment (FIG. 1, panel A and B) demonstrated that *B. ambifaria* strain AMMD, was secreting an antimicrobial compound that inhibited the growth of *B. multivorans* ATCC 17616 producing a zone of clearing in the soft-agar overlay. The production of the antimicrobial only occurred on minimal media containing glycerol as the sole carbon source. The initial experiment was subsequently repeated and refined by chloroform vapour killing the antimicrobial producing strains prior to overlaying with the susceptibility test organism; these changes clearly demonstrated antimicrobial production by *B. ambifaria* strain AMMD (FIG. 1, panel C).

Example 2

A collection of 267 genetically distinct Bcc strains (Table 3) was screened using the methods described above. The ability to inhibit *B. multivorans*, *P. aeruginosa* and *S. aureus* was examined; no inhibition of *B. cenocepacia* had been seen in other trial experiments, therefore susceptibility of this organism was not explored further. The results of this screen were staggering, with over 40% (109 strains) of the Bcc bacteria screened demonstrating antibacterial activity in the form of a zone of clearing of the test susceptibility species (Tables 1, 2 and 3; FIG. 1). All Bcc strains described herein with antimicrobial activity can be specifically identified using MLST (1) and their specific ST is reported in Tables 1 and 2.

Two strains with significant novel antimicrobial activity described here are well studied *B. cepacia* complex isolates that already been submitted to an IDA as part of ongoing research on these bacteria (*B. ambifaria* AMMD [LMG 19182$^T$] and *B. vietnamiensis* PC259 [LMG 18835]; Table 1); their antibacterial activity has not been demonstrated before but they are already available for public examination as reference isolates from the Belgium Coordinated Collection of Microorganisms. Novel antibacterial activity has also been demonstrated for 13 other strains which are available for public examination as *B. cepacia* complex reference isolates (Table 1).

Seven further strains with potent anti-gram positive or anti-gram negative activity have been submitted to an IDA under the Budapest Treaty as part of this patent application (*B. ambifaria* BCC0203, BCC0118, BCC1248, BCC0250 and BCC1241, and *B. vietnamiensis* BCC0268 and BCC1408; Table 2).

TABLE 1

*Burkholderia cepacia* complex antimicrobial producer strains held in an International Depository (IDA) and fre TABLE 1-continued Burkholderia cepacia complex antimicrobial producer strains held in an International Depository (IDA) and freely available to the public as reference isolates

| Strain name (as submitted to IDA) | IDA strain name | B. cepacia complex species | Other names (including names held under at other IDAs or researcher collections) | MLST sequence type: | Anti-gram negative | Anti-gram positive | Source and further information |
|---|---|---|---|---|---|---|---|
| ATCC 49709 | ATCC 49709 | B. cepacia | RIMD 1622001; Sneath D335; Stanier 382; USCC 2039; BCC0002 ATCC 49709; RJ2; BCC0196 | 11 | No | Yes | Grass seed isolate and biological control strain |
| J2315 | LMG 16656 | B. cenocepacia | ATCC BAA-245; CCM 4899; CCUG 48434; Govan J2315; NCTC 13227; strain CF5610 | 28 | No | Yes | Cystic fibrosis isolate from the United Kingdom. Isolate is part of a published panel of strains that span the diversity of B. cepacia complex species (see Mahenthiralingam et al. 2000). Genome sequence of the strain has been determined at the Sanger Institute (see http://www.sanger.ac.uk/Projects/B_cenocepacia) |
| ATCC 25609 | ATCC 25609 | B. cenocepacia | ATCC 25609; NCDC A977 (EO-1 group); NCTC 10744; BCC0168; | 331 | No | Yes | Clinical infection from the United States of America |
| ATCC 25416 | LMG 1222$^T$ | B. cepacia | ATCC 25416; Ballard 717; Burkholder 717; CCEB 669; CCUG 12691; CCUG 13226; CIP 80.24; CNCTC Ps 156/77; DSM 7288; FIRDI 735; ICMP 5796; ICPB PC25; IFO 14074; JCM 5964; Kosako 85005; NCTC 10743; Palleroni # 717; PDDCC 5796; RH 2796; BCC0001 | 10 | No | Yes | Onion isolate that is the Type strain for the species B. cepacia |

TABLE 2

Burkholderia cepacia complex antimicrobial producer strains held in an International Depository (IDA) under the Budapest Treaty

| Strain name (as submitted to IDA) | IDA strain name | B. cepacia complex species | Other names | MLST sequence type: | Anti-gram negative | Anti-gram positive | Purification on Amberlite XAD-16 resin |
|---|---|---|---|---|---|---|---|
| BCC0203 | LMG P-24640 | B. ambifaria | BCF | 165 | Yes | Yes | Yes |
| BCC0118 | LMG P-24636 | B. ambifaria | JLO | 76 | Yes | Yes | Yes |
| BCC1248 | LMG P-24641 | B. ambifaria | KWO-1 | 385 | Yes | Weak | Yes |
| BCC0250 | LMG P-24637 | B. ambifaria | WM2 | 81 | Yes | Yes | Yes |
| BCC0268 | LMG P-24638 | B. vietnamiensis | BBG1222 | 62 | No | Yes | No |
| BCC1408 | LMG P-24642 | B. vietnamiensis | JW13.1A | 200 | No | Yes | No |
| BCC1241 | LMG P-24639 | B. ambifaria | KC311-6 | 396 | Yes | Yes | Yes |

TABLE 3

Summary of production of antimicrobials by B. cepacia complex bacteria

| B. cepacia complex species or group | Total No. of strains screened[a] | % strains inhibiting B. multivorans[b] | % strains inhibiting S. aureus[b] | % strains inhibiting P. aeruginosa[b] |
|---|---|---|---|---|
| B. ambifaria | 45 | 24.4 | 46.7 | 2.2 (1 strain) |
| B. pyrrocinia | 16 | 0 | 12.5 | 0 |
| B. anthina | 14 | 0 | 7.1 | 0 |
| Novel BCC[c] | 24 | 0 | 12.5 | 0 |
| B. cepacia | 30 | 0 | 56.7 | 0 |
| Group K[c] | 16 | 0 | 6.3 | 0 |
| B. cenocepacia IIIA | 28 | 0 | 53.6 | 0 |
| B. cenocepacia IIIB | 30 | 13.3 | 23.3 | 0 |
| B. dolosa | 8 | 0 | 0 | 0 |
| B. multivorans | 24 | 0 | 0 | 0 |
| B. stabilis | 16 | 0 | 56.3 | 0 |
| B. vietnamiensis | 16 | 0 | 43.8 | 0 |
| Total | 267 | 5.6 | 34.8 | 0.4 |

Footnotes:
[a]Genetically unique strains from each B. cepacia complex species or novel group were selected using MLST (1).
[b]Test strains examined for susceptibility were B. multivorans ATCC 17616, S. aureus NCTC 12981 (antimicrobial testing reference strain) and P. aeruginosa PAO1.
[c]Both novel BCC and Group K categories constitute isolates which are known to belong to the B. cepacia complex but do not fall within any of the formally named species. Molecular genetic tests such as recA gene sequence analysis and MLST (reviewed and described in references 1 and 2) can be used to identify which B. cepacia complex isolates fall within the novel BCC or Group K designations.

Three findings stood out from the overall screen (Table 3):
(i) B. ambifaria (24% of strains tested) and B. cenocepacia IIIB (13% of strains) produced antimicrobials that were capable of inhibiting the growth of B. multivorans;
(ii) Only one strain of B. ambifaria (BCC0203; LMG-P24640; Table 2) produced an antimicrobial capable of a small amount of growth inhibition of P. aeruginosa; and
(iii) Over one third of Bcc complex bacteria produced anti-staphylococcal inhibition with only B. dolosa and B. multivorans strains lacking this ability.

These data show for the first time that the production of antibacterial compounds by members of the B. cepacia complex is more much widespread than previously thought (Table 3).

To follow up this observation a series of experiments were established focussing specifically on the anti-B. multivorans antimicrobial produced by B. ambifaria strain AMMD; this novel antimicrobial has been designated Ambifarin A.

Example 3

The spectrum of inhibition produced by B. ambifaria strain AMMD was subsequently found to be as follows:
(i) Inhibition of B. cepacia complex species. Ambifarin A inhibited all B. multivorans (24 strains), B. dolosa (8 strains), B. anthina (14 strains) and B. pyrrocinia (16 strains) tested (strains were drawn from those screened in Table 1).
(ii) Inhibition of gram negative pathogens. The antimicrobial inhibited: Pseudomonas species (P. putida, P. fluorescens and P. stutzeri; only B. ambifaria strain BCC0203 (LMG-P24640; Table 2) produced some inhibition of P. aeruginosa); Ralstonia species (R. mannitolytica and R. pickettii), multiresistant strains of Acinetobacter baumannii (FIG. 2, panel B) and several isolates of Stenotrophomonas maltophilia.

Ambifarin's broad spectrum and activity on multidrug resistant gram negative pathogens (Stenotrophomonas and Acinetobacter species) is very promising and of global importance in terms of combating infection with resistant pathogens.

In addition, the ability of Ambifarin A to inhibit 4 of the 10 formally named Bcc species that are inherently resistant to antibiotics is highly significant in terms of CF infection. Among the susceptible strains were pan-resistant isolates of B. dolosa which have caused highly problematic outbreaks in the US (10) as well as the Glasgow outbreak strain (16) and other major outbreak strains (2). Also treating B. multivorans infection is highly relevant to CF, since this species is now the dominant Bcc CF pathogen in the UK (5) and also rising in prevalence in the US (13).

Figure 4:
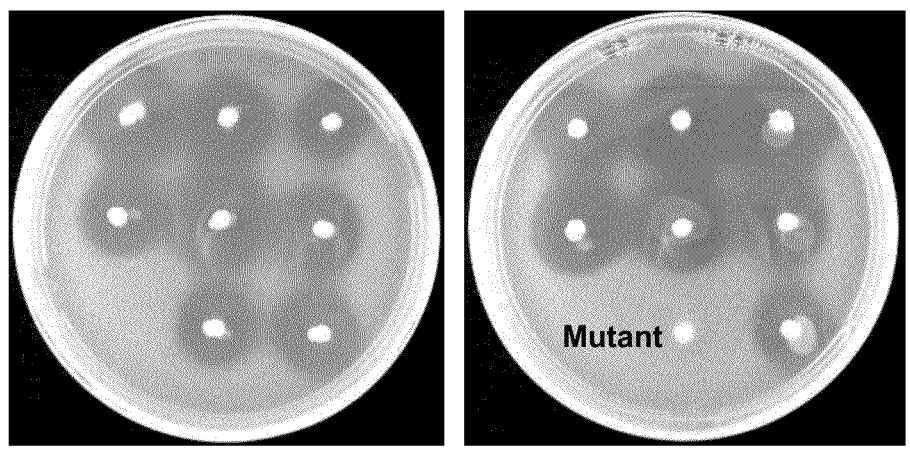
Figure 5:
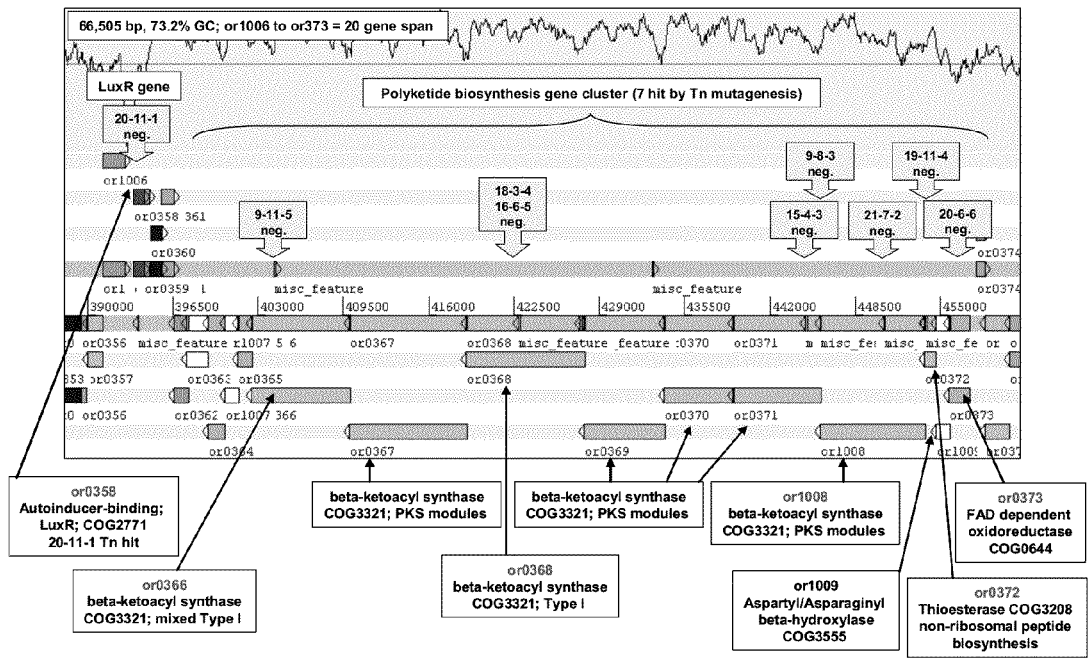

Further studies into the characteristics of Ambifarin revealed the following:
(i) Ambifarin production occurred during the stationary growth phase. The Ambifarin A antibiotic was optimally produced at 30° C. or lower, and occurs once the bacteria have reached stationary phase after about 18 hours of incubation;
(ii) Growth inhibition was stable. The Ambifarin inhibition of susceptible bacteria was very stable, with no growth or spontaneous resistance seen in the zone of clearing even if plates were left for several weeks. The lack of spontaneous Ambifarin resistance suggests that either the compound is very active or that more than one inhibitory factor is being produced, hence mutation to resistance is unlikely to occur;
(iii) Production of Ambifarin was carbon-source and media dependent. Production of the antimicrobial was highly dependent on the carbon source. The best production occurred when glycerol at 4 g/L was used as the sole carbon source; in minimal media containing arabinose, fructose, lactose, maltose or starch as the sole carbon source, Ambifarin production did not occur. Ambifarin production also appeared dependent on the formulation of the growth medium. A Basal Salts Medium (BSM; 7) produced the greatest amount of antimicrobial. Growth on other minimal media such as Bushnell-Haas Medium (8) or rich media such as Tryptic Soya Agar did not lead to active production of the antimicrobial. Addition of yeast extract (at 0.05%) to BSM-glycerol media enhanced production, however, production was independent of the presence of casamino acids in BSM;
(iv) Extraction of Ambifarin. The antimicrobial was isolated from the agar surrounding the growth of B. ambifaria AMMD. After growth, removal of bacterial cells and drying of the agar, Ambifarin was extracted efficiently with 100% methanol, producing an extract which showed considerable activity towards B. multivorans (FIG. 3).
(v) Stability and activity. The extracted Ambifarin A antimicrobial was highly stable from 4° C. to 60° C. (but inactivated by autoclaving), it was stable in mild acid and alkali (0.1 M HCl and 0.1 M NaOH) and preliminary viability assays have demonstrated it to be bactericidal in activity.
(vi) Genetics of Ambifarin A biosynthesis. B. ambifaria AMMD, the Ambifarin A producer (FIG. 1), had an available genome sequence at the Joint Genome Institute, and the strain was amenable to mutagenesis with mini-Tn5-Km (12). A small bank of 2000 random transposon mutants of AMMD was created and screened (8 mutants per plate) using random transposon mutagenesis (12) to isolate mutants incapable of inhibiting the growth of an overlay of B. multivorans (FIG. 4). Sixteen mutants that were stably negative for Ambifarin activity were isolated. By sequencing the DNA flanking the transposon insertions (11), the mutation sites were mapped to the AMMD genome as follows: 7 mutants mapped to a large (66 Kb) novel cluster of polyketide biosynthesis synthase (PKS) genes (FIG. 5); 4 mutants mapped to a hypothetical gene on; 2 mutants mapped to a Type II general secretion protein gene cluster; 1 mutant mapped to a glycosyl transferase encoding gene; and 1 mutant mapped to a LuxR-type quorum sensing regulator encoded at one end of the PKS gene cluster (FIG. 5).

Figure 6:
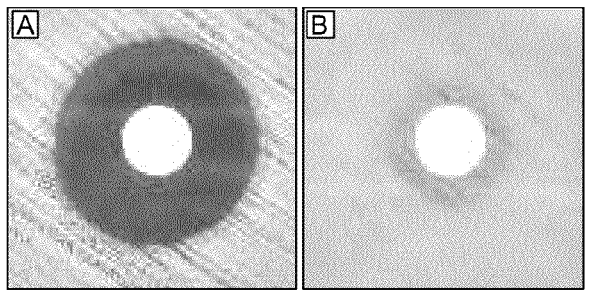

(vii) Binding to Amberlite XAD-16 resin. Extraction of Ambifarin could also be performed using an Amberlite XAD-16 anionic resin in a similar fashion to that described for other polyketide antibiotics such as erythromycin (14). Purification of Ambifarin A using the Amberlite XAD-16 resin also resulted in a much purer antibiotic preparation in comparison to methanol extraction of products secreted into agar (FIG. 3). The XAD-16 purified Ambifarin A retained excellent activity on gram negative bacteria, but had less activity on gram positive bacteria and had lost activity on fungi such as the yeast *Candida albicans* (see FIG. 6).

Figure 7:
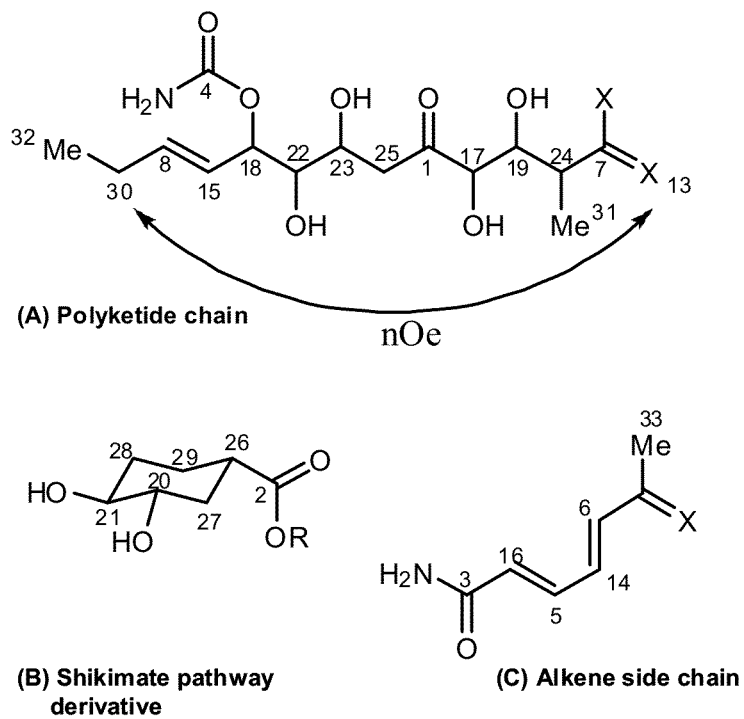
Figure 8:
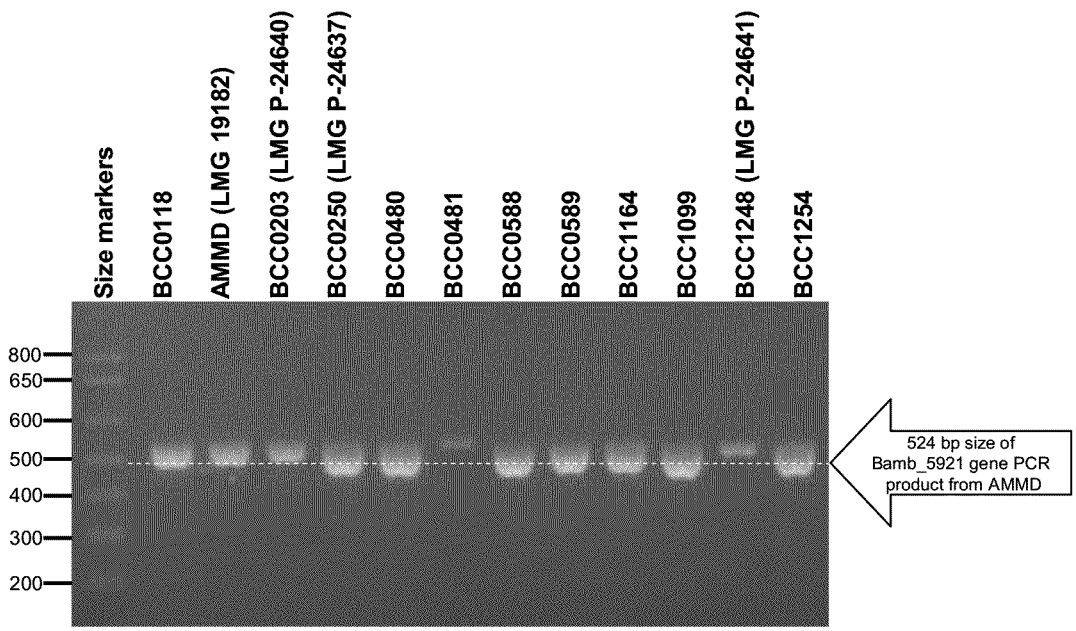
Figure 9:
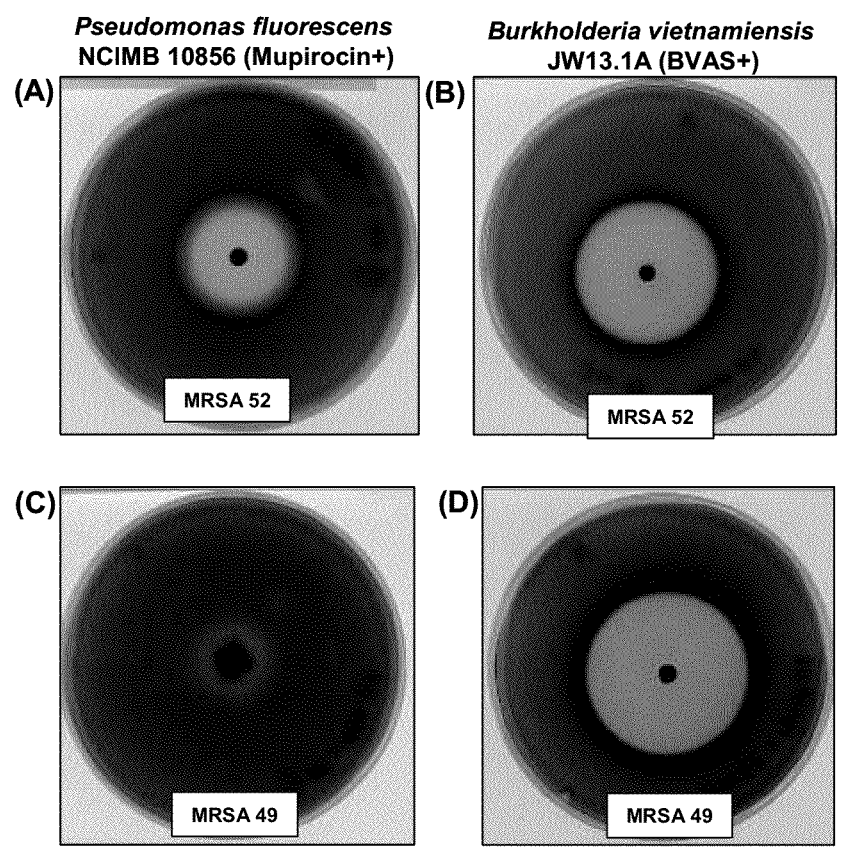

(viii) A chemical structure with components characteristic of a novel polyketide. Three components of the structure of Ambifarin A have been determined (FIG. 7): a polyketide chain, a shikimate pathway derivative and an alkene side chain. The presence of a polyketide chain defines Ambifarin A as a member of the polyketide antibiotic family.

(ix) Polyketide synthase genes are present in several antibiotic producing *B. ambifaria* strains. Using the genome sequence of strain AMMD, PCR tests were designed to detect PKS genes that were similar to those in Ambifarin A biosynthesis gene cluster (FIG. 5). The PCR screen demonstrated that several *B. ambifaria* strains known producing an antimicrobial after growth on BSM agar contained genes and possible PKS pathway that was identical to or very closely related to the AMMD gene cluster that makes Ambifarin A (Table 4). All *B. ambifaria* strains with an anti-gram negative antibiotic inhibition on *B. multivorans* (BCC0118 [LMG P-24636]; BCC0203 [LMG P-24640]; BCC0250 [LMG P-24637]; BCC0480; BCC0588; BCC0589; BCC1164; BCC1099; BCC1248 [LMG P-24641] and BCC1254) produced an amplification product with all three PKS genes indicating that they possess at least three of the PKS genes in the biosynthesis pathway and are producing a type of Ambifarin polyketide (Table 4). Minor variations in PCR product size compared to the expected size of the *B. ambifaria* AMMD positive control for each gene were observed for certain strains (Table 4) suggesting that while a similar PKS gene is present in these strains, it may vary slightly in sequence, and hence result in a PKS enzyme that will make a slightly different polyketide antibiotic. These PCR tests provide the ability to identify a *B. ambifaria* strain that is producing a polyketide of the Ambifarin family. However, it must also be noted that 4 *B. ambifaria* strains with excellent antimicrobial activity (BCC1100, BCC1107, BCC1241 [LMG P-24639] and BCC1065) did not produce any amplification with the AMMD PKS PCR primers (Table 4). This data indicates that certain *B. ambifaria* strains either possess completely unique PKS genes or are not secreting a polyketide antibiotic related to Ambifarin, and are producing novel antibiotics under the conditions of the invention.

Overall, these data show that the Ambifarins are a unique family of polyketide antibiotics (15).

Polyketide antibiotics form one of the largest classes of clinically successful therapeutics encompassing the macrolides (erythromycin, clarithromycin, and azithromycin) as well as the tetracycline family of antibiotics (15). In addition, they represent a group of secondary metabolites synthesized from modular gene clusters that can be genetically tailored to produce novel antibiotics that may overcome the current burden of resistance (15). Based on its spectrum of activity and unique genetics, it is clear that Ambifarin A constitutes a novel polyketide.

Example 4

In addition to the Ambifarin antimicrobial produced by *B. ambifaria*, several strains of *B. vietnamiensis* were found to produce an antibiotic that only inhibits gram positive bacteria such as *S. aureus*. One strain *B. vietnamiensis* strain JW13.1A (LMG-P24624; Table 2) was a highly potent inhibitor of MRSA (FIG. 2, panel A). This strain was isolated from a sample of contaminated diesel fuel. This antimicrobial has been designated Vietnamycin. Several further Bcc strains that produced potent anti-staphylococcal antibiotics were also present in the strain collection (Tables 1, 2, and 3).

TABLE 4

Detection of polyketide synthase (PKS) genes in *B. ambifaria* antibiotic producing strains

| | Antibiotic active on (mean zone of inhibition in mm) | | | Size of amplification product (bp) produced by amplification with primers for: | | |
|---|---|---|---|---|---|---|
| Isolate name | *B. multivorans* (Gram negative) | *S. aureus* (Gram postive) | *C. albicans* (yeast) | Bamb_5925 | Bamb_5921 | Bamb_5919 |
| Strains with positive PCR amplification: | | | | | | |
| AMMD (LMG 19182; positive control for PCR) | 25 | 15 | 17 | 415 | 524 | 555 |
| BCC0118 (LMG P-24636) | 24 | 12 | 22 | 400 | 524 | 555 |
| BCC0203 (LMG P-24640) | 33 | 33 | 40 | 415 | 524 | 555 (weak) |
| BCC0250 (LMG P-24637) | 18 | 10 | 17 | 400 | 524 | 555 |

TABLE 4-continued

Detection of polyketide synthase (PKS) genes in *B. ambifaria* antibiotic producing strains

| Isolate name | Antibiotic active on (mean zone of inhibition in mm) | | | Size of amplification product (bp) produced by amplification with primers for: | | |
|---|---|---|---|---|---|---|
| | *B. multivorans* (Gram negative) | *S. aureus* (Gram postive) | *C. albicans* (yeast) | Bamb_5925 | Bamb_5921 | Bamb_5919 |
| BCC0480 | 18 | 11 | 21 | 415 | 524 | 555 |
| BCC0588 | 25 | 14 | 22 | 415 | 524 | 555 |
| BCC0589 | 25 | 14 | 20 | 415 | 524 | 555 |
| BCC1164 | 12 | 11 | 13 | 415 | 524 | 555 |
| BCC1099 | 15 | 0 | 11 | 415 | 524 | 555 |
| BCC1248 (LMG P-24641) | 18 | 0 | 14 | 415 | 560 (weak) | 555 |
| BCC1254 | 17 | 0 | 13 | 415 | 524 | 555 |
| BCC0481 | 0 | 0 | 10 | 430 | 560 (weak) | 555 |
| BCC0477 | 0 | 0 | 9 | 792 | 0 | 0 |
| Strains with no PCR amplification: | | | | | | |
| BCC1100 | 38 | 36 | 11 | 0 | 0 | 0 |
| BCC1107 | 36 | 37 | 7 | 0 | 0 | 0 |
| BCC1241 (LMG P-24639) | 45 | 38 | 9 | 0 | 0 | 0 |
| BCC1065 | 35 | 32 | 10 | 0 | 0 | 0 |

SUMMARY

The broad spectrum of growth inhibition produced by antimicrobials produced by Bcc bacteria (Tables 1, 2 and 3) has not been previously observed or published. The screen demonstrated that 40% of strains examined produced inhibitory activity under the growth conditions used (Table 3). This was very surprising and was completely unexpected.

The antibiotics are produced from taxonomically well defined *B. cepacia* complex strains which can be systematically identified using MLST and those strains with potent antibiotic activity have been deposited in a recognised IDA;

The Bcc antibiotics have potent activity on multidrug resistant human pathogenic bacteria such as MRSA, VRE, other *Burkholderia* species, *Stenotrophomonas* species and *Acinetobacter* species which sets them apart from other known *Burkholderia* antibiotics;

While polyketide antibiotics have been described in other *Burkholderia* species they have not been described for a *B. cepacia* complex species and the *B. ambifaria* Ambifarin antibiotics are highly novel polyketides in terms of their activity and structure.

Many genetic pathways for the biosynthesis of antibiotics have been identified in the ever increasing pool of bacterial genome sequences, however, a major obstacle to the discovery of new antibiotics is understanding how to activate expression of these genes and prime production of the encoded antibiotic (13). The screening method described herein has primed antibiotic production in bacterial isolates that were not previously known to produce such compounds (Table 1). The method can be used to: (i) screen bacteria isolated from soils or other environments that are rich in antibiotic-producing microorganisms, or (ii) existing collections of *Burkholderia* or closely related bacteria for the production of novel antibiotics.

The potent activity of the Ambifarin A antibiotic was also very surprising. In particular, the fact that it was active on multiresistant gram negative bacteria such as *B. cepacia* complex bacteria themselves and other problematic resistant pathogens such as *Stenotrophomonas* and *Acinetobacter*. No antibiotic secreted by a *Burkholderia* bacterium has been found to be active on these bacteria or other *Burkholderia* species. Such multiresistant pathogens are the targets for major drug discovery programs. *B. ambifaria* strain AMMD is the Type strain for this Bcc species (2). It has been made available to many researchers through culture collections (3). The genome sequence of *B. ambifaria* AMMD is also publicly available and the inventors have identified the PKS genes involved in Ambifarin production. The inventors have specifically shown that these genes are actually responsible for production of Ambifarin in *B. ambifaria* by the use of transposon mutagenesis. They have also shown that several other *B. ambifaria* strains in their collection (Table 4) and deposited in an IDA (Table 1 and 2) also possess PKS genes which are related to those in strain AMMD and hence are capable of producing novel polyketides within the Ambifarin family. The inventors have also determined a partial structure for Ambifarin A produced by *B. ambifaria* strain AMMD which shows it is a unique *Burkholderia* antibiotic.

The Vietnamycin antibiotic is also very promising since it has excellent activity against problematic pathogens such as MRSA. An additional feature of the Vietnamycin antimicrobial is that it is still capable of inhibiting the growth of MRSA strains that are resistant to mupirocin (FIG. 6), the antibiotic that is the currently the mainstay of MRSA and anti-gram positive topical therapy. The Vietnamycin antibiotic is also capable of inhibiting the growth of fungal pathogens such as the infective yeast *Candida albicans*. It has also been shown that the Vietnamycin antibiotic is capable of inhibiting the growth of cord forming wood-decaying *Basidiomycete* fungi which are not human pathogens. This indicates that it has a broad spectrum of activity.

The content of all references identified herein are incorporated herein by reference in their entirety.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

TABLE 5

Figure 11A:
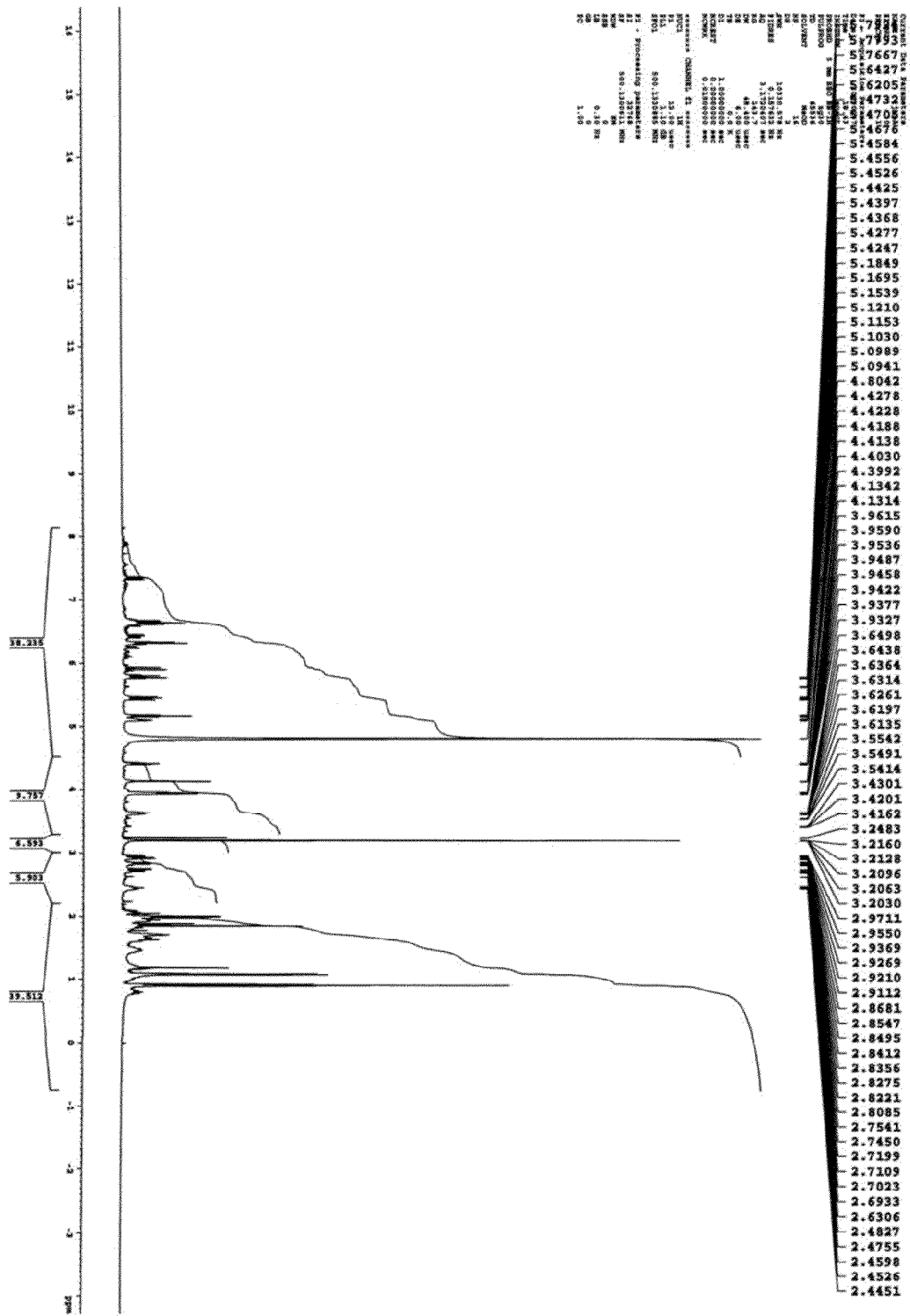
Figure 11B:
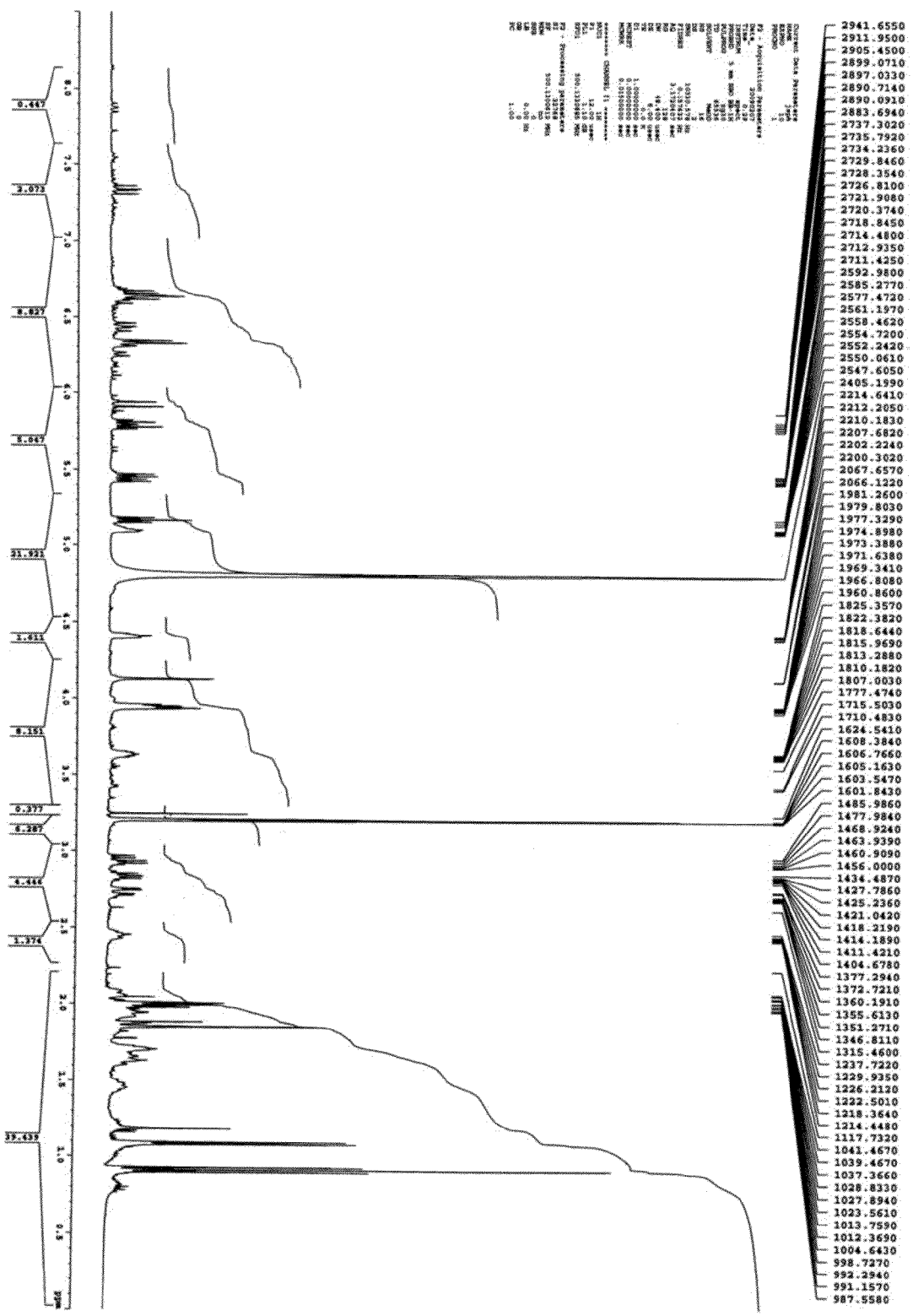

$^{13}$C (100 MHz) and $^{1}$H (500 MHz) NMR spectral data for Ambifarin A in MeOD-d$_4$ as obtained from FIGS. 11A and 11B.

| No. | δC | δH | int. | mult. | J= | COSY | HMBC |
|---|---|---|---|---|---|---|---|
| 1 | 210.1 | | | | | | 17, 25 |
| 2 | 177.6 | | | | | | 26 |
| 3 | 167.1 | | | | | | 5, 16 |
| 4 | 157.3 | | | | | | 18 |
| 5 | 145.4 | 7.33 | 1 | dd | 15.1, 11.1 | 14, 16 | 6 |
| 6 | 145.2 | 6.66 | | d | 15.5 | 14 | 5, 33 |
| 7 | 139.3 | | | | | | 13, 19, 31 |
| 8 | 137.8 | 5.80 | 1 | dt | 15.3, 6.3 | 15, 18, 30 | |
| 9 | 136.1 | | | | | | |
| 10 | 135.6 | 6.36-6.30 | 2 | m | | | |
| 11 | 130.2 | 6.67-6.60 | 2 | m | | | |
| 12 | 130.2 | 6.67-6.60 | 2 | m | | | |
| 13 | 127.0 | 6.36-6.30 | 2 | m | | | 24 |
| 14 | 125.9 | 6.44 | 1 | dd | 15.1, 11.2 | 5, 6 | 16 |
| 15 | 124.8 | 5.45 | 1 | ddt | 15.3, 7.4, 1.5 | 8, 18, 30 | |
| 16 | 120.0 | 5.93 | 1 | d | 15.1 | | 5 |
| 17 | 77.6 | 4.13 | 1 | d | 1.5 | | 19 |
| 18 | 74.1 | 5.17 | 1 | t | 7.4 | | 8, 15, 22, 30 |
| 19 | 72.7 | 3.96 | 1 | dd | 9.5, 1.4 | | 17, 24 |
| 20 | 71.7 | 5.14-5.08 | 1 | m | | | 21, 27 |
| 21 | 69.1 | 3.66-3.60 | 1 | m | | | 20, 28 |
| 22 | 66.6 | 3.94 | 1 | dd | 8.0, 2.5 | 23, 18 | 15 |
| 23 | 65.5 | 4.41 | 1 | ddd | 7.2, 4.5, 2.5 | 22, 25 | |
| 24 | 46.2 | 2.84 | 1 | qd | 9.5, 6.7 | | 19, 31 |
| 25 | 43.2 | 2.95 | 1 | dd | 17.1, 8.0 | | 23 |
| | | 2.74 | 1 | dd | 17.1, 4.6 | | " |
| 26 | 37.2 | 2.45 | 1 | tt | 11.2, 3.3 | | 27, 29 |
| 27 | 30.9 | 2.07 | 1 | br · d | ~14 | | 26 |
| | | 1.68-1.60 | 1 | m | | | " |
| 28 | 28.1 | 1.75-1.68 | 2 | m | | | 29, 21 |
| 29 | 26.1 | 2.00-1.90 | 1 | m | | | 28 |
| | | 1.52-1.40 | 1 | m | | | " |
| 30 | 25.0 | 2.03-1.96 | 2 | m | | | 8, 15, 18, 32 |
| 31 | 14.9 | 1.09 | 3 | d | 6.7 | | 24 |
| 32 | 12.2 | 0.92 | 3 | t | 7.4 | | 30 |
| 33 | 11.3 | 1.86 | 3 | s | | | |

Data for each of the 33 Carbon atoms detected by NMR were used to determine the structural components of the Ambifarin polyketide.

REFERENCES

1. Baldwin, A., E. Mahenthiralingam, K. M. Thickett, D. Honeybourne, M. C. Maiden, J. R. Govan, D. P. Speert, J. J. Lipuma, P. Vandamme, and C. G. Dowson. 2005. Multilocus sequence typing scheme that provides both species and strain differentiation for the Burkholderia cepacia complex. J Clin Microbiol 43:4665-73.
2. Baldwin, A., E. Mahenthiralingam, P. Drevinek, C. Pope, D. J. Waine, D. A. Henry, D. P. Speert, P. Carter, P. Vandamme, J. J. Lipuma, and C. G. Dowson. 2008. Elucidating Global Epidemiology of Burkholderia multivorans in Cases of Cystic Fibrosis by Multilocus Sequence Typing. J Clin Microbiol 46:290-5.
3. Coenye, T., E. Mahenthiralingam, D. Henry, J. J. LiPuma, S. Laevens, M. Gillis, D. P. Speert, and P. Vandamme. 2001. Burkholderia ambifaria sp. nov., a novel member of the Burkholderia cepacia complex including biocontrol and cystic fibrosis-related isolates. Int J Syst Evol Microbiol 51:1481-90.
4. Coenye, T., P. Vandamme, J. J. LiPuma, J. R. Govan, and E. Mahenthiralingam. 2003. Updated version of the Burkholderia cepacia complex experimental strain panel. J Clin Microbiol 41:2797-8.
5. Govan, J. R., A. R. Brown, and A. M. Jones. 2007. Evolving epidemiology of Pseudomonas aeruginosa and the Burkholderia cepacia complex in cystic fibrosis lung infection. Future Microbiol 2:153-64.
6. Govan, J. R. W. 2000. Infection control in cystic fibrosis: methicillin-resistant Staphylococcus aureus, Pseudomonas aeruginosa and the Burkholderia cepacia complex. Journal of the Royal Society of Medicine 93:40-45.
7. Hareland, W. A., R. L. Crawford, P. J. Chapman, and S. Dagley. 1975. Metabolic function and properties of 4-hydroxyphenylacetic acid 1-hydroxylase from Pseudomonas acidovorans. J Bacteriol 121:272-85.
8. Hilyard, E. J., J. M. Jones-Meehan, B. J. Spargo, and R. T. Hill. 2008. Enrichment, Isolation, and Phylogenetic Identification of Polycyclic Aromatic Hydrocarbon-Degrading Bacteria from Elizabeth River Sediments. Appl. Environ. Microbiol. 74:1176-1182.
9. Jones, B. V., R. Young, E. Mahenthiralingam, and D. J. Stickler. 2004. Ultrastructure of Proteus mirabilis swarmer cell rafts and role of swarming in catheter-associated urinary tract infection. Infect Immun 72:3941-50.
10. Kalish, L. A., D. A. Waltz, M. Dovey, G. Potter-Bynoe, A. J. McAdam, J. J. Lipuma, C. Gerard, and D. Goldmann. 2006. Impact of Burkholderia dolosa on Lung Function and Survival in Cystic Fibrosis. Am J Respir Crit. Care Med 173:421-5.
11. Mahenthiralingam, E., T. A. Urban, and J. B. Goldberg. 2005. The multifarious, multireplicon Burkholderia cepacia complex. Nat Rev Microbiol 3:144-56.
12. O'Sullivan L, A., A. J. Weightman, T. H. Jones, A. M. Marchbank, J. M. Tiedje, and E. Mahenthiralingam. 2007. Identifying the genetic basis of ecologically and biotechnologically useful functions of the bacterium Burkholderia vietnamiensis. Environ Microbiol 9:1017-34.
13. Reik, R., T. Spilker, and J. J. Lipuma. 2005. Distribution of Burkholderia cepacia complex species among isolates recovered from persons with or without cystic fibrosis. J Clin Microbiol 43:2926-8.
14. Ribeiro, M. H., and I. A. Ribeiro. 2003. Modelling the adsorption kinetics of erythromycin onto neutral and anionic resins. Bioprocess Biosyst Eng 26:49-55.
15. Walsh, C. T. 2004. Polyketide and nonribosomal peptide antibiotics: modularity and versatility. Science 303:1805-10.
16. Whiteford, M. L., J. D. Wilkinson, J. H. McColl, F. M. Conlon, J. R. Michie, T. J. Evans, and J. Y. Paton. 1995. Outcome of Burkholderia (Pseudomonas) cepacia colonisation in children with cystic fibrosis following a hospital outbreak. Thorax 50:1194-8.

The invention claimed is:

1. A method for producing an antimicrobial agent, the method comprising:
   (i) culturing a *Burholderia cepaca* complex (Bcc) bacterium, on minimal media comprising glycerol as the sole carbon source;
   (ii) allowing an antimicrobial agent to accrue; and
   (iii) isolating the antimicrobial agent.

2. A method according to claim 1, wherein the bacterium comprises one or more genes selected from *B. ambifaria* (Bamb) 5919 (SEQ ID NO:1), *B. ambifaria* (Bamb) 5920 (SEQ ID NO:2), *B. ambifaria* (Bamb) 5921 (SEQ ID NO:3), *B. ambifaria* (Bamb) 5922 (SEQ ID NO:4), *B. ambifaria* (Bamb) 5923 (SEQ ID NO:5), *B. ambifaria* (Bamb) 5924 (SEQ ID NO:6) and *B. ambifaria* (Bamb) 5925 (SEQ ID NO:7) or a fragment or variant thereof.

3. A method according to claim 2, wherein the bacterium comprises Bamb 5919 (SEQ ID NO:1), Bamb 5920 (SEQ ID NO:2), Bamb 5921 (SEQ ID NO:3), Bamb 5922 (SEQ ID NO:4), Bamb 5923 (SEQ ID NO:5), Bamb 5924 (SEQ ID NO:6) and Bamb 5925 (SEQ ID NO:7) or a fragment or nucleic acid variant thereof.

4. A method according to claim 1, wherein the method comprises incubating the bacterium on minimal media until the stationary phase.

5. A method according to claim 1, wherein the method comprises incubating the bacterium on minimal media for at least 16 hours, optionally about 48 hours.

6. A method according to claim 5, wherein the method comprises incubating the bacterium on minimal media for between about 48 and about 120 hours.

7. A method according to claim 1, wherein the minimal media is a basal salts medium.

8. A method according to claim 1, wherein step (iii) comprises extraction of the antimicrobial from the minimal media with an alcohol, optionally, wherein the alcohol is methanol.

9. A method according to claim 1, wherein glycerol is present in an amount of between about 2 g/L and about 12 g/L.

10. A method according to claim 1, wherein the bacterium is incubated at a temperature of between about 25° C. and about 35° C.

11. A method according to claim 1, wherein the bacterium is incubated at a temperature of less than about 30° C.

12. A method according to claim 8, wherein an anionic resin is used to isolate the antimicrobial agent, optionally, wherein the anionic resin is Amberlite XAD-16.

13. A method according to claim 8, wherein the alcohol comprises between about 70% and about 90% methanol vol/vol.

14. A method according to claim 13, wherein the alcohol comprises about 80% methanol vol/vol.

15. A method according to claim 8, wherein step (iii) comprises extracting and drying the minimal media.

16. A method according to claim 15, wherein step (iii) comprises breaking up the minimal media.

17. A method according to claim 15, wherein drying comprises freeze drying the minimal media.

18. A method according to claim 16, wherein drying comprises freeze drying the minimal media.

19. A method according to claim 16, wherein step (iii) comprises breaking up the minimal media.

* * * * *

SEQUENCE LISTING

```
<160> NUMBER OF SEQ ID NOS: 13

<210> SEQ ID NO 1
<211> LENGTH: 7392
<212> TYPE: DNA
<213> ORGANISM: Burkholderia ambifaria
```

<400> SEQUENCE: 1

```
atgcaagaca ttcagcagct cctcgcgaag agcctgaccg aaatcaagcg cctgaaggcg    60
gccaaccagg cgctcgagca ggcccgccgc gagccgatcg cgattgtcgg cgcggcctgc   120
cgctaccegg gcgggatcgg ctcgctcgac cagctctgga ccgcgctcga ggcgggccgc   180
gacggcatcc gcacgatggt cggcgagcgc tggccgatgc agcgcttcct caccgacgat   240
ccccaccggc ccgcggcat ctacagcgat gcgatgggcc tgctcgaggc gatcgacggt   300
ttcgatgccg cgcatttcgg cctgcgccac gacgaggcga tccacatcga cccgcagcat   360
cggctgctga tggaagtggc ctgggaggcc ttcgaggatg ccggctacgc ggtggacgcg   420
ttctcgggca gccgcaccgg cgtctacgtc gggatcatga cgacgacta cggccagctg   480
caggggccgc tggaggcggc cagcctctac atcggctcgg gcatcgccaa gagctgcgcg   540
gcggggcggc tggcctacac cttcgggctg gaggggccga cgctggcgct cgacaccgcc   600
tgctcctcgt cgctggtggg cgtgcacctg gccgtgcagg cgctgcggcg cggcgaatgc   660
gacgcggcgc tggccggtgg cgtgaacctg atcctttcgc cgcagggcac ggtggtggcc   720
tgccgctcgc agatgctctc gccgagcggg cgctgccgca ccttcgacgc cagcgcagac   780
ggctacgtgc gcgccgaggg ctgcgggctg gtgctgctca agcgcttgtc cgatgccgaa   840
cgcgacggcg accggatcct cgcgctggtc gcgggctcgg ccgtcaacca cgacggccgc   900
acgcagggcc tgaccgcgcc gagcggccag gcgcagcggc gcgtgatcgc ggcggcgctg   960
gccgacgcgg cgtggcggc cgccgaggtc ggcttcgtcg aatgccacgg caccggcacc   1020
gcgctgggcg atccgatcga gctgcgcgcg ctggaggcca gctacgtgct cgaagcgggc   1080
gagcgcgcgc cgctggtggt cggcgcgctg aagtccaatc tcggccacat ggaatcggcg   1140
gccggtatcg gtggcctgca caaggccatc caggtggtgc cgcatcgcag ggtgccgagg   1200
aacctgcatt tcgagaccct caatccgcag attcgcgtcg acctcgagcg gctgcgcatc   1260
gccgccgagg cggtggcgat gccggaacgg gaacgcgcgc tggcgggcgt cagctcgttc   1320
ggcttcagcg gcaccaatgc gcacgtgatc gtcgaggcct atgcgccgcg ggacgatcga   1380
gtgggcgtgg acgctcggc acatgaagac gccgccaacg cggaggctgc accgctgcag   1440
ctattccggc ttgccgcgca ttcgggcgcc gcgctggccg actacgcgcg ccgctacctc   1500
gactggctcg acgacgcgca cgcgcggcaa gcccggctcg atccggccgc gctctgctac   1560
acggccgcgg tgggccgcgg cgaggccggc tgccggatcg cgctgagctt cgagacgctc   1620
gatgacctgc gcgcctgcct gcgcgaatac ctcgacgtgg ccggcggcga cccgagcgag   1680
ccggtgccga atcctgcgc ggccgagtgg gtgatcggcg gcgcggccga tgtcgactgg   1740
cgcgtggccg gggcgctgca tgcgcagccc ggcttctatc gcgagcgggt ccagcaggcc   1800
tgggcgcgcc tcgcgtcgcg cgtgccggat ggcgccgccg cgttcgcgcg gctctgcgcg   1860
ggcggcgatg ccggcttgcc ggccgacgcg acgctaccgc acacggtgca ccgctgggcg   1920
ctcgcgcagc tgctagtcca cctcggcctg cagccggccc gcgtgagcgg ccatggcgcc   1980
ggcgagtatg tggcggcggc cgtcgcgggc ctggtcgact gggacacggc gctcggcctc   2040
gcggccggcg aggcactgcc ggccggcttc aaggcgggcc gcgcgcgctg cgaattcacc   2100
agccgcttcg cgacgggcga gctgcccgag tcgtggcagc gcgacggcgg cccggcggcg   2160
gccgacgcgg ctccgctcgg cgacgaggct tggcccgagc acgcgcaggg catcgtggtc   2220
gagctgggcg cgggcctcgc gctgcggctc ggcgatgcgg ccgacgagcg cctgttccgc   2280
```

```
tggacccacg gccgcaccaa tcgcgacccg gcccggccgc tcgaggcctt cctcgcgcag    2340
gcctacatgg cgggcctgcc ggtgcgctgg gcgccgctgt cgaggcgcag gcgccgcgc     2400 cgccagagcc agcccggtta ccgttccag cgcgagcgcg tgtggaccga ctggggtat      2460 tcgttcgacg cgacgctgcc gtccaccgtc ggccgcgccg gcggcggcgt ggcgccgcgc    2520
ctgccggcgc tcgccaccgg gctggccgcg gagccgctcg atcacccggt gctgcgcagc    2580
ctgttcgcgt gcccgtcggg cgcacgcaat ttctcgggcg agctttcgct cacgcgctg    2640 ccctacctgg ccgcgcaccg catcctcggc gagatcgtac tgccggccag cgcgcagttc    2700
gacctgatcg ccaccgcggg ccgcgcatgc tggccgggcc agccgctgct gatcgacgag    2760
ctgcagctgc cgaaccgctg cgtgctcggc gacgagccgc tcgaagtcta ctgccacctg    2820
cggcccgccg acgggcgcgt cgagctgcat gggcggccgc gcggcgcgcc gggctggacg    2880
ctccacgcgc gggcgcgcat cgcgccggac gaggcccacg cggccaacgc gccggccacc    2940
gtcgatccgg ccgcctggcg cgccgcctgc ccgaaccggg tgccggtgcg ccgccactat    3000
cacgcgatcg cgcaggtcgg gctcgaatac gaggccgact tccagggcat cttcgaactg    3060
tcgcgcggca ccggctgcgc gctcgccaag atcgcgctgc cgcccggcgt cgaccagtcg    3120
ctggacggct acagcaccca cccgatcctg ctcgacgcct gcctgcaggc gatttccgca    3180
gcctcgccgc ccgatgccgg cggcgagctg ctgatcccgg ccgcgatgcg cggcatccac    3240
ctgttcaggc cgctgcccga actgatctgg tgccgcgtcg aggtcctcgc cgacgacggc    3300
gggcgcggca cccagcacgc caagctgacg atcgtcgaca tgcagggcga gccggtgatg    3360
cgcatcgacc gcttcgagac cacgcgttac acgggcgccg tcgcgcccgc tgccgagaac    3420
tggacccact ggctctacga ccggcactgg gtgccggccg cgccgtgcgc ggcttcgtcg    3480
tcgtcggcca gcgtgccgc gcgccactgg ctgctgctca gcgacggcgg cacggcctgc    3540
gcggcgctcg cgacggtgct ggccgcgcgc ggcgatcgcg tctcggtgct cggccgcgag    3600
gccgcgccgc ccgacgcgga cggcttcggc gcgttgatcg atggcgcggc ggccgatggc    3660
ggcctcgacg gcgtgatcca cggctggtcg ctcgacggct tcgatcccga ggcgcacggg    3720
ccggggcacg aggccgtgtc ggacgaggcg ctggcgcgct gcgcgcaggg gccgctgtgg    3780
ctatgccagg ccgcgctcgc gccgggccgg cgcgaactgg cgctgcattt cctcacgcgc    3840
ggcagccagc cggccggcgg ctcgcgcgtg cgggcgccgc tggccgcgct ggcctggggg    3900
ctggtgggca gcttcgtcaa cgaacagcgc cgcccggcgc gcctggtcga tctcgacccc    3960
gacagccgcg acgccgcgc ggatgccgcg ctgctggtgc aggcgcttca cgcggacggc    4020
gaggagacgc agtacgcggt gcgcggggcg cgcctgctgg tggcgcggct gcggcgcgcc    4080
gcgccgctcg cggcgccagc gccggtgatc gatcccgagg ccagctacct gatcaccggc    4140
ggttacggcc agctcggcat cgagacggcc accgcgctgg cgcggcaggg cgcgcgccac    4200
ctggtgctgg tgggccgcga tccgtcccgc gccgagggcg acccggcgct ggccggcctg    4260
cgcgagatgg gcgtgcgact gacgccgctg gcggccgacg tgggcgagcg cgccagcttc    4320
ctgccgcgcc tggccgaatg cctgcgcacg ctgccgccgc tcaagggcgt ggtccattcg    4380
gcgggcagcc tggacgacgg cgtgctcgac gaccaggact gggggcgcta cctcgcggtg    4440
ttcgccgcca aggtggccgg cacgctcaat ctccatcacg cgctgcgcaa gcatgcgctc    4500
gatttcttcg tgctctattc gtcggcggcc gcgctgctcg gcaacccggg gcagaccaac    4560
tacgcggccg ccaatgcctt cctcgacagc ttcgccgcct atcgccgcgg cctcgggctg    4620
gcagggctgg cgatcggctg ggccggctgg gcgggcgggg ggatggccgc cggccggggc    4680
```

```
gaggcgcgcg ccgaggccac gatcggcctg atcccgccgg agcagggtgc cgaggtaatc    4740
gcccgccagt tcgcgcatcg cgacggcgat ttcgccttga tcccgatgcg gctcgccgcg    4800
ctggccggcc aggaccgcat gccctggctg cgtgcgctgc tggccgagct ggtcgaggcc    4860
gaggcaggcg cgacgggcgc gagcggagca ccgcgcgtcg agcgccgcgc cggcggcacg    4920
gccggcgcgg cactgctggc gggcctcgcg agcctcgatg cggcggcgcg cgcggcgcgc    4980
ctgaagcgcc atctcgaggc cgcgatccgc aagctgctca accgcgccga tacgctcgac    5040
gatcgcgcca gcatgttcga tctcggtctc gattcgctgc tcagtatcga cctgcgcatg    5100
cagctcgaga aggacctggc ctgcagcctc tcgaccacgg tgctgcacga ccatccgacc    5160
atcgaggcgc tggcgggctt cctggccgaa cgcgtgggtg cgccgccggc ggggacggtt    5220
cgcgcagggg ccgcgggcgg tgccggtgca ggcaccggcg cgcctgccgg cgccactggg    5280
gccgcggctg cgcatgccgt atcgtcggcc tcgcccgtgc cggccggggc cgcgtcggcc    5340
gctgcatccg ctgcatccgc tgcagcggca gccggcgccc cgtcgcgcgc cacgttcgcg    5400
gccgagccgc gtcgtgccgg cggcgcggcg ctgccgcccg gcgccggccc cgacgacatc    5460
gccatcatcg gcgtatcggg ccgctacccc ggcgcggccg acctcggcgc gttctgggac    5520
aacctgcgcg acggccacga cgcgatcacc ccgatcccgc ccgagcgctg gaaccacgac    5580
gcctacttcg accggcagcg caacgtgccc ggcaagagct acagcgcctg gggcggcttc    5640
atcgaggacg tcgacgcctt cgacccggcc ttcttcagca tctcgccgcg gatgtcggcc    5700
tacctcgatc cgaaggagcg gctgttcctc gagacggtct ggaacctgct ggaggaggcg    5760
ggcgagacgc gcgagcgcat gcagcaggcc tatgcgcgcg aggtgggcgt gttcgtcggc    5820
gcgatgtacc agctctatgg cgcctgcgcg ccgacgagg cgagcgcgt ggccaccgcg    5880 ctgtcctcct acaacgcgat cgcgcatcgc acctcgtact tcttcaacct gcgcgggccg    5940
agcatcgcgc tcgacacaat gtgctcgtcg tcgctgacgg cggtccacta cgcctgccgc    6000
agcctgctcg acgcgactg cgcgctgccc atcgcgggcg gcgtgaacct gtcgctgcat    6060
ccgcgcaagt acgtcgggct gagccaggcg cagatcgtcg gcagccatgc cgacagccgc    6120
agcttcagcg acggcgacgg ctacctgccg gccgaggggc tgggcgccgt gctgctcaag    6180
ccgctggccc gcgcgctggc cgacgacgac cggatcctgg cggtgatcaa agcctcctcg    6240
gtcaaccacg gcgccgcgc gaccggctac tacgcgccga acgcgaacgc ccaggtcgac    6300
ctgatggagg ccagcttccg caaggccggc gtgtcgcccg agtcgatcga ctacatcgag    6360
gccgccgcca acgcaccag cctcggcgac gcggtcgagc tgcgcgcgct ggcgcgcgtg    6420
ttcgacggca ccgcgcgcga cggccggcgc gtgccgatcg gcactgtgaa gtcgaacatc    6480
ggccatcccg aggcggcctc gggcatcgcg caactgacca aggtgatcct gcagatgcag    6540
cacgagacgc tggtgccctc gatcaagacc gagcccgtca ccccaacct cgacctggcc    6600 cacacgccgt tccgcctgct ctcgcggcag gcggcctggc cgtccgatcc ggcgcggccg    6660
cggcgcgcca cggtcagctc gttcggcgcg agcggcgcga acgcgcacct gatcgtcgag    6720
gccttcgaga cggtcgaggc ggagcccgcg ccagccgtcg cgcaagcggc cgccggcc    6780 gagatcgtgg tgctgtcggc gcgcacgccg gctcagttgc gcgaggtggc gcggcgcctg    6840
ctggcctggc tcgccacgcg caggcggcg ggcagggcgg aatcggcggt gccgctggcc    6900
gagcgcggcc gcgcctgctc gctcgcgaat ctcgcgcaca cgctgcagat cgggcgcgag    6960
gcgatggact gccggctcgc gctgctggcc gacagcctcg acacgcttgg cgatggcctg    7020
```

```
cggcgtttcc tcggcgaatc ggccggcgcg gccgagcccg cgatctacca cggcaacgtg      7080
caggaccagc tcgagatgcg caacctgctg gcgggcgccg ccggcgacgc gatggcgcag      7140
accctggtgg ccgaacgcaa cctggagggg ctgatgctgc actgggtcca gggcggcaac      7200
gtgccctggg ccgccctgcg cgagggccgg ccggcgcgcc gctggtgct gccgacctat       7260 ccgttcgagc gcgagcgcta ctggctgtcc ggcgcgagcg acgccgcggg ccgcggcgcg      7320
ggcgagccgc aggtccctgc cgagccggcc gaggcggcca gcgaacccag tgtcgtcgat      7380
gggcgggcct ga                                                          7392

<210> SEQ ID NO 2
<211> LENGTH: 8928
<212> TYPE: DNA
<213> ORGANISM: Burkholderia ambifaria

<400> SEQUENCE: 2
ttgaacgact acaaggcatt gctcaagagc tcgatccgca agatccagga acaggatcgg        60
cgcatccgcg aactcgagtc cggcgtcgac gagccggtgg cgatcatcgg catgtcgtgc       120
cggtttcccg gcgcacccga cgccgaagcg ttctggcgcg cgatcgaggc cggcgccgac       180
acggtgacga ccatgaccgg ccagcgctgg gaaatggagg cctggcatac cgacgcggcc       240
tcggccgagg ccgccgaggc cggccgcatc tacacgcgcc gcttcggcct gctggaggac       300
atcgacggct tcgagccggg cgccttcggc atctccgagg aggaggcgcc ctacatcgat       360
ccgcagcacc ggctgctgct cgaacaggcc tggttctgcc tggagcacgc gggcctcgac       420
gcgaagacgg tgaagggcag cgacatcggc gtgttcgtcg ccagatgaa caacgactac        480 gcgcggctga tccgccgcgc cgaggacctc aatccctacg tgggcgccgg cagtgcgccg       540
agcgcggcgg ccggccgcct gtcctacgtg ttcggcctga aggggccgag catcacgatc       600
gacacggcct gctcgtcctc gctggtggcc gtgcacttgg ccagccagag cctgcgcctg       660
ggcgagtgcg ggatgcgct ggctggcggc gtgaacctgc tgctgagtcc cgagacggcg        720
gtgggcgcct cgtcgcgcg catgctgtcg gcgcgcgggc gctgcaatac cttcggcggc        780
gaggcggacg gctacgtgcg cgccgagggc tgcggcctgt tgctgctcaa gacgctgtcg       840
cgcgcgcgcg ccgacggcga caccgtgctg gccgtcatcc gcggctcggc ggtgaaccag       900
gacgccgcga ccacggcct gagcgccccg aacggcccgg cccaggtgca ggtgatgcgc        960
gatgcgctgg cgcgcgcgcg gctcgacccg gccgaggtcg gctacctgga gacgcacggc      1020
accggcaccc cgctcggcga tccggtcgag gtgcaggcga tcgacaccgt ctacggtcgc      1080
gccgagggac gccgctcgcc gctcgcgctg gcgccgtga aggccaacat gggccacggt       1140
gaatcggccg ccggcatcgc cgggctgatc aagctggtgc agctgctgcg cacgacagc       1200 ctgccgccgg tcgcgcatct cgatgcgctg aatccgcatt tcgacggtct cagcgaccag      1260
ctgctattcc cgaagggcgc cgccgccgcg tggccgcaag ggcgcccgtc ggtggccgcg      1320
ctaagctcgt tcggctatac cggcaccaat gcgcacctgc tgctctcgcc cggcgacgcg      1380
ctcgacgccg atgccgaagc ggcccgtccc gcgcatcgct tcgagcgccg ccgctactgg      1440
ctgcccgacc acatgacggc gcgcgcgggc gcgctgccgg cgctgttcga gccggtacgc      1500
catccgttct tcgcgaccag catgaacgag cccgacggcg gctccctgct ggccggcgaa      1560
ctgtcgctgg cgcgtcagcc cttcctgcgc gaccacgtgg tggccggcga ggtggtgctg      1620
ccggccagct gcttcgtcga tatggtggtg catgcctgcg cggccgcgct cggcgcgccc      1680
gcgcgcatcg aacagatgag cctcttgcag ccctgcgtgc tcggcgagac gccgctgggc      1740
```

```
ctctattgcc gcgtcggccc gcgcggcggc gacacgctgg ccgtcgacat cctgacgcgc    1800 ccgcgccggcc gcgaggactg gcagcaccat gtgcgcgcga gcgtgcgcgc ggtgccggcc    1860
gcggccgcgc ggcagcacga cctggctgcc gatcgcgccg cctgccccga gccggtttcg    1920
cccgaggcgc tgcggcgcga ggcgcgcgag gccggggtgg cctacgggcc ggcattccgc    1980
gcgatcgagg gcctgtggcg cgggcccggc gtcgcgctgg ccgcatcgt acggccggcc    2040 gcgctgggcg ccggctggaa cggcccggc ctgcacccgg tgatgctcga cgcctgcttc    2100
caggtgatcg gcgcggcggc ggccggcgag ggcggcgcgg acggcccgcg cggcctgttc    2160
gtgccggccg cgctgcacgg cgtgcgcgac ggcgtgcagg acggtggccc gcgcgcggcc    2220
acgctctggt gtgtcgcgcg catcgacggg cccggcgcgc cctgggccga cgatgcctcg    2280
ctgcacgact acctgcgcgg tcgcgacaac ttctcggtgc agctgcgcgt gtgcgacgag    2340
cagggccgcg aactgctgtc gatcgagcgc ttcgaggcgg cgcgctatcg cccgcgggca    2400
gccgccgagg catggcgcga ctggctgctg gagcggcact ggctgccggc cggcgcgccg    2460
cgcgcgacgg gcttcgcgct gacggcggcg gcgctggtcg ccgacctcgg cgccgatgcc    2520
aacgcggctt cctacgtggt gagcgacgcg ctgcgccgcg gcttcgacga gatcgccgcc    2580
ggctacgtcg cgcgcgcgct cgacgcgctc gagctgacgc cggcccggct gcgcgagggg    2640
gtgccgtcgg cgcagcagct cgagtcgcaa taccggatcg cgcccgagca tcaccggctg    2700
gtgcgccggc tgctggcgct gcgcgagacg ctgcccgcgc cgtcgcgcag cacgcccgag    2760
atcgaggccg agctgcgccg cgccctgggc ggcgagacgc gcgagctgga cctgctggtg    2820
cgctgcggcg aggtgctcgc cgacgtgctg cgcggccggg tcggcgcgct gacgctgctg    2880
ttcgagccgg cccgtacggc cgacgtggag gcggtctacc aggacagcgc tggcagccgc    2940
gcgctcaacg accggatcgc ggcgctgctg gagcggctcg cgacgtcgcg gcccgagggg    3000
cggccgctgc gcgtgctgga agtcggcgcc ggcaccggcg ccaccaccag ccgcctgctg    3060
ccggtgctgc gcggccgcgc ggccgagtac gtgttcaccg acatctccgc gcacttcctg    3120
catcgcgccc aggacaagtt cgccggcgat gccttcctca gctatcgcac gctcgacctg    3180
gagcgcccgc cgggcgagca gggcttcgag gccggcgaat cgacgtggt gatcgccgtc    3240 aacgtggtgc atgccacggc cgatatcgcg cgttcgctcg cgcatctgtc gagctgcctg    3300
accgagggcg ggatgctggt gctgcgcgag gtgaccgagc gcaggcctg gctcgacctg    3360 agcttcgggc tcacgccggg ctggtggggt ttcgccgatg cgccgctgcg cgagcacggc    3420
ccgctgctcg acgcggcgca atgggagcag gtgttgcgcg aacagggttt cgagccggcg    3480
ctggccaccg ccgaggcggg ccgcaccgag agcgtgatcg tggcgcgcag gactgccgcg    3540
agcgcggccg ggcactgcgt ggtgttcgcc gaccgggatg cctggtcggc cgggctggtg    3600
gcggcgctgc gcgacagcgg gcggcgcgtg tcggtggtgg aggccgaagc gggtgccgaa    3660
cgcgcgccgc tcgagcgcga cgatttcgcc gcgcgcctgg aagcgctgga ggccgagcac    3720
ggtggcgtcg acgaactggt ctatgcctgg tcggcacgtc cggccgcgct cgatacggtc    3780
gatcccgaga ccgccgcgga gccctatctg cgcgagccgc tcgcgctgtg ccaggcgctc    3840
ttgctgccgc gctggcgcca gctcgaggcc agcttcctga cggccggcgc gcaggccgtc    3900
gcgggtcgcg tgtccgagcc gctgcaggcc ctgctgtggg ccacctgcc cgccttcgtc    3960 aacgagaacg cgcgcttcgc gcggatcatc gacgtcgatc gcgacgagcc ggccggcgcg    4020
gccctgctcg gcgcgctcgc gcagcgcgag gattgccaga tcgcggtgcg cggcgaggcc    4080
```

```
ggcttcgtgc cgcggctgcg ccgcgccgcc ctcgtcgagg ccggcgcgcc ggtggtgtcg   4140
gccgaggcca gctacctggt caccggcggc ttcggcgcgc tgggcatcga gaccgcccgc   4200
gcgctggccg cgcaaggcgc ccggcatctg ctgctgctcg gccgccgcct gccgccgtcg   4260
gccgaagtcg cgctcgccgg cctgcgcgag cagggcgtcg ccgtgcacac gctgctggcc   4320
gatgtcggcg acgaggcgtc gctgcgcgcg gcactggccg gcgtgccggc cgagctgccg   4380
ccgctgcgcg gcgtggtgca ttcggtcggc gtgctgacg acggcgtgat cggccagcag   4440
agctgggcgc gctaccagcg cgtgctgcat ccgaagctgg gcggcgcgct gctgctgcat   4500
cggctgctcg cgccgcgccc gctcgatttc ttcgtgctct attcgtcggc ggccgggctg   4560
atgggcaatc ccggccaggc caatcacgcc gccgcgagcg ccttcctcga cgccttcgcc   4620
tggtatctgc gcggccgggg cgtgccggcc gtcgcgctcg actggggcgc ctggtccgag   4680
atcggcgcgg ccgccgcgcg cgacgtgggc gcgcggctcg gcgccgaggg ctcgatcgcc   4740
ggcgtgatcg cgcccgagca gggcgcgcc gtgatggcgc gccagttcgg ctgcgccaat   4800
acgcagctag cggtgctgcc cctgaagctg aaccagccaa tcgacgcgag ccgccagccg   4860
caggtgcggc gcctgctggc cgaattgctg gccgaggcac cggccggcgg ggcgacgcag   4920
gcgaccggcg cgggcggtgt gaccggcggc gcggcggccg atgccgaggc cggggatgcc   4980
tggctcgacc gcctgctgcg cgtgagcacg cgcgagcgcc gccgcgagct cggcgagtat   5040
ctcgaacaga cggcggaag cctgctcagg cggcccggcg cgatcgacgg gcaggccagc   5100
ctgttcgacc aggggctcga ctcgctgctc gcgatcgacc tgcgcggcac gctcgaacga   5160
cgcttcgagc agcgcttcga atcgacgctg ctgttcgatc atccgagcgt ggcggcgctg   5220
acggaattcc tgctcggcgc gctggcggag caggtgccgc gcgccgcggc ggcacctgct   5280
tcctccacgg cacatgcggc gccggcgcgc gttgtcgagg ccgacgcggc ggacgcggcc   5340
gagcccgcat cgccgaagg cgccgatcgcg gtgatctcga tggcctgccg tttcccgggc   5400
ggcgcgaatt cgcccgaggc gttctgggag ctgctggcca acggcgtcga cacgccggc    5460
ccgatcccgc ccgagcgctg ggaccactcg cgctactacg acagcgagaa gggcaagccg   5520
ggcaaggcct atgtcaagga aggctgcttc gtcgactcgg tggaccgctt ctatcccgag   5580
cgcttcggca tcgccggcat cgaggccgag ctgatggacc cgcagcagcg catgctgctc   5640
gacgtctgct acgaggcctt cgagcgcgcg gggctggatc cggcctcgct cggcggctcg   5700
gagaccggcg tcttcatggg cgtgatgacg caggactacc tgcagctgac ccagcatgtg   5760
cgcgaccacg ccttctacgt cggcaccggc actgccaaca gcatcgtctc gggccgtatc   5820
gcgcacacct tcggcctgat ggggccggcg atgaccatcg acaccgcctg ctcgtcctcg   5880
ctggtgaccg tgcaactggc ctgcgagcag ctgcgttcgg gcgcctgcga tatggcggtg   5940
gccggcggcg tgagcctgca gctcacgccc gagccgctgg tgctcgaatg cgcgggcggg   6000
atgctctcgc cgaccgggcg ctgccgcacc ttcgacgccg atgccgacgg cttcgtgcgc   6060
ggcgagggtt gcgcgtggt ggtactcaag cgcctggccg acgcggtggc ggccggcgat   6120
ccggtggtag gcgtgatccg cggcggcgcg gtcgcgcacg acggccgcgc cggcggcctg   6180
acggtgccca acgcctggc gcagcagcgc gtgctggaga aggcgctggc cgacgcgggc   6240
atcgcgcgcg agcgcgtgtc ctatgtcgag gcgcacggca ccggcacccca tctgggcgac   6300
ccgatcgagc tgaacgcgct gcaggccgtg tatggccgca cgccgcgcga cacgccgctg   6360
ctgctcggtt cagtcaagac caacatcggc cacgccgagg cggcagccgg catcgccggg   6420
ctgatcaagg tgctgctggc gatgcggcac gagaccctgc cgccgcacct gcattaccgg   6480
```

```
cgcgccaatc ccaatttcga ctggacgcgc ggcgcgctcg aggtggtggg ccagcgccgc    6540
ggctggcatg cggccgcgcc gctggtggcg ggcgtcagct cgttcggcct gagcggcacg    6600
aatgcgcatc tgctggtcga gcagtatgtc gcgccggtga cgctgcccga catgccggcc    6660
ggcttcgtgc cgctggcgat gctctcgcag gtcgatcgcg cgcagctggc cgccgacgcc    6720
gagcgttacg cggcggcgct ggccaacggc gccgagctgg ccgatctcgc ctacacgctg    6780
agcgtctcgc gcgccggcca cgcgttcag gcggtgctgc cggccggctc ggtcgcgcag    6840
ctgcgcgacg cgctgctggc gctggcggcc ggcaccgtct cgggcttcga gcggcccgcc    6900
gcgagcgtgc cgctcgaatg gcggctcggc gacggcgcgc gaccggtctg ggccgcgcag    6960
gcggtgcatt tctacgatct ctacccggcc ttccgcgatg ccgtggacgc ctgcgtcgag    7020
gggctgcgcg tccgcggccg cgccccgtc acgggccgcg cgctgtgcca gggtgatgcc    7080
gccgcgttcg aggcggcgat cctggtctat gccttcgggc ggctgctgca gcgtctgggc    7140
gtgcagcccg agcggatccg cgcgcgcggc ccgctctgct tgtggccgc cgcgctcggc    7200 ggcgcgctcg atctcgacac catgctcgac ggcctcgtgg ccgaggatgc gcgtgccgtg    7260
cgcgccgcgc tggcgcagct gggccagcgc gagagcgagg tctcgctcgc cttcgagccg    7320
cagccgtcct ggcaggtcga gctgaacgag gcggccgcgc tggcctgccg cacgcatgcg    7380
ccggcgcgca agacgacgcg catgccggcc gtgatcgacc tgccggccgc ttcgctcgac    7440
gcgcgcccgc tgggcggcct ggccgcgctg gtcgccgcgc tgccggcgcg cggccagcgc    7500
atcgactggc atgcctattt cgagccctcg cgggcacgcc gcatcgcgct gccgccagc    7560 cacttcccgg cgcgccgcta ctgggtgccg cagacggcgc cctcgacgac cccggcgggc    7620
ggcctggtcg tcgccgacct gacctccgcg cgcgacggca gccgctatgt cgagttcgca    7680
ctcgatcgcg agcgtcatcc cttcctcgac gaacatcgcc tcggccgcga caacgtgctg    7740
cccgcggccg gctcgctcgc cttcgtgctg catgcgctgg gccgcgaggc gctggcgggc    7800
ggcgtcacgc tcgacgaggt gcgcttcctg cggccgctgc gcttcggcgc gcggctcgac    7860
gtgcagctgg agatcggcgc cgacggccag gcctcgctgc atgagcgggc cgcctcgctt    7920
gccgatcggg cggcgcgggc tttcgcgacc gtcgcgaagc tgagcctggg cggcggcccg    7980
acgccggcgc aggccgaacc ctggctcgcc gcgctgcgtg ccctgcgcga gcaggcgccg    8040
gcgcgtcagg acggcgaggc cttctatcgc gatcgcctgc cgccgcagct gtggctcggc    8100
gcgggctacc ggcgcatcga ggcgctggtc tgcgacggcg gcctcgcgct ggccgagatc    8160
gccaccgtcc attcggactt cctggtcgat ccgcgcgtgc tcgacgcctg cctgcaggcc    8220
gtcaacgcga tcgacaccgg ctcggacgag ccggcgggcg cgagctacct gccttatgcg    8280
ctgcggcgcg tctggctggc cggctggccc gctggccggc gcatgcgctg cctggtcgcg    8340
catctgcccg aggcgggcgc ggccggcgaa ctggtctacg acctcgcgct gatcgacgag    8400
caggagcggg tgttcgcgct gatcgagcac gcgcgtttcc gccgcgccgc gctgctggca    8460
gtcgaggacg aggccgtgcc cgcggcgggg caggacgagg ccgcccgggc tgcgccggcg    8520
gcggccgagc cggcgatcgc cttgcccgac gagttcgccc agctgatgcc cgacgcgaag    8580
caggacctgg tcgcgcggct ggtgcgcgag ctgctggtcg gcttcctgaa gatcgacgcg    8640
ggcgccgtgt ccgacgagcg gccgttcttc gagctcggca tggattcggt gtcggccctc    8700
gaattcagcg acgagctcgg cgcctgcttc gcgctcgacc tgcatgtcga cacgatcttc    8760
gactacccga gcgtcgcgag cctgagcgcc tacctgctcg aacggctggc ggcggcacag    8820
```

| | |
|---|---|
| gcgcggcagg cgccgccggg cccggccggg caggccgcgc cggccgatgc cgccttgccg | 8880 |
| atcgacgaac tgtccgcgct gctcaggcaa gagatgggcg acgactaa | 8928 |

```
<210> SEQ ID NO 3
<211> LENGTH: 8958
<212> TYPE: DNA
<213> ORGANISM: Burkholderia ambifaria

<400> SEQUENCE: 3
```

| | |
|---|---|
| atggactcga aagaccgcga gctgctggcc aggcagcgtg atgccatccg ccagggcatc | 60 |
| cagaagatcc aggcgttgtc ggcgcggctg gaccagcccg tggcgatcgt cgggatcggc | 120 |
| tgccgcgtgc ccggtgccga ttcccccgag gcgctctggg agctgctgcg cgatgggcgc | 180 |
| gaggcgctcg ccgaggtgcc gcccgggcgc tgggatctcg acgcgtatta cgacgcgacg | 240 |
| ccgggcacgc cctacaagac ctatgcgcgc gcgcaggct acctcgacga ggtcgaccac | 300 |
| ttcgacgcgc gcttcttcgg catctcgccg cgcgaggcgc agcgcatgga tccgcagcag | 360 |
| cggctgctgc tcgaggtcag ccatcgcgcg ctggaggatg ccgagctgcc ggtcacggcg | 420 |
| ctgcgcgagc agccggtggg cgtgttcgtc ggcatcagct cgggcgaata cgcggtgatg | 480 |
| accttcgaca aggcgcgcag cgacagccag gatgcctggt cgatcacagg cacctcgatg | 540 |
| aattcggccg ccggccggct ggcctatcac tacggcttca acgggccggc actggcgatc | 600 |
| gacacggcct gctcgtcctc gctggtggcg atccaccagg ccgtgcgcag cctgctcaac | 660 |
| gaggaatgcc acaccgcgct ggccggcggc gtgaactgcc tgctgacgcc cgagccctcg | 720 |
| atcgcgctgg cgcagaacaa ggtgctcagc gccagcgggc gctgcagccc gttcagcgcc | 780 |
| gaggccgacg gctggtgcg cggcgagggc tgcggaatgc tggtgctcaa gcggctcgac | 840 |
| gacgcgctcg cgcagggctg ccggatcctc gccgtgatcc gcggcagcca cgtgaaccag | 900 |
| gatggcgcga gcagcgggct aacggtgccg aacggctatg cgcagcaggc actgatcgcc | 960 |
| accgcgctca agcgcgccag gctcgcgccc ggcgcgatcg gctatgtcga ggcgcacggc | 1020 |
| accggcaccg cgctcggcga cccgatcgag atcaaggcgc tgcagcaggc gctcggcgcc | 1080 |
| ggccgcgagg ccgggcggcc ggtgctgatc ggcgcgctga aggcccatat cggccatctc | 1140 |
| gaggccgcca gcggcgtggc cggcgtgatc aagaccgtgc tcgcgctgcg ccatcggctg | 1200 |
| ctgcccgcgc agatcaacct gggcacgccg acgccgcatg tcgactggtc ctcgggtggc | 1260 |
| gtcgcggtgg tgagcgagtc cacgccgatc gcctacggcc ccgacgcgcc gttctacgcc | 1320 |
| ggtgtcagca gcttcggctt cagcggcacc aatgcgcacc tgatcctgca ggacccggtc | 1380 |
| agcgcggtgc cggcccgggc cgaagccgcg ggcgccgcgg caacgcaggc ggtggcgcgt | 1440 |
| tcgtcgggct tgtcggcgaa ggatccggcg gcgctgcgcg agttgctggc gcgctgccac | 1500 |
| gcctatttcc gcgaggtgcc cgactgggcc gccgcctgcg aggcgctcaa tgccgggcgc | 1560 |
| gcgcattacg cgcatcgcgc cggcttcgtc gcgcgcgatc gcgagacgct gctcgagcag | 1620 |
| ctcgcggcgc cggccgccga gcggcgcgctc gaggccgatg cgccggcgcc cgacgcggcc | 1680 |
| gcgatggcct ggctgttcac ggggcagggc tcgcaatatg ccggcatggg catcctgttg | 1740 |
| tacgacacgc tgccggcctt ccgcgcctgc ctcgacgcgg ccgatcgcgc gctcgcgccg | 1800 |
| catctcggcg aatcggtgct gccggtgatc cgcggcgagg ccggcgcgct caacagcacg | 1860 |
| cgctacacgc agccggcgat cttcgcgctg cagtacgcgc tctcgcacac gctgctgggt | 1920 |
| ttcggcctga cgccgcgcta cgtgctcggc cacagcatcg gcgagtacgc ggcggcggtg | 1980 |
| ctggccggtg tgttcaaact cgacgacgcc gcgcgcatga tcgtccagcg cggccgactg | 2040 |

```
atggagcagc gctgcgcacc gggcggcatg ctggtgctgc tggccgatcc ggcgcgcgcc   2100
gccacgctgg cgcgtgccgc tggcggaggc gccacgctgg cggtggcgaa cggcccggcc   2160
agcctggtct acgcggggcc ggccgaggcc atcgagcgcc tcgcgaacgc cgcgcgcgag   2220
gcggaggtgc gctgcgtgcc gctggcggtc tcgcatgcct tccattcgcc gatgatggag   2280
ccgatgctcg ccgagttcgc cgaggtggtg cggcagacgc gtttctcgcc gccgcgtatc   2340
gccttcgtct cgacgcgct gggccggctc ccgccggcg agctgaccga tcccgactac   2400
tgggtcgccc atgtgcgcga ggcggtgcgc ttcgacgccg cggtggccgc gctgggcgcc   2460
gacccgggct ggcgtgaggc gccggcgcgg ctggcgatcg agatcggccc caacgagcaa   2520
ctgatcggca tggcgcggca gatggccggc gccgatggcg cgcagtggcg cggcctgctg   2580
cgcccgcgcg acgaccaggg ttcgttcgcc gagaccctgc gcgccgtcta cctgccggc   2640 ctgccgctgc gctggccgcg cggcatggcg cgcgacgatg cgcgcccggc cctgccgggt   2700
tacccgttcc agaggcagcg ttactggctg cccgatgccg cgccgcgtgc cgcgcgcgct   2760
gccggcatgg ttggcagccc tgaggatcgg gaaccggcgc tcgattacgc gctcgactgg   2820
atcgacgcgc cggtggcggc gccggccggg ccgccgaccg gccgctggct tttgttcgcc   2880
ggcgaggtag cgcaagccga tgcgctcaat gcctgcctga ctcgcggcgg cgcggcggtg   2940
acggtcggcc ggtcgctgac gccggtcggc atcgccgcgc tgggcggcga tctgtcgagt   3000
ttcgacgcgg tgctggtatg gcctggcgag ccggcatcga cgcaggcgcc cgagcccgcg   3060
ccgctggtcg cgctgctggc gctggtcgcg gccatcgagg cgatgcccgc cgcgcggcgc   3120
ccggcgctgc attgcgtcgg cgagatggag gccggcgctt atcggccgct ggccgcagcg   3180
ctggcggcgc tgtgccgctc gctgcacgag gaggcgcccg agctgcgcct gggcatgatc   3240
ggcgtcgatg ccgcgctcga tgccgaggcc cgtgccgccg cgctggccgg cgaactggcc   3300
gccgcgcgcg gcgtcgagtc cgagcgctgg gtcagcgccg cgggcacgcg gctgccgcgg   3360
ctcgtcgccg ccacgccact ggcgaatgtg gccgcgccga gcctgcgcgc cgatcgcagc   3420
tatctggtca cgggcggcac cggcgcgctc ggtgcgctgt tctcgcgtgc gctgatcgag   3480
gcgggcgcgc gcgacgtcgt gctcagttcg cgccgcggcc ccgatgccga ccgccgggc   3540 ctgcgtgcgc tggccgaggc gcatggcgcg cgcctgagcg tgatcgccgc cgacctggcc   3600
gatgccgcct cggtcgaacg gttgttcgcg caactggcgc gcgagcatgc accgctggcg   3660
ggcctggtcc atgcggcggg ccaggtggcc gacgcggccc atgcgcggct cgatgccgat   3720
gcgttccgcc gcgtgttcga ggccaaggtc gagggcgcgt ggcggctcga cgcggcctgt   3780
cgcgagctcg aactcgattt cttcctgatg ctgtcctcga tctcgggcgt gctcggcgcg   3840
ccggggcagg ccaactacgc ggccgccaac gccgcgctcg acgcgctcgc gccggcgc   3900 cacgccgagg ggcggcccgc gctgagcctg tgcctgggcg cggtggccgg cgagggcatg   3960
gcggccgacc cacgcgcggc gcgccacctg cagcgtgccg cgtgggcgc gatcgagccg   4020 gcgcggctac tcgcgagcgc cgcgcgctgg ttcgcgcagc cgggaccgca agcgatcgtg   4080
gcggccttcg actgggcgcg cgtggctgcc aatccgcgat ccgccgcgcg gcccttgctg   4140
caggccttcg tggcgacgtt ccccgcgcg gctgcggtta ctgcggccaa gcggcggcc   4200 gcgccggcac gcgtcgtcgc cgaggctcgc gcgccaacgc cggccgagac cggcgccttg   4260
cttcgcgaat cgatcgccga ggtgctcgac ctgcccgacc cgggcgcgat cggcgcccac   4320
gacaccctgc atgcgctcgg catggactcg atcacgctgg tcgagttgcg cgaccagctg   4380
```

-continued

```
gtgcggcggc tcggccgcga gctgccctcg cggctgctgt tcgatttccc gcaggtcggc    4440
cagttggccc gctacctggc gctcggccag cccgaggcgc cgcgcgcgca gccggctccg    4500
gccgcgcatg gcgccgccgc cgcggccggc cgcgaggaca tcgccgtgat cggcatcggc    4560
tgccgcttcc ccggcggcat cgattcgccg gagacgttct gggccgcgct cagggagagc    4620
cgcgacctga tcggcgagat cgacgcgctg cgctgggacg cgcccgcgct gcagcgcgcc    4680
ggggcgctga ccaccacgcg cgccggcgtg ctcgacggcg tcgagcgctt cgattgcgag    4740
ctgttcggca tcacgccgcg cgaggcgcag tgcatggacc cgcagcagcg cctgctgctg    4800
gagaccagct gggaggcgct cgagcgcgcc ggctacgatt tcggcgcggg cggcaccgcc    4860
ggcggcgtgt tcatcggccc cggcccgaac gactatgcgc gccgtttcgc gaccgacgcc    4920
aaggcgcttt cgcatcacca cagtaccggc aacgcactca gcgtgacggc cggccggctc    4980
gccttcgtgc tcgactggca ggggccggcg ctggcggtcg acaccgcctg ttcctcgtcg    5040
ctgatggccc tgcacctggc ggtacaggcg ctgcgtcgcg gcgagtgctc gatcgcgctg    5100
gcgggcggcg tgaacctgct gctctcggcg gaaacctcgg tgctgctgtc gaagggcggg    5160
atgctcgcgc ccgacggccg ctgcaagacc ttcgacgcgg ccgccgacgg ctatgtgcgc    5220
agcgagggct gtgcgatggt ggtgctcaag cgcctgggcg acgcgctggc tgccggcgac    5280
gaggtgctgg ccgtggtgcg cggctcggcc gccaaccagg acggccacag ccaggggctg    5340
accgcgccga acgggcaggc gcagcagcgc gtgctgcgca acgcgctggc cgatgcggcg    5400
ctcgatcccg cgcgggtcgg gctgctggag gcgcacggca ccggcacgcc gctaggcgac    5460
ccgatcgagt tcgccgcggc gcgtgccgtg tacggcgagg cgcccgggcg cgaggcgccg    5520
ctctggatcg gctcggtcaa gaccaatctc ggccatgccg aggcggccgc cggcatcgcc    5580
ggcttcatca aggcggtgct gtgcctgcgc acgagatga tcgtcccgca cctgcatttc    5640
acgcggctca atcccgagat cgaactcgat gaagccgcaa tgcggatccc gggcgcgacg    5700
gccgcctggc gcggtgccgg gcgttacgcg cggtcagct cgttcgggtt cagcggcacc    5760
aacgtgcatg tggtgctgga ggcggcgccc gctgcggccg gcgtcgaggc acgggagcag    5820
caggggcagg aacaggtacc ggtaccgggc gcggagctgc gcatctcggc ggccagcccg    5880
gcggcgctgc gcgcttatct gctggcctat cgccaccgtc ttgccacgct gccgccgcag    5940
cgctacggcg cgctgctcgc gggtgccgcg cgccgggcgc ggctcgcctg cacgcgcagc    6000
ttcgccgccg cgaacgcggc cgaggcgctg ccgcgatcg aggccgcgct cgccgagatg    6060
agccccgaag ccggcgccgg ggcgtgcggc gaaaccggcc cgcgcgtcgg cgccgatctg    6120
ccgcgcgatg gtggccccga ggtgccggtc tatccgttcg accggcagcg cttctggctc    6180
gcgccgcgcg cggccgaggc gcaggtggag gcgcaggtgg aggcgcccgg gcccgcagcg    6240
cagcttggcc tgcgcctgac ggccagggac gcgcgccagg tgatctacgc gctcgactac    6300
gcgagccggc cgccgttccg gctcgacgag cacctcgtgc atggcgagcg cgtggtgccg    6360
gccgccgcgc atctggcgct gatcgtcggg atgttgggcg agctgcgcgg cgagcgcggc    6420
tggacgctcg ccgacgtggt ctgcgagacg cgctggtcg tcggcgccga cagcgaggcg    6480
gtgcgctacg tgttcgatgc cgagcccgat gccggcgacg gcggcgcggc ctatcgcgtc    6540
gcggtgctgt ccgacggcga gggccgcacg cgctgccacc tgcgcgccga ggcccgcgcg    6600
ctgccgcgcg aggcgcaagc gcttgagccg agccgccgcg tggtcgcggt tgcgccggcc    6660
ggcgcggcgc tgcccgcctt cgacggcgcg accttctacg accgcctcta tgggaccgag    6720
atcggcctgg ccggcgcgtt ccgcggcgtg ctgtcgatcg agcagcacgt cggccaggcg    6780
```

```
cgcgcggaac tggcctggcc ggctgcgggg cagccgctgg tgccgggcgt gctcgactcg    6840
ctgttccaga ccatcgcgct ggccacgctg gccgaccagc cgggccacag ccacatgaac    6900
ggcgcgacca ttccgttcgc gatcgatcga ctggtggtgc tgccgcgcgc ggcatccacg    6960
ccggcgccgg tgatcgccaa tacgcggctc gtcagcgaga cgccgacgg cgcgagcttc    7020 gtgcacgacc tggaggtggc cgaggcgggc cggccgccgt tcctgcgtgt cgagggcctg    7080
ctgacgcgac gcgccgccgc ggcgcaattg cgccgcgcgg ccgagcgctt gccgcaactg    7140
gtcgagcact gggtcgaacg ccgggtcgag catgaaacgg cgccgtccat cgcgccgcgc    7200
ctggtgctgc tcgacgaggc ggcgcgcacg accgcgcgat cctggctggc cgcctcgggc    7260
gaggtcatcg atgcgagcgg gcttgacgac gccgccgtgc tcgcggccct gggcagcgag    7320
ccggcggtgc tgctggctgg cctgccggcg gctccggcgg cggaccagga cctcgcggct    7380
gaatcctggc gcatgccgct cctgggcctg gtgggcgccg tgccgccgcg cgacaggctc    7440
ggcgacgcgc tcgaggcggc gggtgccacg gtgcgcttcg gcctgctgtc ggaggcccag    7500
gccgatctcg acgggcaggg cggctcgccg ctccatggct tcgcgctcgg cctcgccaag    7560
tcgctgagcc tcgaatggcc gggacgcgcc gtcacgctgc tcgacgtgga tgggggagggc    7620 tcgccggcgg atgccgccgc gctcgcggcc gaatggcgct cgccgcgcgg cgagtgcatc    7680
gcctggcgcg gcgccgccg ccatgtgcgc gcgttaccg aactcgccgc gccgccgctc    7740
gcgtcgtgcc agccccgcgc cgacggcccc tacttgctga cgggcggcct cggcgacctg    7800
gcggccgaga cctgccactg gctcgccgac gagggcgtgc gtcatgtctg gctgaccggc    7860
cgtcgcgaag ccgacgcggc gatcgagcgc cagctcgacg cgctgcgcga ggcgaccggc    7920
ctgcgcgtcg actaccgcgc ctgcgacatc gccgatcgcg acgcgctcgc ggccctgttc    7980
gcggatgccg cgcgggacgg tccgctgcgc ggcatcttcc actgcgcggg cgtgctcgcc    8040
gacggcgcct tcgccacgct cgacgacggc gccttcgagc gcgtggcgcg cgccaaggtg    8100
ctcggcagct ggaacctgca ccagctctcg cgcgggctcg atctcgacgc cttcgtgctg    8160
tattcgtcgc tggcctcctt gctgggctcg gccgggcagg ccaactacg ggccgccaac    8220 ggcttcatgg atcaactggc gcgctcgcgc gcgcgctcg gcctgcctgc gctgtcgctg    8280
aactggccgg gctggggcgg cgtgggaatg gccgcgcgta acgcccgcgg cgagcccggc    8340
agcggcctgc gccggctggc gccggagcgg gccctcggcg aactgggccg ggcgctggcg    8400
ggcgggcagg cccagtgggg gatcgccgat gtcgactggt cggtgttcgg ccgcgactgg    8460
cgcgcgtcgg ccgcggccgt gccggccctg gtggaggact ggttcgccgc gcatccgcag    8520
gcggcgccgc ggcaggcgct tgccgccgcc ggcgcagtgc ccgccgaggc cgcccgcgag    8580
cttgccgcgg cggtggacgt ggacgcccga ctcgagatcg cgcggcgtca cctggtgggc    8640
atcgtgcgcc ggatcatggc gctcgacgcg gcccggccgc tcgctcagaa caagtccttc    8700
cacgagctgg gtctcgattc gctgatggcg atcgagctca agcgcgcgct gcaggagggt    8760
ttcgcggccc gcgtgcctgc caccgtgatg ttcgactacc ccgatatcga cagcctcgcg    8820
cactggctgg cggggcccgc gcaggcggct cgggccccgg cctcggcttc agccgccgacg    8880 ccgcgtgccg cgcctgccga cgcgctcgat caactggacg aaggcgaact ggccgacgtt    8940
ctcgacaaat tgctgtga                                                  8958
```

<210> SEQ ID NO 4
<211> LENGTH: 6066
<212> TYPE: DNA

<213> ORGANISM: Burkholderia ambifaria

<400> SEQUENCE: 4

```
atgacggaca tggacaagga cctgctgctg caatcgatcc agacgatccg cgaactgaag      60
acgcggctcg cgcaggccga gcaaggccat cacgaggcgg tggcggtggc ggtggtcggc     120
gtgtcgctgc gctttccgg aggcgtgacc gatctcgaca gctactgggc gctgctgcga      180
gaaggccgca gcggggtgat cgaggtcgag cccgaacgct ggagcaaccg ccagttcgtc     240
gatcccgact atgccgccgc cggcaagctg gtgacgccgt atgcgggact gctggagcac     300
atctacgatt cgacgccga attcttcggc ctgtccgcgc tcgaggccga gaacctcgat      360
ccgcagcagc ggctgctgct cgaacagagc tggctcgcgc tcgaggatgc cggctacgac     420
atcggccggc tgcgcggcag cgataccggc gtggtggtgg ggatcggcag ccaggattac     480
ggcatggcgc tgctggccga tcccgcccac gcgaatccct acgtggcctc cggcaactcg     540
ttgagcatgg cggccgggcg gctgtcctac ttcttcgact tcagcggccc ctcgctgtcg     600
atcgacaccg cctgctcgtc ctcgctggtg gccgtgcacg aggcctgccg cgcctgcag     660
ctgggcgaat gcggcctggc gctggcggcc ggcgtcaacg cgatgctgac gccgcacgcg     720
ggcatcaact tctcgcgcgc acggatgctg agcaccgagc gcgactgcca taccttcgac     780
gcgcgcgcca aggggtacgt gcggcggag gctgcgcgg tgctggtgct caagcgcctg       840
gccgacgcgc aggctgacgg cgaccgcatc cacgccgtga tccgcggcgt ggcgatcaac     900
cacgacggcc acagcagcgg cctgaccgtg cccaacggtt cggcccagcg cgcggtgatc     960
cgcgcggcgc tgcggcgcgc cggcgtggcg cccgccgagg tcgactacgc cgaggcccat    1020
ggcaccggca cgcggcttgg cgatccgatc gaggcgcatg cgatcgccga cgtctacggc    1080
gaggcgcgca aggcgggccg cccgctcgtg atcggcgcgg tgaaggcgaa cctcggccat    1140
ctcgaggccg cggcgggtct ggccgggttg atcaaggcga tgctggtggt gcgccacggc    1200
gaggcgccgc cgcagcccgg cttcgagacg ctgaatcccg cgatcggctg gataccgcg     1260
aagttcaagg tggtgcggca gcccacgccg ctgcggcccg ccgacgggcg ccctggctg     1320
gccggcgtca gcagcttcgg cttcagcggc accaacgcgc acgcgatcgt cgcggcggcg    1380
cccttggcgg ccgaggaggg cgagccggcg gccgagccgc cggcggccct gcacgtgctc    1440
gcgctgagcg cgaagacgcc cgaggcgctg ggtcgtcatg tcgaggaagt ggccgcctac    1500
ctggccggca gcccgcagc cgagctggcc gcgatcgcgc aaacctcgac ctgccggcgc    1560
gtcgcgctcg cgagcggat cgccgtgacc gggcgcgacg cgccgagct ggccgcgcgg     1620
ctaaggcgcg cgctggccga gcgcgcgccg cggcgcgcgc cgggccgcat cgtgctctac    1680
ctgtcgagcg ccgacctgcc ggccggcacg gccgacccgg ccgcgctggc cgccttgcat    1740
cgcggctggc tggcgcgctg cgccggcttc ggcctgttcc ccgatcgggt ggtgctgcgc    1800
ggcatcgcgc ccgccttcgt gcgcgcctgg ctctggcagc atgccgagcc caccgggctc    1860
gcctacctgg acgagacggc cggcgacgcg ctgcgcggct tttccaccag cgagacggcc    1920
gccggcgagg tcattgccgc agaggcggca gcggccgagc tgttcgagga cgcggaggtg    1980
ctcgcgctcg gcgcgccgcc gtttgccttg ccggcctcgt cgtcgacccg ctggttgcgc    2040
ctcgacgacg aggccgcact gcgcacgacg cttgccgcgc tcttcacggc cggcatcgag    2100
atcgactgga cgccgctcga tgcgcgacgc catcgcgtgg tccgcgactt tccgcgccgg    2160
cccttcgcac gccgaagctt ccgctcgcct cgcatcgacg cggcactggc cggcgccgac    2220
gcgccgcgcg agagcgaaag cgcgatccat ccgctggtgc gcgatcgcct ggcgcagccc    2280
```

```
gacggccgcg tgagctgccg cctgcgcacg gccacggcct ggctcgattt catcgacggc   2340
caccgtgtgc agggggcatcg tctgctgccg gcctcgctgc tgctcgaact gatgcgcacg   2400
gcggcggccg atgcgcgcgg cgcggcggtg acgctcagcg acgcgcgctt ccggcgcccc   2460
ttcgatctcg acgcggccgc ctgcgattac ctggtccagg tcgatgcgcc gggcgagggc   2520
gcgcgcgtcg ctctgtgggg ccggccggcc gacgatgcgg cggcgccctg ggtcgagcat   2580
gcgagcgccg cctgccgcct cgccgagacg acggatgcgc aggacgcgcc gccggccgag   2640
gtcgaggccg aaggccgcga ctggcccgcc gagggctggc acgaactcga tgtcggtgca   2700
ctctatgcgc gccaccaggc cggcgacatc gtgctcggcg aggatttccg ctgcctcgcc   2760
gccttgcgcg tgcggggcgc gcgcagcgag gccgaggtcg gcccgccgcg gggcgccagc   2820
cacgacgcga cgcagcgtgc cgccctgctg atcgatgcct gcctgcaggc cagcgccgcc   2880
acgcgcgagg tcgacgacgg cctgttcctg ctggccgggg tgggcgaggt ggtgctgccg   2940
cccgccgtgg ccttgcccga gcgcctgcgc gtgcggctgg tgcgcgaggc ttgcgacgag   3000
ggctatcgct tcacgatcat gctggccgat gccgaaggtg cgccggtcgg ccggttgcgc   3060
gaggtgctgt tccggcgcgt gcagggggca cagcgcgccg cgccgttcca cgagaccggc   3120
tgggaagccg tcgagtggcc ggcgcgcgcc gccgcgccca tgcatgcggc gctgccggcc   3180
ccggacgcgc tggatgggct cgaggcttcg gccacctggg ccgcgcgctt cgggctcgac   3240
agctacgacg cctatcgcgg gcagatcgag caggcctgcg ccggcatcgt ggccgacacg   3300
ctagccgatc tcgggcacga gggcgccgac atggaagccg ccgacgtcgc gccggcccag   3360
cagcggctgt tcgcgcacct gctcgcggtg cgcgcgcgcg gcgacgccgt tgcactcgcg   3420
gcgggcgccg cgcggctcga cggcgtcgcc gcggcgttcc cacagttcca cggcgagacc   3480
gaattcctgc gccgctgcgc cgccgccttg cccgaggtgc tgcgcggccg cgcaatccg   3540
ctcgaggtgc tgttcggcgg ttccgcgttc gacggcagcg aggccgtcta cgtcgattcg   3600
ccgatcgcgc gcgtgctgaa cggccagctc gcgcaatggg ccgcgcggct cgccgcgcaa   3660
cggccgctgc gcatcgtcga gatcggcgcc ggcacgggcg gcacctcgcg caccgtgctc   3720
gacgcgctgc gcggcctgcc ggtggcgcgc tactgctaca ccgacgtctc gccgctgttc   3780
ctcgaacgcg cgcggccgcg cttcggcgag gagggcttca tcgactaccg cctgctcgac   3840
atcgagcagc cgatcgccga ccagggtttc acggccggca gttcgacct ggtgatcgcc   3900
gccaacgtgc tgcatgcgac gcgctcgatc gccgacacgc tgcgccaggt gcgcgagctg   3960
ctggcgccgg gcggctacct gctgctgcgc gagtgcacgg cgcagcgcct cagcgccgac   4020
ctaagcttcg ggatgaccga gggctggtgg cgcttcgagg accacgcgct gcgcgccgac   4080
tacccggtgc tgtcggtcgc gcaatgggag cggcaactgg ccctggccgg cttcgagcat   4140
acgctcggcc tgccgccgag cgaggccagc gccgaggcgc tgatcgtcgc gcaggcctcg   4200
gccgtcgatc gcgcggagca ctggctggtg gtgcacgacg gcagggcgt cggctgcgtc   4260
gcgcagctcg cgcacgagcg gatcgcgtgc cgcgagctgt cctgggccga ggcgctggag   4320
gccgatccgg cgcgcgaaag ctaccagcac atcgtctgct tcgccgatgc cggcgagcgc   4380
gacaacgccg atcccgtcgc ggcggccacc gcgcagtacg aggccatgat cgcgctgtgc   4440
cggcgctggc tcggccccga ggccgcgccc ggcgcgcgcc tctggtgcgt gacgcgccag   4500
gccgagcgcg ccgtcgatgc cgaccgcgtc gacgggctcg ccagtcggt ggcggccggc   4560
gtgctcaagt gcgccgcgct ggaattcccg ggccgcgtcg ccggcctggt cgatctggag   4620
```

```
gccgagccgg ccgatttcgc ctcgctcatc gcgcattggc gcgagccggg cgagctgcgc    4680
tgcttcgcgc tgcgcggcgg ccggcccat gtgccgcgcc tgcggccgct cgatgccggc      4740
gcgctcggtg cttcgtcgtt ggccggcggc gctgccttcg acggcacggt gctgatcacg    4800
ggcggtttcg gcggcatcgg cctggcgctg cggacacgc tggccgcgcg cgtcgagacg      4860
ctggtgctgg tcgggcgcca ggtcggcggt cccgagcgcg aggcgcagct cgccgcgctg    4920
cgcgaacgcg gcgcgcgcgt gatcgcgctg gccgccgatc tcgctgacga ggcgcaggtc    4980
gcggcgctgt tcgcgcggct ggtcgccgag ggcgtggcgg tctcgcacct gatccacgcg    5040
gccggggtgg gcggcagcct ggcgctggcc gcgagcgggc gcggggaact gcgcgaggtg    5100
gtcgacgcga agctggccgg cacctggcat ctgcaccggc atgccggccc gtcgctgaag    5160
tccttcaccg tgctctcgac catgctcgca ctgtggggcg cgcgcgagaa ggcccactac    5220
acgctggcca atcacttcgc cgagcgcgtc gtcgaatggc gccgcgcgcg cgggctgccg    5280
gcctcgatcg tgcacctggg cccgatcgac ggcggcatgc tcgacgcggc cggcaaggcc    5340
gccgcggcgc gcgtcggggt gcgcagcttc acgctgcgcg agctggccgg ctggctcgcc    5400
gcgccgctgc cgcgcgccgg catcgcgcta ctcgacatcg actgggcccg cttccggccg    5460
atctaccgcc acgctggct cgacgcgctg ttcgccgaac tcggcacgcc cgccgacggc    5520
ggtgcggccg gtgccaaggc cgccgatggc gcggccgcgt tccggcgtgc ctacgcggcg    5580
gccggctacc gcgagtcgat gctcgacgaa ctgctgcacg cgctgctgcg cgaggtgctg    5640
ggcctgtcgg gcaacttcgc ggcctacgcc ggcacgggct ccacgatct cggcatggat    5700 tcgctgctga ccctgtcgtt cgccgagaag ctcggcgcgc gcgtcggctt gccggtgtcc    5760
tcggtcgacg tgtttgacaa cgcgaatccg gcgcgcttgc gcggctggct cgcggcgcgc    5820
ctgaaggcgc tctacgcggc cgcgccggcc gctgccggca gcaccggtaa cgctggggct    5880
actggtgcca ccagcgcctt cagtgccgcc gatgccacgc atccggacgc gaccgacgcg    5940
ccgccgcccg ccggccgct ggccgccact gtctccccca ccgcgagcga cgccgccggc    6000
gatgccgtga ccgatgaaat cgaacgcgag ctgcagacga tgcaggcgct gctggaggac    6060
cgttga                                                                6066
```

<210> SEQ ID NO 5
<211> LENGTH: 5238
<212> TYPE: DNA
<213> ORGANISM: Burkholderia ambifaria

<400> SEQUENCE: 5

```
atggggagga ccgtggcaca ttttctcgat cggatcgaac aactgtcgaa gccgcagttg     60
caggcgctcg cgcgtgcgat gcgcgacgag atcctgcaac tgcggcccga cgagcgggcg   120
gatgccgcgc cggcagacat ttcagggctg gcctacgaga cgcgctggca gatcgcgccg   180
ccggccctcg ccgcgatgaa cccgggccga gccggcgcgc cgcgcgtgct gctgctgaat   240
tggcgcgacg ccgcctggcc gccggccggc tgcgccgcga tcgcctcctg cgtgacggcg   300
agggcgacgc tcgatcccga caccggttgg gcgcccgagg cactcgccgc gcaactgatg   360
cggctcgcgc aggcctcggg gccgttcgac gcgatcgtgc ttgccgtcgg cggcgatgcc   420
catggcgcgg cggcccgcgg cgagccggat gcagtgacgc tggccgcgca ctggggcacc   480
gcgttggcgc tggccgccgc ggtggccggc caagtggcgc cggcgcgcct gtggttcgtc   540
acgcgcggcg cccagtgcct gccgacgat cgcctgccgg ccgacccggc gctggcgccg   600
ctggccgcgc tgggccgcac gctctcgctc gaactgccgg ccgcctgggg cggctgcctc   660
```

```
gatctcgacg aggcgccctc ctcgctcgaa cgtgccttcg acgagatcgc ccgcgacccg      720
ggcggcagcg acgacgaagt cgcctatcgc gccggccagc gctacctgcc cgtgctcgaa      780
cgcgtgtccg aggcgccgcg cgcgcccttc gtgccctcgt ccgaggccag ctacctggtt      840
accggcggca cgggcggcat cggcaccgtg ctggtcgacg acctgctcgc gcgcggcgcg      900
gggcgcgtgg tggtgctcgg gcggcgcgcc ccgccgcgc ccgaggcggc ggcatggctg       960
gccgcgcgac ggcgcgccgc cggccgggac gaacgcgtca ttctggtcgc ggccgatccc     1020
gccgaccggg ccgcgctcgg cgcggcgctc gacgatatcc gccgcagcgg cccgccgctg     1080
cgcggcatct tccacgcggc cggcagcaac gaacggatcg cgctggcgcg cctcacgcgc     1140
gacgacatcg cgcgcatcgt cggcgccaag gccttcggcg cgctgcatct cgatcagctg     1200
acgcgcgagg acgcgctcga tttccaggtc tactttcgt cggtcgccgg ccgctggggc       1260
accgcgcaga tggcacccta cgcgatggcg aaccgctttc tcgacgcgct ggccgagcgc     1320
cgcgaggccg agggacgccg cacgcgcagc ctggcctggg ggccgtgggc cgaggtcggc     1380
atgatggtcc ggcagcggca gcaaggcttc ggcgcgctcg ggctgcgcgc gctcgcgccg     1440
gggctcgggc tcgccgcgct ggcgcaggcg ctcggccagc ccggcatcgc cggcgccacg     1500
cggcagatcg tggatgtcga ttggccgtgt tatgccgagc aggtcgcggt ggccaagcat     1560
ctgcgtccgt tcgctgccct gagcgccgct gcgtcggcgg cttgcgcgac ggcatccggt     1620
gccgcgccgc cgctcgacgc cgtgccttcc gccgccgagg atttcggtca ggccggggca     1680
acgctggccc tgctgcgcga actggtggcc gagctgaccg gcgcggcgct gcccgagcgc     1740
ggcgaggcgc ggccgatgca ggaactcgga ctgacctcgc tgctgagcat cgagctgagc     1800
cagaagctgc gccagcgcct aggcgtgcct tgccgcccga ccgtggtgtt cgatcatgcc     1860
aacctgcgcg cgctggccga gtcgctggcg caggcctggg cgcacgccaa tccgcgcccg     1920
gcggtggcgc tcgcgcgggt gggcgccgcc agcgcccgtg ccgccgatgc cgacgagggt     1980
gcgatcgcga tcgtcggcat ggcctgccgg ctgcccggcg ccgattcccc tgacgcgctg     2040
tgggcccaac tgatgcaggc cgaggccgtc gcgctcgacc cggtcgagtc gaggcccgcc     2100
gcgcgctttg acctcgcgcg ctacctgtcc gacgaggatg cgccgggcaa ggcctacagc     2160
ctcgcgggcg gcttcctcga cgacttggag cagttcgacc acgcgcgctt tcgtctttcg     2220
catcgcgagg cctgcttcat ggacccgcag cagcggctcg cgctggagac cacctggcgc     2280
gccttcgagg acgtcggcat cgatcccgct gcgcggctcg acggcagcgc cgccgacgcg     2340
ctcgacgcgg ccgtgttctt cggcatcggc cagaacgaat acggcccgct gtccgctcg      2400 gtggccgacg gcgaggatgc cgggctgatg tcgaccggcc agtcgatgaa catcatcgcc     2460
gggcgcgtcg cccacctgtt cggtctggac ggccgcgcga tctgccacga caccgcctgc     2520
tcgtcctcgc tggtcgcgct cgacgcagcg gtgcagcacc tgcggggcgg ccgcaaccgg     2580
ctggccgtgg tcgcggcgt caacgcgctg gtctcgcccg acaccttcgt gctgctcggt      2640
aaggcgcgcg cgctgtcgcg gcagggccgc tgcgccgcgt tcgacgcacg cgccgacggc     2700
tacgtgcgcg ccgagggctg cgtggtgatg gtgctcaagc ggctggccga cgcgcgcgcc     2760
gacggcgacg cgatccatgc cgtgatccgc ggcagcgcgg tcaaccacga cggccgcagc     2820
agcggactga ccgcgccgag cggcgcggcc caggagcgcg tgatgcgcgc cgcgctgcgc     2880
gacgccggcg tggccgcgca cgaggtgcgc ctggtcgagg cgcacggcac cggcaccgcg     2940
ctcggcgacc cgatcgaata ccacgcgctg cgcgccgtct acgccgacga tgcgccgcgc     3000
```

```
gccacaccgc tggtgctcgg cgcgctgaag tctttcatcg gccataccga ggccgcctcg      3060
gggctggccg gcctgctcaa gctggtgctg agcctgcgtg cgcgcatcgc gcccgcgcag      3120
cggcactacg tcacgccgaa cccgttcatc gagaccagcg agcggatcga gatcccgcgt      3180
ggcgcgcgcg cgctcggcgg tgacgggcgc gtgctgggcg ccgtcagcgc tttcggcttc      3240
aacggcacca atgcgcacgt gatcgtcgag cgcggcgagg agcggccctc gcggcgcctg      3300
cccggcgcgc cgttcgcgcg ggtgcgctgc tggtactcgg cgcgcccgct gtcggccagc      3360
agcgggctcg cgcaggcctt cggtgccgcg ccggcgagcc tcgcgccggc cagctacgtg      3420
acgcgctggg cgccgttcgc ggccccggcc gccgtcgcga tgcggcaggt gctggtgctg      3480
cgcatgccgg tcgcggccgg tgatccctg tacgacgcgc tggatcgcgg cctgatcgag      3540
gcgatgcgcg cgcgcggcat ccgcgtgatc gaggccgacg cgagccggc cccgggcctc      3600 ggcctggcgg cggtgctggc cgcgcagaca gccgcgcacg tcgcttcga gcgcatcgtg      3660 ctgcgtctcg gcgacggcgc cgcctggccc gacgcggcgc tcgacacggc ctggctggag      3720
cgcctcggcc acggctggtc cgcgctcgcg agcctgccgg ccgaggcccc gccggtgctc      3780
gtgagcggcg ccgcgcaacc cgctggccg gcggtgctgg cctgcgtcga caaggagcgc      3840 gcgggccgg cccctcacctg gctcgactgc gaaccgggcc ttggcgaggc cgggctcgac      3900
agcctgctcg acgcccatct cgatgcgctg ctcgcgatcc gcgaaccggc ttgccggctc      3960
acgcgcgcgg gcctcgtggt ggcgcgcctg gccgccgccg cgccgctgcc tgccgccgcg      4020
ttccgcgcgc gcgacgcgca tgcctatctc gtcagcggcg ggctcggcgg ggtcggcgcg      4080
cgcgtgctcg gctggctgct cgaacaaggc gcgcgtcatg tcgtcagcct gaaccgccgc      4140
gcgcccgatg ccgccgaagc agccgcgctc gagcgcctgg ctcgacgcca gccgcgcgc      4200 atcgacacgc tggacctcgg cctcgacgat cccgaggcct tgcgcgaggc gctgcgggcc      4260
acgctcggcg gcacgccgtt ggccggcgtg ttccattgcg ccgccgtgct cgacgaccag      4320
ccgttcgcgg cgcaggcctg ggacgcggcg cgggaggtgc tgcggcccaa gggcgccggc      4380
gcctggcatc tgcaccgcgc cacgctgggc cagccgctcg atcacttcgt ggtgttctcc      4440
tcgctgtcgg cgctgctcgg ccagccgggg caagccgcct acgcgctggc caatgcgctg      4500
gccgaggccg tggtcgaacg gcgccgcgca ctcggcctgc ccgcgctggc gatccaatgg      4560
gggccgtggg ccggcgtcgg catggcgcg cgcggcggcg aggcgctggc cgcccagtac      4620
cgcgcgatcg gcctggccgc gcgcggcgcc gacgactatc tgcgcgtgct gtcggcgcgg      4680
ctcgcgtccg gcgcggggcca ggaagcctgc gtcggcgtgt tcgatctcga ctggcggcgc      4740
catgcggcca cctacgcgcc ggcgccgctg tgggccgggc tgctgggcga tggcggcgcg      4800
ccggccgagc cgcccctcgt tcgccgagcgg ctcgccgagg tgccgcccga gcggcgccgg      4860
cgtgccctgc gcgcgcggct gcgcgagatc gtcgccgcct gcatcgggcg cgacgccgcc      4920
gcgatcaccg ataccgacgg ctttgccgag atcggcatcg attgctgca cgccacggtg      4980 ctgcaccggc agctcgaacg cgaattcggc gccgcgctgc cggccaccat cgccttcgat      5040
caccccacgg tggccgccgt cgccgactgc ctcgcgcgcg tgcgctggc cgagctgttc      5100 gcgccggcca tcgtggccgc gccgcgcag ctggcgaacg ccgcggccga cgcatcgctg      5160
ggggaccaca gtgccgccga actcgcccgg atcctcgcgc acgagctcgg cggtctcgaa      5220
tcacgcggag cactttga                                                   5238
```

<210> SEQ ID NO 6
<211> LENGTH: 6606

```
<212> TYPE: DNA
<213> ORGANISM: Burkholderia ambifaria

<400> SEQUENCE: 6
gtgaataagc ccacctcgtc cgacggctgg aaggacgact acctgagccg gctgtcgcgg      60
ctgtcgaaga accagctgat ggcgctcgcg ctcaagctca agcagcagca actcgagcag     120
gggcccgcgg ccgagccgat cgcgatcgtc ggcgtcggct gccggctgcc cggcggcgtg     180
gccggcccgg acgactactg ggcgctgctg cgctcggccg gcagtggcat cgtcgagatg     240
caggaccagc gctggaacat ggccgcctac ttcgatgccg atcccgaggc gggcgggcgc     300
attcatacgc gttcgctggg cctggtcgac gaggtcgacc gcttcgacgc cgacttcttc     360
tcgatctcgc cgcgcgaggc cgagtcgatg acccgcagc agcgcctgct gctggaggtg     420
gcctgggagg cgatcgagcg cagtggccac gcctgcgcct cgctcgacgg cgccaggtg      480
ggcgtgttcg tcggcatgat gaacaaggac tacctgcacc tgaacgcgcc ggacatcacc     540
ggcgaggcgc acggcattc gccctattac gcctccggcg aggccttcag catcgcggcc      600
ggacgcctgg cctacatcct cggcgtgcac gggccctgca tgacgatcga caccgcctgc     660
tcgtcctcgc tggtggccgt gcatctcgcc tgccgcagcc tgctcgagga cgaatgcgag     720
ctggcgctgg ccggcggcac ctcgctgatc ctctcgccgg aagcctcgat cgtcagctcg     780
aacgcgcgga tgctgtcgcc caccgggcag tgctggagct cgatcatcg cgccgacggg      840
tacgtgcgcg gcgagggctg cgccgtggtg gtgctcaagc gcctgtcgcg cgcgctcgcc     900
gacgcgacc cggtgctggc cgtgatcgcc ggctcggccg tcaaccacga cggccgcagc      960
cagggggctga ccgcgccgaa cacggccgcg cagatggcgc tgatgcgcga ggccctccgc    1020
ggcgcgaaac tcgatgccgc cgcgcatccgc tacgtggagg cgcacggcac cggcacgccg    1080
ctgggcgacc cgatcgagat gaactcgatc caggccgtct acggcgaggc gcgcgacgag    1140
gcgtcaccgc tcgtgatcgg ctcggtcaag acccagatcg gtcacaccga ggcctgcgcg    1200
ggcgtggccg gcctgatcaa gctcgcgctg tgcgtcgcgc acgatcgcgt ggtgccgcag    1260
cgcaatttcg agcggctcaa cccgcatatc acgctgcgcg atggcgtgcg gctcgcgctg    1320
cgcgacgagc cgttcggcgg cgaggccggc gcgcgctacg cgccgtcaa ttccttcggg     1380
ttcagcggca ccaacgcgca cctgatcgtg cgcgacctgc cgcccgccgc gccggtggcg    1440
ccctcgctgc gcgggccggg cgtgctggcc gtgtcggcca ccaacgccgc cgcgctcgac    1500
gcgctgctgc tgcgctaccg cgattacctg gcgccgggcc ggcccgagcc ggactgggat    1560
gcgctggcct ataccagcca ggtgggtcgc aaccatttcc gcgaacgcgt ggcgctgacg    1620
gccgacgaca tcgccgggct gcgcgcggcg ctcgatgcgg ccatcgcggc ccgtgccgcg    1680
gccgccgcga cggcgcatga cgagtggccg ccgaccgccc gcgcgggctg ggtattcggc    1740
gtcttcgaca tgacgccctc ggagttggtc gcgcaactgc ggcggagcag cggcgccttt    1800
gcacggcggt tcgacgcgct ggtggcgcgc cggcgccgg agctggcggc tcgcgacgat    1860
gtgctcgcct acctgaccgg ctgcgcgatc gtcgagaccc tgcacgacgc gggcctgcat    1920
gccgacgcgc tggccggtgc cgatccgctc ggcaggctgg tggcggcaac tgctgccggc    1980
ctggtgagcg tcgataccgt gctcgcctgg ttgccactcg atgccgccgc gcgcgacgtc    2040
gcactggccg attggccggc gctgccgccg gaaatcgcgc tggtcgatgc cggcagcggc    2100
gagagccgtc tcgatacctg gcgcgatgcc gcgcgccgcc gcgcctggct cgcgcagccg    2160
gtcgagcccg tgccggcggc gcaccaaggc ggggacgagg cgatccgctg gctggcgatc    2220
```

```
ggcgacctga atgcggcggc gggcaagagc ccggccgccg cgccgttcct gttcccgcgc    2280
gagttcgcct cgcgctcctg gaccccgcc tgggccatgc tctatcgctc gggcctgtcg     2340
ctcgactggt cggcgctgta cggcacgacg cgtccgccgc ggctggtgtt gccgacctac    2400
gcgttccagc ggcggcgcta ctggccgcgc aacgccaagg tcgagcagct gcgggcgcct    2460
gcgcgccagg cgagcgccga attccggctg gtctggcagc ccgccgccgc gccggtcgac    2520
atatcggctt ctggcgcggc tcccgcgcgg cgtcgcatcg tgctggctga acccggcgcc    2580
tggtcggatg cggccgagct gccagcgggt ctgcagtggc tgccgctgcc cgagggctgg    2640
cgcgacgcgc aggtgctggc cggcctgctc gcctcgctcg aacctggcgc cgcaggcgct    2700
gcgctcgacc tgctgttctg gctgtcgccg tcgcgcgtcg aacgcgacga tgccgcgcgc    2760
cgcgccgccg acaccacgcg cggcctgtgc gtgatcggcc aggcgctgct cgcgctcggc    2820
gagtcggcgg gaatgcggat cggtttcgcc accgagggcg tcgagcaggt agtcgaggcc    2880
gatgcgcggc aggcccgaa cgtcggcgat ggcgtggttg ccggcttcgt caagacgctc     2940
ggcttcgagc agccgcaatg cgtccctgg gtcgtcgatc tcgatgcgcg cgctgacggc     3000
gccgcgcaga tcgtgctggc gctcgatgcg ccgacgacg agaacgatgt cgcgattcgt     3060
gaccggcaac gccatgtccg aaggctggct gccgcgacgg ccgatgccgc tgacgacacc    3120
cacaccgtcg acgctatcga cgcagccaac gccgccgagg catccaacaa cgccaccgag    3180
gccgcccgcg aggcacccgc gcggcgac cgcgcctacc tgatcaccgg tggcctgggc      3240
ggcatcgggc tggccctcgc gcgccgcctg gcccgcgacg cgccggcga gctggtgctg     3300 gtatcgcggc gcgccccga ggatgccgag gcccgcgccg cgcacgacat gctggccgcg     3360
gccggcgtgc cgctgaccctg ggtgcgcgcc gacgtcggcg actccgaggc gctgcgcgcc   3420
ggtctcgccg ccgtgcgcct gccgctcggc gggatctacc atgcggccgg cgtgctcgac    3480
gacgcgccac tgcagaacct gaccgacgcg catttcgcgc gcgtgatgca tgccaaggtg    3540
gccggcgcgc tgaaccttga ccgcatcgcc cgggaggccg cgtcgagcg cttcgtgctg     3600 ttctcctcgg tggccgcggt cgtcggctcg gcggggcagg ccaactacgc gagcgcgaac    3660
ggcttcctgg ccgcgcttgg ccgcgcgcgt cgcgccgaag gcctcggcgc gacggtgatc    3720 cactgggcc cctgggccga ggcaggcatg gccggcccgg agcgggtgcg gcagaagatc     3780
gagcgcgccg gcttcgtgct gatcgagccc gaggccgcgc tcgatgcgct gcaggccgtg    3840
ctcgcgcgcg acgaggccga ggccgtgatc gcgcgcttcg actgggcgcg tatcgccgat    3900
tacctggccg atcgcggcgc gcgcccgctg ttcgatcagg tctcgaccgc gccggcgcgg    3960
cccgcggggg cgagcgtcga gatgcgcggc gaggcgctgg ccgatgcagt gcgcgagctg    4020
ctgcagcagg gcgaggcggc cgcggcgcgg cagatgcagg cccacgccga ggccatcgtg    4080
cgcaaggtgc tggcgatcga cgctggcgat gcgatcgacc cggcgcgctc gctgctcgaa    4140
ctcggcatgg attcgctgct gtcggttgag ctgcgcaatc gcttcgccgc gcaatggggc    4200
ctgtcgctgc cggtctcgct gatgttcgac tgcccgagcg tggccgccgt gtcgcggcgc    4260
ctgctcgacg agctgcgctc gaaagagggc acggccgccc cgcgcgccgc cgcaatcgaa    4320
atggcagcgg cgcgccgcg acgcgacgag gcgcgctgcg atatcgccgt gatcggcatg    4380
gcctgccgga tgccggccgg cgcgaacgat gtcggcgcgt tctgggatca actgatctcg    4440
ggtaccgaca tggtccgacc gttcgacggc acgcgctggg atgtaccgcg cttctacacg    4500
cctggctcga ccgaggacgg caagatggtc gccaacgacg gcgtcagat cgccgacgtg     4560 cacggcttcg acaaccgctt cttcggcatc ggcgatcgcg aagccgagta catggacccg    4620
```

```
cagcagcgca tcgcgctcga ggtggcctgg gagaccctcg aatcggccgc ctacacgccc    4680
gagcaactgg ccgacggggc cggcgtgttc atcggcccgg gcccgtccga tttcgccgac    4740
ctgtcgcagc gccatgccgg ggcgctggtc gggctgatgg gccccggcca ccacgtcagc    4800
gcgataccgg gacgcatcgc gcacctgttc gactggcagg ggccctgcat ggcgatcgac    4860
accgcctgct cgtcctcgct ggtggcagtg cacgtggctg cccagcacct gcgcgagcgc    4920
gagtgccgcg tcgcgctggc cggcggcgtc aacgtgatcc tctcgccggc caacaacatc    4980
gtgctgtcga aggccggcat gctgtcgccg gccggccgct gccgcacctt cgatgtcggg    5040
gccgacggct acgtgcgctc cgacggctgc gggatggtgc tgctcaagcg cctcgacgac    5100
gcgctcgccg acggcgacgc gatcctcggc gtgatccgcg gcagcgccgt caaccacaac    5160
ggccggggcc aggggctcac cgcgccgagc agccgccagc aggcgcgcct gatcgaggcg    5220
gcgctggcgc gcgccggcac gctgccgtcc gagatccgct acgtcgaggc gcacggcacc    5280
ggcacgccgc tcggggatcc gatcgagatg gccgcattga aagccaccta cggcgcgcat    5340
cgcgacgcgg ccgatccgct ctacgtgggc gccgtcaagt cggcgatcgg gcataccgag    5400
agcgcagccg gcgtggccgg gttgatcaag gtgctgctga tgatgcggca ccggatgatc    5460
ccgcccacgc tgcacctgaa cacgctcaat ccccacctcg agatcgaccc gcgcacgatc    5520
cgcatcccga ccgccccgca gccgttgctc gcgcgcgagg acggcacgct gagctgcgcg    5580
gtcagctcgt tcggcttcag cggcaccaat gcgcacctga tcgtcgccgc gccgccgggc    5640
aagccggcgc ggccgctcgc gcggagtggg cgcggcctgt tcgcggtgtc ggcgcgcagt    5700
ctgcccgcgc tggcgcgcct ctgcgagcgc catgccgtgc atctggcgcg cgccggcacg    5760
gccgagccgc tcgccgatct ctgtgcgagc acgctgctgg gccggcgccg cttcgagcac    5820
gtcctctgcc tctatccgga cagccatgcc gagctgatcg cgcaactgcg cgcgagcgcg    5880
gcgcggctgc ggcaggcacc ggcaccggcc gcgcccgccg cgatcgacac actggcgctg    5940
cgcctggtcg ccggtgccgc gctgcccgcc gcgacgctgg ccggctggca cgacgagccg    6000
cgtttcgccg ccgcactcgc ggcggcgcgc gacgcgctgt cggcggcaca ggcgggcgag    6060
ccggcaggcg agggcgctcc ggcctcgctc gacgccgcct ggttctgcgt gctgcatgcg    6120
ctgagccact gcatggccgc gttcggtgtc gagccggacc ggatcgacta tcgcggccgg    6180
ctctggctgg cggccgcgcc gatccatcag gccggttcgc tcgacgaggc cgcgcgccgc    6240
ttcctggccg ccgatcccgc gcccgcgccc aagcggctcg gcggcatcgc gctgcggccg    6300
gccgaccagt gcgaaggcga cgaaggcgag ggcggcttcc tcatgctgcg cgacgcgagc    6360
ggccgcgcga cgcgccatct cgatgccgcc gccggcctcg acgacgaggc ctggcgacgc    6420
gccttcggcg cgctctggga aggagggcgc cgggtggact ggctggccgg cttcgccggc    6480
tccgcctacc ggcgcgtggc gctgccggcc tatccgttcg agcaccgcga ctgttcgcgg    6540
cccgcgcggc tgccggccgg cgagcgctcg ctcgagctgc tgctggagga tttgcaggcc    6600
gaataa                                                               6606
```

<210> SEQ ID NO 7
<211> LENGTH: 7935
<212> TYPE: DNA
<213> ORGANISM: Burkholderia ambifaria

<400> SEQUENCE: 7

```
gtgccgttgc tgtcggcctg ccgcgagctc ggaattctcg ccgcgctgca agcgggcccg      60
```

-continued

| | |
|---|---|
| gtcggcctga cgcggctcgg cgcggacctg cgcgcgaacc ccggctatct gcgcctggca | 120 |
| tttcgcgcgc tgcacgcgct cgactgcgtg gcctcggacg atcacgagac ctatggggcg | 180 |
| accgcgcgct ttcgtgcctg cgccgctctg cccgaaggca tcgacacgct gtaccggatc | 240 |
| gacttcgacg cctgcctggg cgaaggcacg caggcgacgc ggctggaacc ctggttcgcg | 300 |
| ctgtcggcgc gcggctggga tagcgaggat accgaatggg cgcaactgct cgacggcgca | 360 |
| ttgacggttc cgctgctgct tgcgctggcc aggcgcggag tggggcgcgg caacggagat | 420 |
| gacgacgcgc gactggacac gcgtgtgcat ccggcgctgc acgcgatgct gcgcgactgg | 480 |
| ctcgcggcgc gccaatggct cgcgccggcg gacgggctca ggctcaacga gcgcggccgg | 540 |
| cacctgtgcg agcgcgcgtt gacgatgggc gtgaccgcct cgtaccggcc gatgctgatg | 600 |
| gcgctgcccg agctgatcgg cggcgatccg cgccgggtgc tgacgcgcga cgccgacggc | 660 |
| cacgagacct atgtggaccg caccctcaac gtgatcggca gcggcttcca gcacggcaag | 720 |
| tatttcaacg acatgccgga cctggtggtc gagctgttcg accgagagcc gctcgacgcg | 780 |
| cagccgcgct acatcgtcga catgggttgc ggcgacgggc cctgctgcg ccatctgtac | 840 |
| aaggcgatcg cgacgcgctc ggcgcgcggc cgctgcctcg atgggtaccc gctgctgttg | 900 |
| atcggcgccg actacaacca gcgctcgctc gacgccgccg gccgcacgct cgagggcctg | 960 |
| ccgcaccttc tggtgcatgc cgacatcggc aagccgcagg cgctgctcga cgcgctgcgc | 1020 |
| gagcacggca tcgacgatcc cgacgcgatc ctgcacgtgc gctcgttcct cgaccacgac | 1080 |
| cggccgctgg acctgacggc cgagccggcc gatgcggcgc agcctgccgc cgacgatcac | 1140 |
| gtctacgtga acgcgcgcgg caactggctg tcctcggcgc gcgtcgcgcg cgacctgcgc | 1200 |
| gagcatcttt cgcgctgggc cggcatcata ggccgccatg gcctgatcgt gctcgaggtg | 1260 |
| ttcgcgctgc cggtgcggct cacgcgcgag tatttcagcc agaccgaaag cttcagcttc | 1320 |
| gatttctatc acgcgctgtc gcgccaggcg ctggtcgacg ccggcacctt ccaccaggcg | 1380 |
| ctggccagcg ccgggctcta tccggatcgc gaatcgctgc gccgctaccc gagcgtcacg | 1440 |
| ccgttctcgc ggatcgtgct gcagcgcgtg catcccaagc cgttcacgat ccgtaccttg | 1500 |
| cagtcggacg acatcccggc cctgctcgag atcgacgcgc gctgctggcc cgagccgctg | 1560 |
| cggttgtcgc gcgaggcgat cgagcagcgc catcgccgtt tccccgaggg gcagttcgtc | 1620 |
| gtcgaatacc aagggcgcgt ggtcggcgtt ctctacacgc agcgcatcga cgatctcgat | 1680 |
| gccgtgctgg ggcgccgtca tgccgactac gccgaagcgc acgtcgccaa cggccgctac | 1740 |
| tggcaactga tctcgatcag cgcgcatccc gatttcccgt cgctggcgct cggcgaccag | 1800 |
| ctgctcgaac acgcgctcga cctggccgcg ctgacggccg gcgtcgaaac ggtctacggc | 1860 |
| atcacgcgtt gtctctcttt tatttcgcaa tccgaaacga tggaggccta tatcggcctg | 1920 |
| cgcgacgcgc acggtcaccc cgtcgatccg ctgctgcgct tccatcacct gcatggcgcc | 1980 |
| agcatcgagc gcgtggtacc gggcgcgcgc cccgaggacc tcgacaacgg cggcgacggc | 2040 |
| gtgctgatcc gctacgagct ttcggcgcgc ttccgcgcgg cgggtgcggc ggccctgccg | 2100 |
| gcggccggcg atgagtgtcg cgagcgcgac acgctcgaag tcgtgtccga atcggtccgg | 2160 |
| cgcatcatgc gcgtgcccga cagcttcgcg gccgattgcc cgctgcgcga gctgggcctc | 2220 |
| gattcgatgg ggctgatgga gctgcgcctg ctgctcggcg ccgcgttctc gatcgagttc | 2280 |
| gatccggccc cgttcttcag ctatccgacc gcgcgcgcga tcgccggcca tatcgacgcg | 2340 |
| cagcgccggc cggccgatgc cgccgcctcg gcctcggtgg gccgtgcctc gttcccggcc | 2400 |
| cggccggacg cgtcgcggcg ggcggatgcc tcggccgatt cgacgaaccc gggcgctgcc | 2460 |

```
gccggcacgc gcgagaccga ggtggcgatc gtcggcatcg cgctgcgttt cccgggcggc   2520
atcgacacgc cgcaagccta ctggcgcatg ctcgacgagg ccgctgcgt gatcggcgag    2580 cgccccgaca cgcgctggcg cgaatatcgc gaggagctgg ccgcgctggc gccggccttg   2640
ccgcagatcc atcgcggcgg tttcctggcc gaggtcgacc gcttcgacgc cgcgttcttc   2700
cgcatcacgc cgcgcgaggc gcaggcgctc gatccgcagc agcggctgct gctcgaactg   2760
gtccacgagg ccttcgagca ggccggcatc gacgccgaca cgcaggccgg cgcgaggtg    2820 ggcgtgttcc tcggcgccta tacgcacgac tacgaggcgc tgacgctgcg cgagcgcgcg   2880
ctcggcgaga tcgacgcctg gttcggctcg ggcaccgcg tgtccacggc ggccgggcgg    2940
cttgcctatt gcttcgattt ccgcggcccc acgatgacga tcgacaccgc ctgctcatcc   3000
tccagcagcg cgatcttctc ggcttgccgc agcctgctcg atggcagcgc ctcgctggcg   3060
gtggctgcct cggtgaacct gatgatcggg ccgtcgctga gcgtggccta cggccgcgcg   3120
agcatgctct cgcccgacgg cctctgcaag accttcgatg ccggcgcgga cggctacgtg   3180
cgcggcgagg gtggcgtggt gctgctgctc aagcgcctcg acgacgcgct ggccgacggc   3240
gaccgcgtcc acgccgtgat caagtcggcc gcgctgatgc aggacggccg caccaacggc   3300
ctgaccgcgc cgaacgggca ggcccaggtg gacgtgatcc gccgcgcgct ggcccaggcc   3360
ggctgcgacc cggccgacat cgactatgtc gaggcgcacg gcaccggcac gcggctcggc   3420
gatccggtcg agatccaggc gctgcacgag gcctattgcg ccggcgtcga gcgtgccgcg   3480
ccgctgtcgg tcggctcggt caagaccaat ctcggtcata ccgaggcggt ctcggggatg   3540
gccggactgg tcaaggtggt gctctcgatg cagcaccgca gggtgcccgc gcatctgcac   3600
ctgaaccagc ccagcccgct gctccggctc gacgaacgca acatcgagat cgcgcggcag   3660
gctcgcgact ggcaggccac gccgggccgc ccgcgccgcg ccggcatcag ctcgttcggc   3720
ttcagcggca gcaacaccca cctgatcgtc gaggaattcg tggcgcccga agccatgccc   3780
gcggcgcctg tcgcggcgcc gctgcctgcg gtggtttcgg ccgcgacgcc ggccgcgctg   3840
cgcgccaatc tcgcgcgcgt ggccgagtat ctcgaagcga gcccggcgcc gctcgacctg   3900
gcggcgctct ctcgcgcgct gacggccggg cgcgcccagc acgcgcgtcg cgtggccttc   3960
agcttcgatt cgaaggaggc gctgcgcgag cgtctcgcgc aggcccaggc cgccgtcgat   4020
cacgacgcgc caccgcgcgc cggcctgcgc atcgccttca tgtacaccgg gcagggtgct   4080
cagtatcacg gcatggcgca gcggctggcc ggcaccagcc cggtgtttcg tgcgcacctg   4140
gagcgctgcg cggcgctggt gcgtgagcat gccggtttcg acctgttcga cctgatgtgg   4200
ggcgagccgc gcgcgcgcat cgacgagacg cgctacacgc aggtcgcgct gttctgcgtc   4260
gagcacagcc tcgcgctgct gctgcgcgag ccggcatcg aggcgagcgt ggtgctgggc    4320
cacagcgtcg gcgaatacgg cgcggcctgc tacgccggcg tgatggaaga agccgccacg   4380
atccgcctgc tgagccgtcg cggcgagctg atgcacgagg gcaccgcgcg cggcgcgatg   4440
gtcgcgctgc tcgcgccgct cgccgaggtc gaggcgctgc tgcgcggctt cgaccggctg   4500
gccgtggccg cgctcaacgg cccgcgcaac caggtggtgg ccggcgattc gcagcagctc   4560
gaggcgctgg tgcggctggc cggcgaacgg cagatcccgg ccttcccgct gccggtcgag   4620
cgcgccttcc actcgccgct gatggcgccg atcctgccgg gcttccgcga gctggccgag   4680
cgcttcgcct atgccgcgcc gcgcgcgacg ctgatctcga acctgacggg cgaggtctgc   4740
cgcggcgcgc ccgacgccgg ctactggacc gatcacattc gccagccggt gcgcttcgag   4800
```

-continued

```
cactcggtgc gcacgctgct cgcgcaggag gtcgacctgg tgatcgagat cggcccgaag    4860
ccggtcctca cccgcatggc gcaggccgtc gcgcccgcgc cgacactgca gtggctgccg    4920
gcgctggtcg atgccgagcg ccatggcctc gccgcgatct tcgcgaaggc cagcgaggcg    4980
gggctggcgg tgaactggcg cgtctatccg cacgagagta ccgcgcggct cgacgatttg    5040
ccgctgtatc gcttccagcg cgagtcgtac tggctgccgg ctctcggcgc gcgcggcgcg    5100
gcaccgggcg cggcgcgcga agccggcgct gccttgccgg attcgccgtc gcaggccggc    5160
tcgcgcgtcg agccgaatgt cgatgcggcc gcgcgtaccg aggtgcgcat cgatccggcg    5220
ctggaccgcg cgccgtgggc gcacgtgatc ggccggcaca gcgtgttccc cgctggcggc    5280
tacctcggct tggcgatcga ggccgcgctg cgctggctcg accgcccggc cggcgtggtg    5340
ctgcgcgggc tgcgtgtcga gcagatgctg cggctggccg aggacggcgc ctaccggctc    5400
gaagcgacgg cccggccggg cgatccgggc gagggcggcg atcccgcccg cgcggcgatc    5460
ctggtgcgca gcgcgggcgg caccggcgcg gcctggacca cgcatgcgcg cgccacggcc    5520
gagccgctgg cggccggcac cgccgcgtcc gtgctcgcgg cgcccgccga tacgcaggcg    5580
gtcgcgatgg acggcgcctc gttctaccgg cgcgtggccg cgctcggcta cgactatgcc    5640
gcgccgttcc gcggcattac ctggctgcgc gcgccggcc acagcatcgg cgccgaccta    5700
tcggccgccg gcacgcccga gccggacggc tacgcggccg cgccctggcg cctcgaccat    5760
tgcctgcaga ccgtgctggc cgcgaggctc gaggcgctgg aagccgatgg cgcgcaccta    5820
ctgctgccga ccggcgtcga gcgcctggtc tggcacggcc cgctgccggc cgcgccgcgc    5880
gtggtctgcc gcgtgcgcgc gcatcacgat ggcgtcgagg ccgaactgcg tatcaccgac    5940
gcccagggca agccgtgttg cgagatggag ggcctgcgct ttgcgcgcgt cgatcgtcgc    6000
gggctggccg gcgcgggcgg cgctgcctcg gtggtgtcgc ccgcgtccgc accgtcgcga    6060
tccgcctcgc cgctgcacgc gctgcgctgg cggcgcgtcg acccgccttc cgtcgccgcc    6120
gacgaggccg ccggtcctg gctggtcgtt agccgccgcg gcgcgtcggg cggtgccttc    6180
gccgccgcgc tcggcgcgcg cggtgcccgc gtcgagcggc tcgatccgcg cgacgcgcat    6240
gacgcggccg gcctggccgc cttcgcgcgc agcctggccg actacgccgc ggcgcgggcc    6300
gagccgttcg gcctgatcca tctgcacgcg gacgccgccg tcgatctcgc cgtggtccgt    6360
ttcctcgccg gcctgcccgc cggctgcctg catcgcgcgc tgctggtcac gcagggcgcg    6420
caggccgtgg cgggcgagtt gcccgatctg tcggcgaccg tgctctgggg gctcggcgcc    6480
acgctgcagg ccgaggcgcc gcagcaggcg gtcacgctgg tcgatctgga ggcgggcctc    6540
gacgcgctgg tcgggatcga gaccgtgctc aacgccgccg atgccatcga cgccggcgcc    6600
gcgcgcgccc ccgcgtggcc cgatcatctc gcgctgcgcg cgggccgctg gcaccagcgc    6660
gtgctcgcgc cggccaccgc gcgcggtccg ctgacgattt ccggcgacgg cagctacctg    6720
gtgacgggcg gcctgggcgg cctcggccgt cgcgtcgtcg aattcctgca tgcacgcggc    6780
gcgggccgca tcgtcgtgct cgggcgcacg ctgccgccg agccgccggc ctggctcgcg    6840
gcgttgcagg cggaacgtgc cgttgtcgaa ctggtggcct gcgatctaag cgatgccgcg    6900
cgggtcgcga gcgtgccggg cacgctgggg cgcgagctgc cgctgcgcgg catcgtgcat    6960
gcggccgggg tgctcgacga tgcgcgcctg atcgaccagg atgcggcgcg cctgcggcgc    7020
gtggcggcgc ccaagctcga cggcgcgcgc catctgctgg acgcgctggc tggcgcatcg    7080
ctggccgcgt cgctcgattt cgtctggctg ttctcgtcga tcaccgcgct gcacggcggc    7140
gcgggccagg ccaactacgc ggccgccaat gccgcgctcg acggctacgc ccacacgctg    7200
```

-continued

```
cgcgcacgcg gcgtgccggc caccgcgatc aactgggggc cgtggcgcga taccgggatg    7260
ctggcgcgcg tggcgcggcc cgaggccacc tatgcgcggc tgcatgccga tccgctcgag    7320
cccgccgagg cggcgcgctg gttcgatgcg ctgctcgcca ccgacggcgc gcagctctgc    7380
gtggtgcact ggcgcctcga tgcgctggcg cgcgtgccgg gctgccgc gctgctgcgc      7440 gacctggtga cggccgcgac atcggtggcg acaccggcca cggccgggca ggccggtccc    7500
gcgtcctacc ggcagcggct cgccgatgcg ctgccagccg aacgccgc gctggcgcgg     7560 cgcctggtgg ccgagcagat cgcgctggtc accggcatcg ccgccgcgac gatcgagccg    7620
gccgcgccgc tcagcatact cggcatggat tcgctgatga gcgtcgcgct cagcgacgcg    7680
ctggcccact gccttggcat cgccgcctcg gccacgctgc tgttcgacca cccgacgctc    7740
gacgcgctgg ccctgcacgt gctggcggcc aatgcgcccg ccgggtccgc cgtggcggag    7800
gccgcgtccg ttgcgccggc ggtcgaagcc acggaacccg ccgcggcccc gctcgatacc    7860
gagctcagcg aaatcgaggg attgcaggac gacgatctgg ccgcgctgct cggcaaggag    7920
ttcatccgtg aataa                                                    7935
```

```
<210> SEQ ID NO 8
<211> LENGTH: 20
<212> TYPE: DNA
<213> ORGANISM: Burkholderia ambifaria

<400> SEQUENCE: 8
gctgggatag cgaggatacc                                                 20

<210> SEQ ID NO 9
<211> LENGTH: 20
<212> TYPE: DNA
<213> ORGANISM: Burkholderia ambifaria

<400> SEQUENCE: 9
cagaagatcc aggcgttgtc                                                 20

<210> SEQ ID NO 10
<211> LENGTH: 19
<212> TYPE: DNA
<213> ORGANISM: Burkholderia ambifaria

<400> SEQUENCE: 10
aacgtgcctt cgacgagat                                                  19

<210> SEQ ID NO 11
<211> LENGTH: 20
<212> TYPE: DNA
<213> ORGANISM: Burkholderia ambifaria

<400> SEQUENCE: 11
ccgttgaagc cgtagtgata                                                 20

<210> SEQ ID NO 12
<211> LENGTH: 19
<212> TYPE: DNA
<213> ORGANISM: Burkholderia ambifaria

<400> SEQUENCE: 12
ggcgtgaacc tgatcctttt                                                 19

<210> SEQ ID NO 13
```

```
<211> LENGTH: 20
<212> TYPE: DNA
<213> ORGANISM: Burkholderia ambifaria

<400> SEQUENCE: 13
aatctgcgga ttgagggtct                                              20
```